(12) United States Patent
Wang et al.

(10) Patent No.: US 12,398,140 B2
(45) Date of Patent: Aug. 26, 2025

(54) SUBSTITUTED PYRROLO [2,3-D]PYRIMIDINES FOR TREATING FAMILIAL DYSAUTONOMIA

(71) Applicant: PTC THERAPEUTICS, INC., Warren, NJ (US)

(72) Inventors: Jiashi Wang, West New York, NJ (US); Michael A. Arnold, Flemington, NJ (US); Amal Dakka, Whitehouse Station, NJ (US); Gary Mitchell Karp, Princeton Junction, NJ (US); Jana Narasimhan, Scotch Plains, NJ (US); Nikolai A. Naryshkin, East Brunswick, NJ (US); Nanjing Zhang, Princeton, NJ (US)

(73) Assignee: PTC THERAPEUTICS, INC., Warren, NJ (US)

( * ) Notice: Subject to any disclaimer, the term of this patent is extended or adjusted under 35 U.S.C. 154(b) by 847 days.

(21) Appl. No.: 17/430,566

(22) PCT Filed: Feb. 10, 2020

(86) PCT No.: PCT/US2020/017423
§ 371 (c)(1),
(2) Date: Aug. 12, 2021

(87) PCT Pub. No.: WO2020/167624
PCT Pub. Date: Aug. 20, 2020

(65) Prior Publication Data
US 2022/0135568 A1    May 5, 2022

Related U.S. Application Data

(60) Provisional application No. 62/805,281, filed on Feb. 13, 2019.

(51) Int. Cl.
*A61K 31/519* (2006.01)
*C07D 487/04* (2006.01)

(52) U.S. Cl.
CPC .................. *C07D 487/04* (2013.01)

(58) Field of Classification Search
CPC ...................... A61K 31/519; C07D 487/04
USPC ........................ 514/265.1; 544/280
See application file for complete search history.

(56) References Cited

U.S. PATENT DOCUMENTS

| | | | |
|---|---|---|---|
| 3,475,429 | A | 10/1969 | Woitun et al. |
| 5,532,257 | A | 7/1996 | Senju et al. |
| 5,654,307 | A | 8/1997 | Bridges et al. |
| 6,211,195 | B1 | 4/2001 | Webb et al. |
| 6,492,383 | B1 | 12/2002 | Munchhof et al. |
| 7,737,110 | B2 | 6/2010 | Slaugenhaupt et al. |
| 2004/0138251 | A1 | 7/2004 | Boschelli et al. |
| 2012/0053173 | A1 | 3/2012 | Banno et al. |
| 2013/0209549 | A1 | 8/2013 | Dickey |
| 2013/0317045 | A1 | 11/2013 | Hadd et al. |
| 2014/0005183 | A1 | 1/2014 | Galatsis et al. |
| 2014/0323544 | A1 | 10/2014 | Bestwick et al. |
| 2015/0344497 | A1 | 12/2015 | Zhou et al. |
| 2016/0002273 | A1 | 1/2016 | Blum et al. |
| 2018/0118748 | A1 | 5/2018 | Slaugenhaupt et al. |
| 2018/0258425 | A1 | 9/2018 | Rigo et al. |
| 2019/0000844 | A1 | 1/2019 | Babu et al. |
| 2020/0239940 | A1 | 7/2020 | Guo et al. |
| 2022/0056043 | A1 | 2/2022 | Li et al. |
| 2024/0024490 | A1 | 1/2024 | Choudhary |

FOREIGN PATENT DOCUMENTS

| | | |
|---|---|---|
| CA | 3082907 A1 | 5/2019 |
| CL | 202102104 | 4/2022 |
| CN | 103242341 A | 8/2013 |
| CN | 110312528 A | 10/2019 |
| CO | NC20170011017 A2 | 3/2018 |
| CO | NC2018001425 A2 | 5/2018 |
| CO | NC20180013803 A2 | 1/2019 |
| CO | 20210008895 A2 | 7/2021 |
| EP | 2014663 A1 | 1/2009 |
| EP | 3020829 A1 | 5/2016 |

(Continued)

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
International Search Report for PCT/US2022/075966 date mailed Jan. 19, 2023.
Written Opinion for PCT/US2022/075966 date mailed Jan. 19, 2023.
Pubchem, SID 274791846, Modify Date: Nov. 21, 2016, Available: Dec. 18, 2015.
International Search Report for PCT/US2022/2075967 date mailed Jan. 19, 2023.

(Continued)

*Primary Examiner* — Douglas M Willis
(74) *Attorney, Agent, or Firm* — Hoffmann & Baron, LLP

(57) ABSTRACT

The present description relates to compounds of formula (I) useful for improving pre-mRNA splicing in a cell. In particular, another aspect described herein relates to substituted pyrrolo[2,3-d]pyrimidine compounds, forms, and pharmaceutical compositions thereof and methods of use for treating or ameliorating familial dysautonomia.

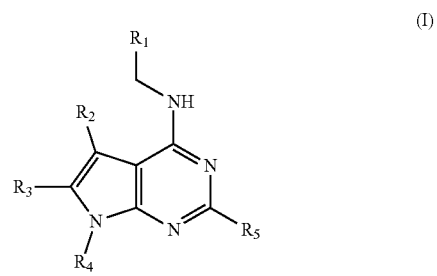

13 Claims, No Drawings

(56) References Cited

FOREIGN PATENT DOCUMENTS

| | | | |
|---|---|---|---|
| EP | 3828829 A1 | 6/2021 | |
| JP | 2009007341 A | 1/2009 | |
| KR | 10239070 B1 | 4/2022 | |
| WO | 2004/065392 A1 | 8/2004 | |
| WO | 2005007083 A2 | 1/2005 | |
| WO | 2009085226 A2 | 7/2009 | |
| WO | 2010/118367 A2 | 10/2010 | |
| WO | 2013026516 A1 | 2/2013 | |
| WO | 2014/124458 A1 | 8/2014 | |
| WO | 2015053624 A2 | 4/2015 | |
| WO | 2016115434 A1 | 7/2016 | |
| WO | 2017053781 A1 | 3/2017 | |
| WO | 2018075937 A1 | 4/2018 | |
| WO | 2018134685 A2 | 7/2018 | |
| WO | 2020167628 A1 | 8/2020 | |
| WO | WO-2020167624 A1 * | 8/2020 | ............. A61P 25/00 |
| WO | 2020245233 A1 | 12/2020 | |
| WO | 2021118929 A1 | 6/2021 | |
| WO | 2021142351 A1 | 7/2021 | |
| WO | 2022169864 A1 | 8/2022 | |
| WO | 2022169866 A1 | 8/2022 | |
| WO | 2022169868 A1 | 8/2022 | |
| WO | 2023039368 A1 | 3/2023 | |
| WO | 2023039369 A1 | 3/2023 | |
| WO | 2023039370 A1 | 3/2023 | |
| WO | 2023081858 A1 | 5/2023 | |
| WO | 2023250316 A1 | 12/2023 | |

OTHER PUBLICATIONS

Written Opinion for PCT/US2022/075967 date mailed Jan. 19, 2023.
Pubchem, SID 365025105, Available Date: May 25, 2018.
Pubchem, SID 439055238, Available Date: Dec. 19, 2020.
International Search Report for PCT/US2022/075969 date mailed Jan. 19, 2023.
Written Opinion for PCT/US2022/075969 date mailed Jan. 19, 2023.
Pubchem, SID 377008396, Available Date: Dec. 4, 2018.
International Search Report for PCT/US2020/017423 date mailed May 12, 2020.
Written Opinion for PCT/US2020/017423 date mailed May 12, 2020.
International Search Report for PCT/US2020/017430 date mailed May 19, 2020.
Written Opinion for PCT/US2020/017430 date mailed May 19, 2020.
International Search Report for PCT/US2020/063612 date mailed Mar. 1, 2021.
Written Opinion for PCT/US2020/063612 date mailed Mar. 1, 2021.
Panchal et al., "Evaluation of basic, heterocyclic ring systems as templates for use as potassium competitive acid blockers (pCABs)", Bioorganic & Medicinal Chemistry Letters, vol. 19, No. 23, Dec. 1, 2009 (Dec. 1, 2009), available online Jul. 4, 2009, pp. 6813-6817, XP026736113.
Database Registry [Online] Chemical Abstracts Service, Columbus, Ohio, US; May 2, 2017 (May 2, 2017), XP002802124, Database accession No. 2094356-55-3, 7-methyl-N-[[1-methyl-3-(trifluoromethyl)-thieno[3,2-d]pyrimidin-4-amine.
International Search Report for PCT/US2022/014929 date mailed Jun. 21, 2022.
Written Opinion for PCT/US2022/014929 date mailed Jun. 21, 2022.
International Search Report for PCT/US2022/014932 date mailed Jun. 15, 2022.
Written Opinion for PCT/US2022/014932 date mailed Jun. 15, 2022.
International Search Report for PCT/US2022/014934 date mailed Jun. 15, 2022.
Written Opinion for PCT/US2022/014934 date mailed Jun. 15, 2022.
Pubchem, SID 389066036, Available Date: Dec. 6, 2019.
Vippagunta et al., "Crystalline solids," Advanced Drug Delivery Reviews, vol. 48, Issue 1, May 16, 2001, pp. 3-26.
V. Craig Jordan, "Tamoxifen: A Most Unlikely Pioneering Medicine," Nature Reviews: Drug Discovery, vol. 2 (Mar. 2003) pp. 205-213.
Xiong Shu-Hua et al., "Diagnosis and Treatment Update on Autoimmune Autonomic Gangliopathy," pp. 690-693 a Chinese journal of clinical neuroscience No. 20 vol. 6 Dec. 31, 2012.
CAS Database Registry STN No. 1349454-03-0, entered on Dec. 6, 2011.
"Chemical Encyclopedia", scientific publishing house "Great Russian Encyclopedia," Moskva, vol. 4, pp. 499-501, 1995.
CAS Database Registry STN No. 2167522-70-3, entered on Jan. 1, 2018.
CAS Database Registry STN No. 2021176-84-9, entered on Oct. 28, 2016.
CAS Database Registry STN No. 1881342-47-7, entered on Mar. 8, 2016.
CAS Database Registry STN No. 1878819-09-0, entered on Mar. 3, 2016.
CAS Database Registry STN No. 1876870-61-9, entered on Mar. 1, 2016.
CAS Database Registry STN No. 1876583-64-0, entered on Mar. 1, 2016.
CAS Database Registry STN No. 1876399-06-2, entered on Feb. 29, 2016.
CAS Database Registry STN No. 1874906-94-1, entered on Feb. 26, 2016.
CAS Database Registry STN No. 1870492-22-0, entered on Feb. 19, 2016.
CAS Database Registry STN No. 1858986-81-8, entered on Feb. 3, 2016.
CAS Database Registry STN No. 1858871-72-3, entered on Feb. 3, 2016.
CAS Database Registry STN No. 2302366-29-4, entered on Apr. 7, 2016.
CAS Database Registry STN No. 2300574-14-3, entered on Apr. 4, 2016.
CAS Database Registry STN No. 2299694-59-8, entered on Apr. 3, 2019.
CAS Database Registry STN No. 2299370-15-1, entered on Apr. 3, 2019.
CAS Database Registry STN No. 2295625-99-7, entered on Mar. 28, 2019.
CAS Database Registry STN No. 2295625-98-6, entered on Mar. 28, 2019.
CAS Database Registry STN No. 2294501-42-9, entered on Mar. 27, 2019.
CAS Database Registry STN No. 2294382-59-3, entered on Mar. 27, 2019.
CAS Database Registry STN No. 2294379-83-0, entered on Mar. 27, 2019.
CAS Database Registry STN No. 2294353-32-3, entered on Mar. 27, 2019.
CAS Database Registry STN No. 2293758-23-1, entered on Mar. 26, 2019.
CAS Database Registry STN No. 2293235-24-0, entered on Mar. 26, 2019.
CAS Database Registry STN No. 2293231-63-5, entered on Mar. 26, 2019.
CAS Database Registry STN No. 2293211-33-1, entered on Mar. 26, 2019.
CAS Database Registry STN No. 2293211-30-8, entered on Mar. 26, 2019.
Gold-Von Simson, et al., "Kinetin in Familial Dysautonomia Carriers: Implication for a New Therapeutic Strategy Targeting mRNA Splicing," Pediatric Research, vol. 65(3), pp. 341-346, Mar. 2009.

(56) References Cited

OTHER PUBLICATIONS

Pedro J. Campos et al., "A Versatile Synthesis of Pyrrolo-, Furo- and Thienopyridines via Photocyclization of 3-Amino-2-alkene Imines in an Acid Medium," Tetrahedron, vol. 55, pp. 14079-14088, Dec. 3, 1999.
Sylvia L. Anderson et al., "Familial Dysautonomia Is Caused by Mutations of the IKAP Gene," Am. J. Hum. Genet., vol. 68, pp. 753-758, electronically published Jan. 22, 2001.
David Cheishvili et al., "IKAP/Elp1 involvement in cytoskeleton regulation and implication for familial dysautonomia," Human Molecular Genetics, vol. 20(8), pp. 1584-1594, Advance Access published Jan. 27, 2011.
Michael J. Munchhof et al., "Design and SAR of thienopyrimidine and thienopyridine inhibitors of VEGFR-2 kinase activity," Bioorg. & Med. Chem. Lett., vol. 14, 2004, pp. 21-24, Jan. 5, 2004.
David Cheishvili et al., "IKAP/hELP1 deficiency in the cerebrum of familial dysautonomia patients results in down regulation of genes involved in oligodendrocyte differentiation and in myelination," Human Molecular Genetics, 2007, vol. 16(17), pp. 2097-2104, Advanced Access published Jun. 25, 2007.
Evers Melvin M. et al., "Ataxin-3 protein modification as a treatment strategy for spinocerebellar ataxia type 3: Removal of the CAG containing exon", Neurobiology of Disease, [Online] vol. 58, May 6, 2013 (May 6, 2013), pp. 49-56, XP093217684.
Craig S. McIntosh et al., "Removal of the Polyglutamine Repeat of Ataxin-3 by Redirecting pre-mRNA Processing", International Journal of Molecular Sciences, vol. 20, No. 21, Oct. 31, 2019 (Oct. 31, 2019), p. 5434, XP055712430.
Lodewijk J. A. Toonen et al., "Antisense oligonucleotide-mediated exon skipping as a strategy to reduce proteolytic cleavage of ataxin-3," Scientific Reports, vol. 6, No. 1, Oct. 12, 2016 (Oct. 12, 2016), XP055563933.
CAS Database Registry STN No. 2371515-24-9, entered on Sep. 1, 2019.
CAS Database Registry STN No. 1981326-49-1, entered on Aug. 28, 2016.
CAS Database Registry STN No. 1967610-91-8, entered Aug. 5, 2016.
CAS Database Registry STN No. 2327421-67-8, entered on Jun. 10, 2019.
CAS Database Registry STN No. 878601-07-1, entered on Mar. 30, 2006.
CAS Database Registry STN No. 879332-90-8, entered on Apr. 5, 2006.
CAS Database Registry STN No. 1349123-32-5, entered on Dec. 5, 2011.
CAS Database Registry STN No. 1967539-15-6, entered on Aug. 5, 2016.
CAS Database Registry STN No. 1914470-24-8, entered on May 20, 2016.
Klockgether Thomas et al: "Spinocerebellar ataxia", Nature Reviews Disease Primers, Nature Publishing Group UK, London, vol. 5, No. 1, Apr. 11, 2019 (Apr. 11, 2019), pp. 1-21, XP036756583.
Written Opinion for PCT/US2023/068717 date mailed Nov. 8, 2023.
International Search Report for PCT/US2023/068717 date mailed Nov. 8, 2023.
Berish Y Rubin et al., "IKBKAP/ELPI gene mutations: mechanisms of familial dysautonomia and gene-targeting therapies," The Application of Clinical Genetics, 10, pp. 95-103 Dec. 15, 2017.
Ranjit S. Shetty et al., "Specific correction of a splice defect in brain by nutritional supplementation," Human Molecular Genetics, vol. 20, No. 21, pp. 4093-4101, Aug. 5, 2011.
Felicia B. Axelrod et al., "Kinetin improves IKBKAP mRNA splicing in patients with familial dysautonomia," Pediatric Research, 70(5), pp. 480-483, Nov. 2011.
Mayumi Yoshida et al., "Rectifier of aberrant mRNA splicing recovers (RNA modification in familial dysautonomia," PNAS vol. 112, No. 9, pp. 2764-2769, Mar. 3, 2015.
Elisabetta Morini et al., "Development of an oral treatment that rescues gait ataxia and retinal degeneration in a phenotypic mouse model of familial dysautonomia," The American Journal of Human Genetics, 110(3), p. 531-547, Mar. 2, 2023, E-publication on Feb. 20, 2023.
Reeteka Sud et al., "Antisense-mediated Exon Skipping Decreases Tau Protein expression: A Potential Therapy For Tauopathies," Molecular Therapy-Nucleic Acids, 3, 2014, 7, published online Jul. 29, 2014, p. e180.
Fei Liu et al., "Tau exon 10 alternative splicing and tauopathies," Molecular Neurodegeneration, 3, 2008, 1, published Jul. 10, 2008, p. 8.
CAS Database Registry STN No. 939979-48-3, entered on Jun. 28, 2007.
CAS Database Registry STN No. 1098386-78-7, entered on Feb. 1, 2009.

\* cited by examiner

SUBSTITUTED PYRROLO [2,3-D]PYRIMIDINES FOR TREATING FAMILIAL DYSAUTONOMIA

CROSS-REFERENCE TO RELATED APPLICATIONS

This application is the National Stage of International Application No. PCT/US2020/017423, filed Feb. 10, 2020, which claims priority to U.S. Provisional Application No. 62/805,281 filed on Feb. 13, 2019.

STATEMENT OF JOINT RESEARCH AGREEMENT

The subject matter disclosed was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties of the joint research agreement are PTC Therapeutics, Inc. and The General Hospital Corporation, d/b/a Massachusetts General Hospital.

TECHNICAL FIELD

An aspect of the present description relates to compounds useful for improving pre-mRNA splicing in a cell. In particular, another aspect of the present description relates to substituted pyrrolo[2,3-d]pyrimidine compounds, forms, and pharmaceutical compositions thereof and methods of use for treating or ameliorating familial dysautonomia.

BACKGROUND

Familial dysautonomia (FD) is a congenital sensory and autonomic neuropathy (HSAN) of the central and peripheral nervous system characterized by widespread sensory and variable autonomic dysfunction. FD affects neuronal development and is associated with progressive neuronal degeneration. Multiple systems are affected resulting in a markedly reduced quality of life and premature death. FD is caused by mutations in the IKBKAP (also referred to as ELPI) gene and in all cases described to date there is at least one allele carrying a T to C mutation at position 6 in intron 20 that results in a unique pattern of tissue-specific exon skipping.

Kinetin derivatives useful for therapeutically targeting pre-mRNA splicing mechanisms and the treatment of FD have been described in International Patent Application No. WO2016/115434, the disclosure of which is incorporated by reference in its entirety.

All other documents referred to herein are incorporated by reference into the present application as though fully set forth herein.

SUMMARY

An aspect of the present description includes compounds comprising, a compound of

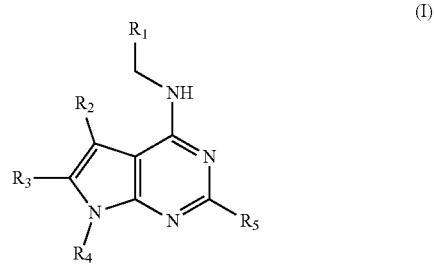

or a form thereof, wherein $R_1$, $R_2$, $R_3$, $R_4$, and $R_5$ are defined herein.

An aspect of the present description includes a method for use of a compound of Formula (I) or a form or composition thereof for treating or ameliorating FD in a subject in need thereof comprising, administering to the subject an effective amount of the compound of Formula (I) or a form or composition thereof.

An aspect of the present description includes a use for a compound of Formula (I) or a form thereof for treating or ameliorating FD in a subject in need thereof comprising, administering to the subject an effective amount of the compound of Formula (I) or a form thereof.

An aspect of the present description includes a use for a compound of Formula (I) or a form thereof in the manufacture of a medicament for treating or ameliorating FD in a subject in need thereof comprising, administering to the subject an effective amount of the medicament.

DETAILED DESCRIPTION

An aspect of the present description relates to compounds comprising, a compound of Formula (I):

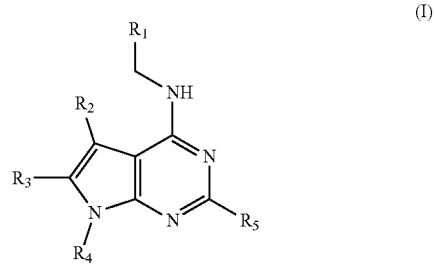

or a form thereof, wherein:
$R_1$ is phenyl or heteroaryl, optionally substituted with one, two, three, or four, independently selected $R_{1a}$ substituents,
wherein heteroaryl is a 5-8 membered monocyclic or bicyclic aromatic carbon atom ring structure radical containing 1-3 heteroatoms selected from N, O, and S;
$R_{1a}$ is cyano, halo, hydroxy, $C_{1-6}$alkyl, halo-$C_{1-6}$alkyl, deutero-$C_{1-6}$alkyl, or $C_{1-6}$alkoxy;
$R_2$ is hydrogen, halo, or $C_{1-6}$alkyl;
$R_3$ is $C_{2-6}$alkyl, optionally substituted with one, two, three, or four independently selected $R_{3a}$ substituents, wherein $C_{2-6}$alkyl may optionally contain a chiral carbon having an (R) or (S) configuration;

$R_{3a}$ is cyano, halo, hydroxy, $C_{1-6}$alkyl, halo-$C_{1-6}$alkyl, deutero-$C_{1-6}$alkyl, $C_{1-6}$alkoxy, amino, $C_{1-6}$alkylamino, deutero-$C_{1-6}$alkyl-amino, and $(C_{1-6}alkyl)_2$-amino;

$R_4$ is hydrogen, $C_{1-6}$alkyl, or phenyl,
wherein each instance of $C_{1-6}$alkyl or phenyl are optionally substituted with one, two, three, or four independently selected $R_{4a}$ substituents; and $R_{4a}$ is cyano, halo, hydroxy, $C_{1-6}$alkyl, halo-$C_{1-6}$alkyl, or $C_{1-6}$alkoxy;

$R_5$ is hydrogen, halo, or $C_{1-6}$alkyl;
wherein the form of the compound is selected from the group consisting of a salt, hydrate, solvate, and tautomer form thereof.

One aspect includes a compound of Formula (I), wherein $R_1$ is phenyl or heteroaryl, optionally substituted with one, two, three, or four, independently selected $R_{1a}$ substituents, wherein heteroaryl is a 5-8 membered monocyclic or bicyclic aromatic carbon atom ring structure radical containing 1-3 heteroatoms selected from N, O, and S.

Another aspect includes a compound of Formula (I), wherein $R_1$ is phenyl, optionally substituted with one, two, three, or four, independently selected $R_{1a}$ substituents.

Another aspect includes a compound of Formula (I), wherein $R_1$ is phenyl, optionally substituted with one $R_{1a}$ substituent.

Another aspect includes a compound of Formula (I), wherein $R_1$ is heteroaryl, optionally substituted with one, two, three, or four, independently selected $R_{1a}$ substituents, wherein heteroaryl is a 5-8 membered monocyclic or bicyclic aromatic carbon atom ring structure radical containing 1-3 heteroatoms selected from N, O, and S.

Another aspect includes a compound of Formula (I), wherein $R_1$ is heteroaryl, optionally substituted with one $R_{1a}$ substituent, wherein heteroaryl is a 5-8 membered monocyclic or bicyclic aromatic carbon atom ring structure radical containing 1-3 heteroatoms selected from N, O, and S.

Another aspect of includes a compound of Formula (I), wherein $R_1$ is heteroaryl selected from furanyl, thiophenyl, 1H-pyrazolyl, 1H-imidazolyl, isoxazolyl, 1,3-thiazolyl, 1,3-oxazolyl, tetrazolyl, 1,2,3-triazolyl, 1,2,4-oxadiazolyl, 1,3,4-oxadiazolyl, 1,2,3-thiadiazolyl, pyridinyl, pyrimidinyl, pyrazinyl, pyridazinyl, benzofuranyl, and quinolinyl, wherein heteroaryl is optionally substituted with one, two, three, or four, independently $R_{1a}$ substituents.

Another aspect of includes a compound of Formula (I), wherein $R_1$ is heteroaryl selected from furanyl, thiophenyl, 1,3-thiazolyl, 1,3-oxazolyl, and pyridinyl, wherein heteroaryl is optionally substituted with one, two, three, or four, independently $R_{1a}$ substituents.

Another aspect includes a compound of Formula (I), wherein $R_1$ is heteroaryl selected from furan-2-yl, furan-3-yl, thiophen-2-yl, thiophen-3-yl, 1H-pyrazol-3-yl, 1H-pyrazol-4-yl, 1H-pyrazol-5-yl, 1H-imidazol-1-yl, 1H-imidazol-4-yl, isoxazol-3-yl, isoxazol-4-yl, isoxazol-5-yl, 1,3-thiazol-2-yl, 1,3-thiazol-4-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, tetrazol-5-yl, 1,2,3-triazol-4-yl, 1,2,3-triazol-5-yl, 1,2,3-thiadiazol-4-yl, 1,2,3-thiadiazol-5-yl, pyridin-2-yl, pyridin-3-yl, pyridin-4-yl, pyrimidin-4-yl, pyrazin-2-yl, pyridazin-3-yl, pyridazin-4-yl, benzofuran-2-yl, benzofuran-5-yl, and quinoline-4-yl, wherein heteroaryl is optionally substituted with one, two, three, or four, independently $R_{1a}$ substituents.

Another aspect includes a compound of Formula (I), wherein $R_1$ is heteroaryl selected from furan-2-yl, furan-3-yl, thiophen-2-yl, 1,3-thiazol-2-yl, 1,3-thiazol-4-yl, 1,3-thiazol-5-yl, 1,3-oxazol-2-yl, pyridin-2-yl, pyridin-3-yl, and pyridin-4-yl, wherein heteroaryl is optionally substituted with one, two, three, or four, independently $R_{1a}$ substituents.

One aspect includes a compound of Formula (I), wherein $R_{1a}$ is cyano, halo, hydroxy, $C_{1-6}$alkyl, halo-$C_{1-4}$alkyl, deutero-$C_{1-6}$alkyl, or $C_{1-6}$alkoxy.

Another aspect includes a compound of Formula (I), wherein $R_{1a}$ is halo.

Another aspect includes a compound of Formula (I), wherein $R_{1a}$ is halo selected from fluoro, chloro, bromo, and iodo.

Another aspect includes a compound of Formula (I), wherein $R_{1a}$ is fluoro.

One aspect includes a compound of Formula (I), wherein $R_2$ is hydrogen, halo, or $C_{1-6}$alkyl.

Another aspect includes a compound of Formula (I), wherein $R_2$ is hydrogen.

Another aspect includes a compound of Formula (I), wherein $R_2$ is halo.

Another aspect includes a compound of Formula (I), wherein $R_2$ is halo selected from fluoro, chloro, bromo, and iodo.

Another aspect includes a compound of Formula (I), wherein $R_2$ is halo selected from fluoro, chloro, and bromo.

Another aspect includes a compound of Formula (I), wherein $R_2$ is $C_{1-6}$alkyl.

Another aspect includes a compound of Formula (I), wherein $R_2$ is $C_{1-6}$alkyl selected from methyl, ethyl, propyl, isopropyl, butyl, sec-butyl, isobutyl, tert-butyl, pentyl, isopentyl, hexyl, or isohexyl.

Another aspect includes a compound of Formula (I), wherein $R_2$ is $C_{1-6}$alkyl selected from methyl and butyl.

One aspect includes a compound of Formula (I), wherein $R_3$ is $C_{2-6}$alkyl, optionally containing a chiral carbon having an (R) or (S) configuration.

Another aspect includes a compound of Formula (I), wherein $R_3$ is $C_{2-6}$alkyl, optionally substituted with one, two, three, or four, independently selected $R_{3a}$ substituents.

Another aspect includes a compound of Formula (I), wherein $R_3$ is $C_{2-6}$alkyl selected from ethyl, propyl, butyl, pentyl, and hexyl, optionally substituted with one, two, three, or four independently selected $R_{3a}$ substituents.

Another aspect includes a compound of Formula (I), wherein $R_3$ is $C_{2-6}$alkyl selected from ethyl, propyl, butyl, and pentyl, optionally substituted with one, two, three, or four independently selected $R_{3a}$ substituents.

Another aspect includes a compound of Formula (I), wherein $R_3$ is $C_{2-6}$alkyl selected from ethyl, propyl, butyl, pentyl, and hexyl, optionally substituted with one, two, three, or four independently selected $R_{3a}$ substituents, and wherein $C_{2-6}$alkyl contains a chiral carbon having an (R) configuration.

Another aspect includes a compound of Formula (I), wherein $R_3$ is $C_{2-6}$alkyl selected from ethyl, propyl, butyl, and pentyl, optionally substituted with one, two, three, or four independently selected $R_{3a}$ substituents, and wherein $C_{2-4}$alkyl contains a chiral carbon having an (R) configuration.

Another aspect includes a compound of Formula (I), wherein $R_3$ is $C_{2-6}$alkyl, optionally substituted with one, two, three, or four independently selected $R_{3a}$ substituents, and wherein, $C_{2-4}$alkyl contains a chiral carbon having an (S) configuration.

Another aspect includes a compound of Formula (I), wherein $R_3$ is $C_{2-6}$alkyl selected from ethyl, propyl, butyl, pentyl, and hexyl, optionally substituted with one, two, three, or four independently selected $R_{3a}$ substituents, and wherein $C_{2-6}$alkyl contains a chiral carbon having an (S) configuration.

Another aspect includes a compound of Formula (I), wherein $R_3$ is $C_{2-6}$alkyl selected from ethyl, propyl, butyl, and pentyl, optionally substituted with one, two, three, or four independently selected $R_{3a}$ substituents, and wherein $C_{2-6}$alkyl optionally contains a chiral carbon having an (S) configuration.

One aspect includes a compound of Formula (I), wherein $R_{3a}$ is cyano, halo, hydroxy, $C_{1-6}$alkyl, halo-$C_{1-61-6}$alkyl, deutero-$C_{1-6}$alkyl, $C_{1-6}$alkoxy, amino, $C_{1-6}$alkyl-amino, deutero-$C_{1-6}$alkyl-amino, and $(C_{1-6}$alkyl$)_2$-amino.

Another aspect includes a compound of Formula (I), wherein $R_{3a}$ is hydroxy, $C_{1-6}$alkyl, $C_{1-6}$alkoxy, amino, $C_{1-6}$alkyl-amino, deutero-$C_{1-6}$alkyl-amino, and $(C_{1-6}$alkyl$)_2$-amino.

Another aspect includes a compound of Formula (I), wherein $R_{3a}$ is hydroxy.

Another aspect includes a compound of Formula (I), wherein $R_{3a}$ is $C_{1-6}$alkyl selected from methyl, ethyl, propyl, isopropyl, butyl, sec-butyl, isobutyl, tert-butyl, pentyl, isopentyl, hexyl, and isohexyl.

Another aspect includes a compound of Formula (I), wherein $R_{3a}$ is $C_{1-4}$alkyl selected from methyl, ethyl, isopropyl, and tert-butyl.

Another aspect includes a compound of Formula (I), wherein $R_{3a}$ is $C_{1-6}$alkoxy selected from methoxy, ethoxy, propoxy, isopropoxy, butoxy, sec-butoxy, iso-butoxy, tert-butoxy, pentoxy, and hexyloxy.

Another aspect includes a compound of Formula (I), wherein $R_{3a}$ methoxy.

Another aspect includes a compound of Formula (I), wherein $R_{3a}$ is amino.

Another aspect includes a compound of Formula (I), wherein $R_{3a}$ is $C_{1-6}$alkyl-amino, wherein $C_{1-6}$alkyl is selected from methyl, ethyl, propyl, isopropyl, butyl, sec-butyl, isobutyl, and tert-butyl.

Another aspect includes a compound of Formula (I), wherein $R_{3a}$ is $C_{1-6}$alkyl-amino, wherein $C_{1-6}$alkyl is methyl.

Another aspect includes a compound of Formula (I), wherein $R_{3a}$ is deutero-$C_{1-6}$alkyl-amino, wherein $C_{1-6}$alkyl is selected from methyl, ethyl, propyl, isopropyl, butyl, sec-butyl, isobutyl, and tert-butyl partially or completely substituted with one or more deuterium atoms where allowed by available valences.

Another aspect includes a compound of Formula (I), wherein $R_{3a}$ is deutero-$C_{1-6}$alkyl-amino, wherein $C_{1-6}$alkyl is methyl substituted three deuterium atoms.

Another aspect includes a compound of Formula (I), wherein $R_{3a}$ is $(C_{1-6}$alkyl$)_2$-amino, wherein $C_{1-6}$alkyl is selected from methyl, ethyl, propyl, isopropyl, butyl, sec-butyl, isobutyl, and tert-butyl.

Another aspect includes a compound of Formula (I), wherein $R_{3a}$ is $(C_{1-6}$alkyl$)_2$-amino, wherein $C_{1-6}$alkyl is methyl.

One aspect includes a compound of Formula (I), wherein $R_4$ is hydrogen, $C_{1-6}$alkyl, or phenyl, wherein $C_{1-6}$alkyl or phenyl are optionally substituted with one, two, three, or four independently selected $R_{4a}$ substituents.

Another aspect includes a compound of Formula (I), wherein $R_4$ is hydrogen.

Another aspect includes a compound of Formula (I), wherein $R_4$ is $C_{1-6}$alkyl selected from methyl, ethyl, propyl, isopropyl, butyl, sec-butyl, isobutyl, tert-butyl, pentyl, isopentyl, hexyl, and isohexyl, optionally substituted with one, two, three, or four independently selected $R_{4a}$ substituents.

Another aspect includes a compound of Formula (I), wherein $R_4$ is $C_{1-6}$alkyl selected from methyl and ethyl, optionally substituted with one, two, three, or four independently selected $R_{4a}$ substituents.

Another aspect includes a compound of Formula (I), wherein $R_4$ is phenyl, optionally substituted with one, two, three, or four independently selected $R_{4a}$ substituents.

One aspect includes a compound of Formula (I), wherein $R_{4a}$ is cyano, halo, hydroxy, $C_{1-6}$alkyl, halo-$C_{1-6}$alkyl, or $C_{1-6}$alkoxy.

Another aspect includes a compound of Formula (I), wherein $R_{4a}$ is $C_{1-6}$alkoxy.

Another aspect includes a compound of Formula (I), wherein $R_{4a}$ is $C_{1-6}$alkoxy selected from methoxy, ethoxy, propoxy, isopropoxy, butoxy, sec-butoxy, iso-butoxy, tert-butoxy, pentoxy, and hexyloxy.

Another aspect includes a compound of Formula (I), wherein $R_{4a}$ is methoxy.

One aspect includes a compound of Formula (I), wherein $R_5$ is is hydrogen, halo, or $C_{1-6}$alkyl.

One aspect includes a compound of Formula (I), wherein $R_5$ is hydrogen, halo, or $C_{1-6}$alkyl.

Another aspect includes a compound of Formula (I), wherein $R_5$ is halo.

Another aspect includes a compound of Formula (I), wherein $R_5$ is halo selected from fluoro, chloro, bromo, and iodo.

Another aspect includes a compound of Formula (I), wherein $R_5$ is chloro or bromo.

Another aspect includes a compound of Formula (I), wherein $R_5$ is chloro.

Another aspect includes a compound of Formula (I), wherein $R_5$ is bromo.

One aspect of the compound of Formula (I) or a form thereof includes a compound selected from the group consisting of:

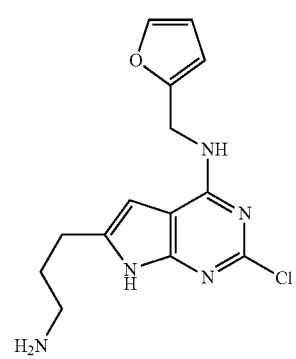

1

2
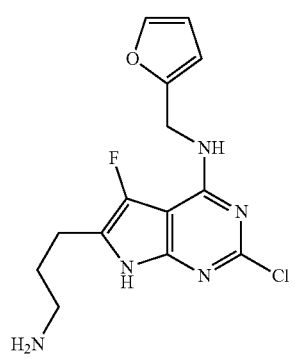
3
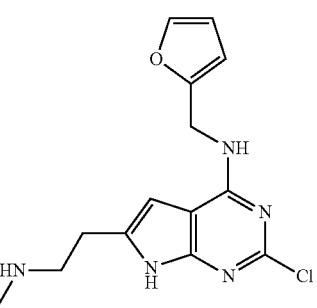
4
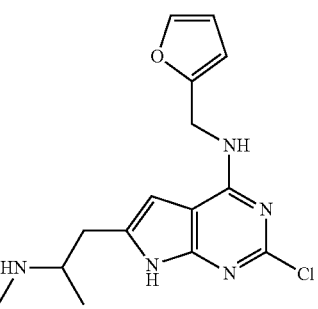
5
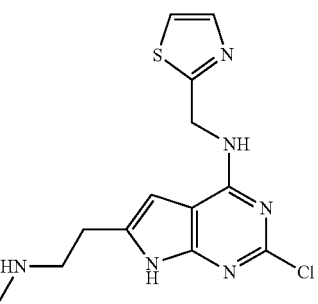
6
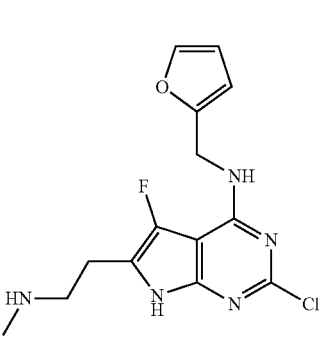
7
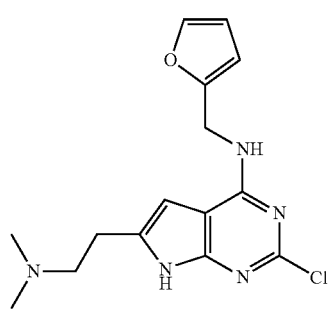
8
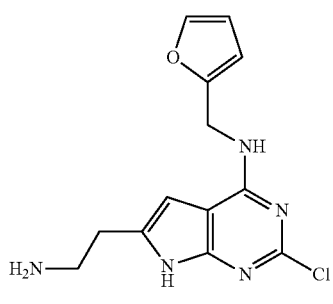
9
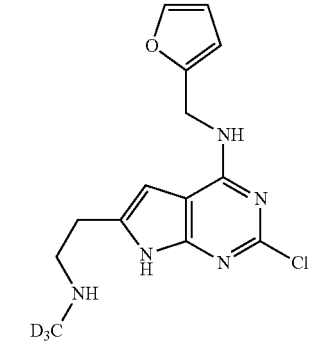
10
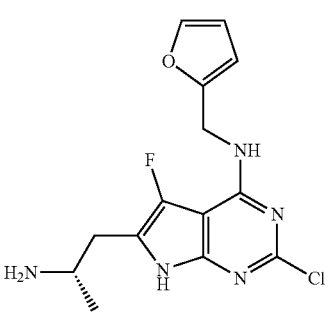
11

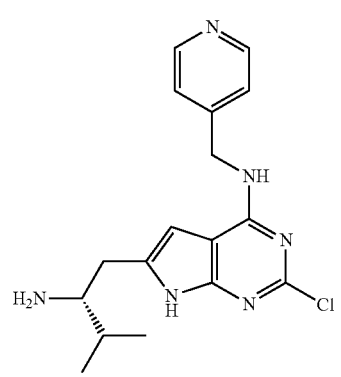
12
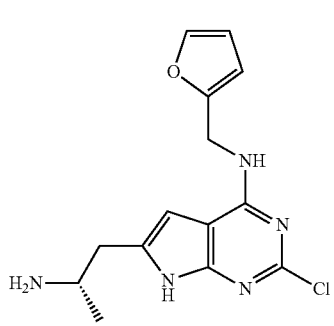
16
13
17
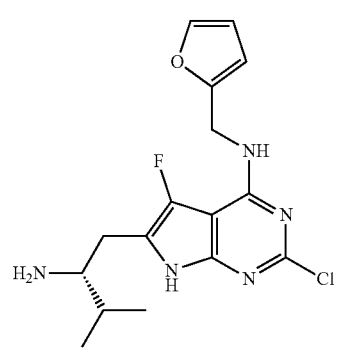
18
14
19
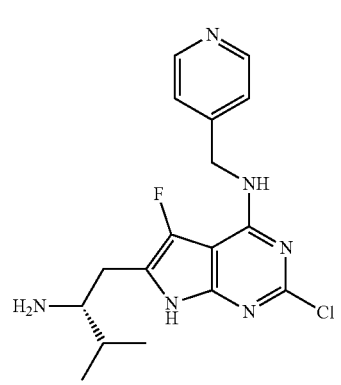
15
20

21
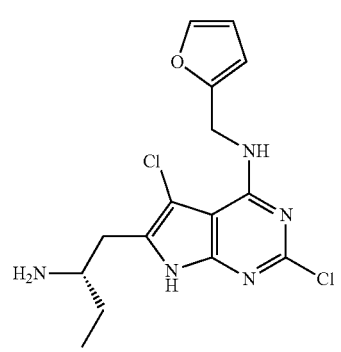
22
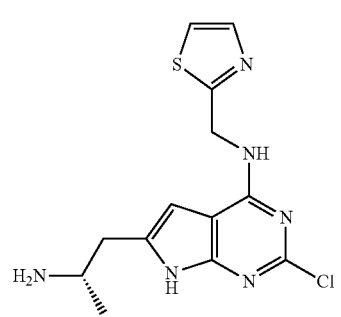
23
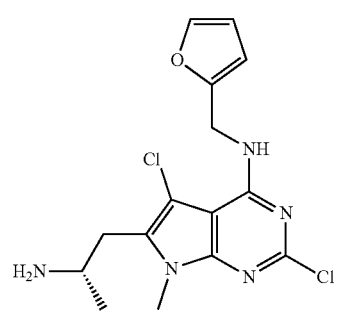
24
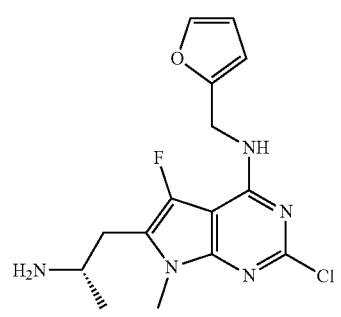
25
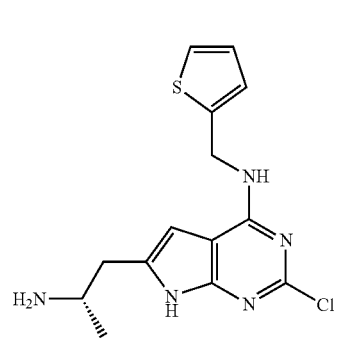
26
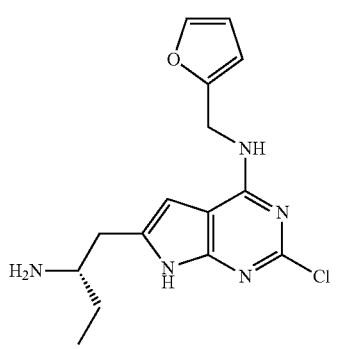
27
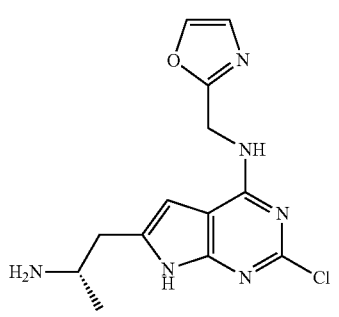
28
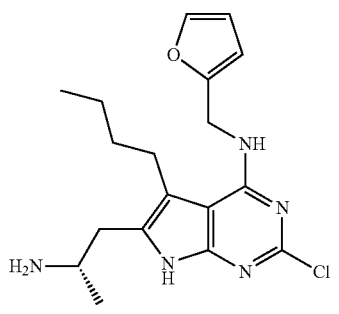
29
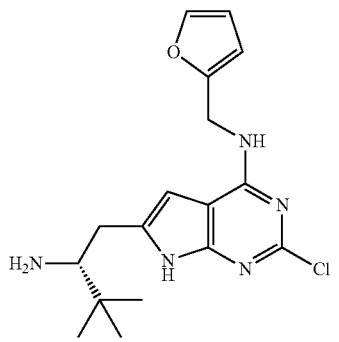
30
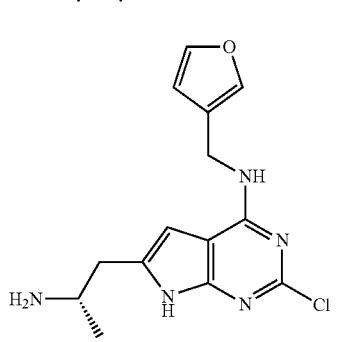

-continued
31
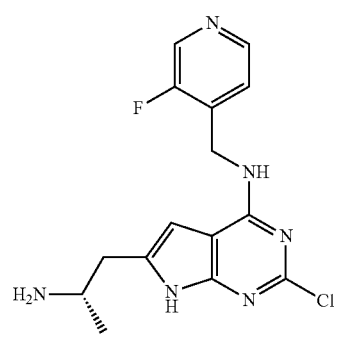
32
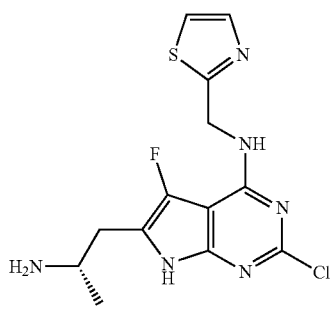
33
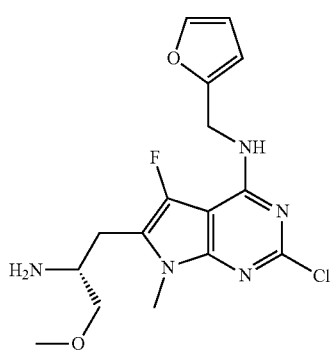
34
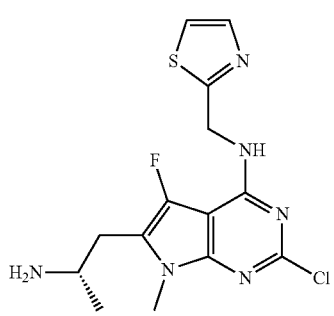
35
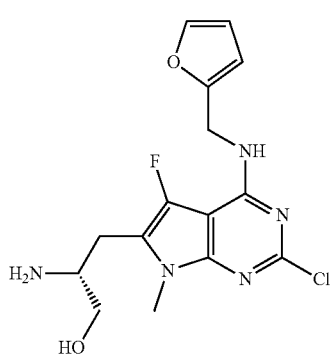
-continued
36
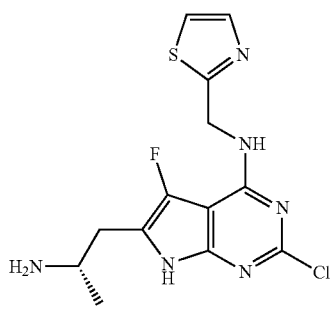
37
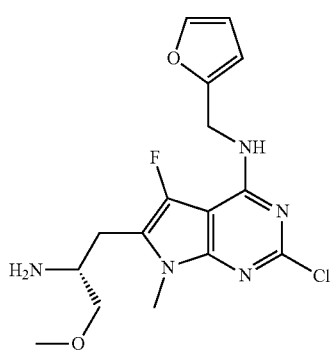
38
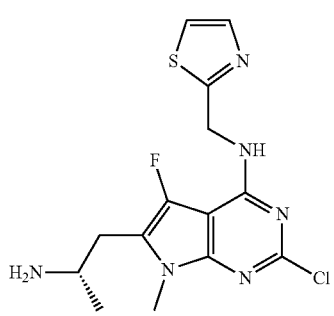
39
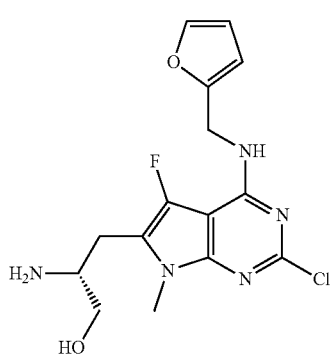
40
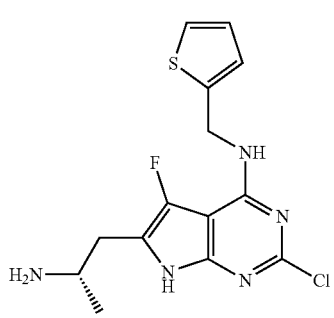

| | |
|---|---|
| 41 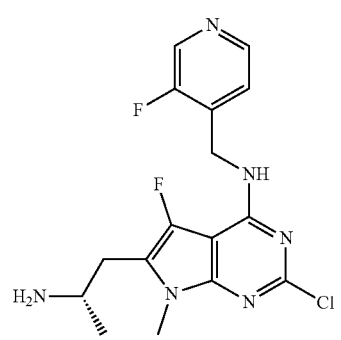 | 45 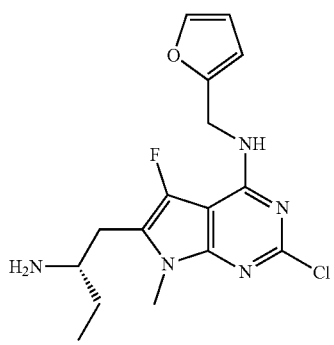 |
| 42 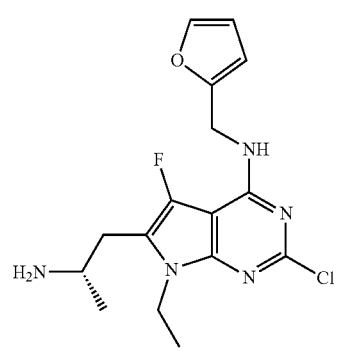 | 46 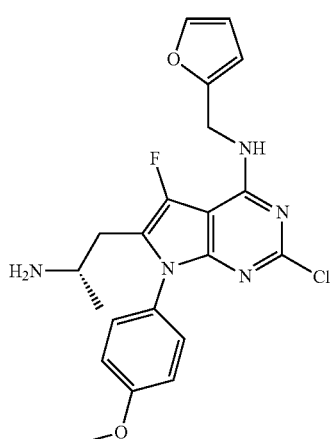 |
| 43 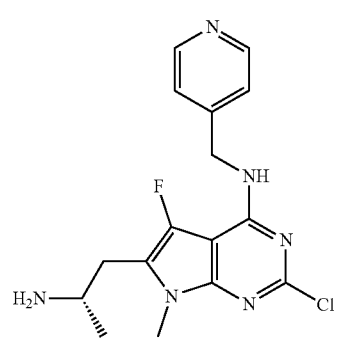 | 47 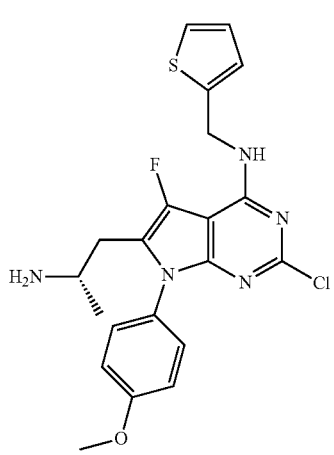 |
| 44 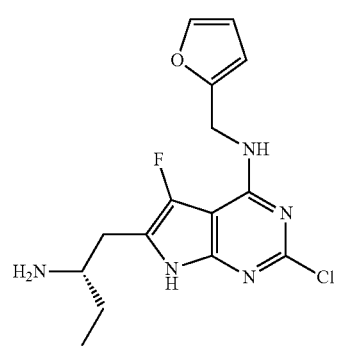 | 48 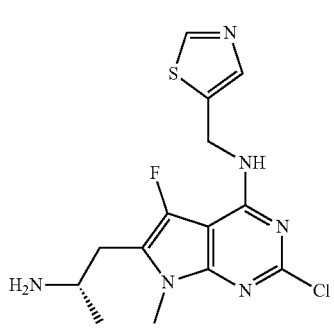 |

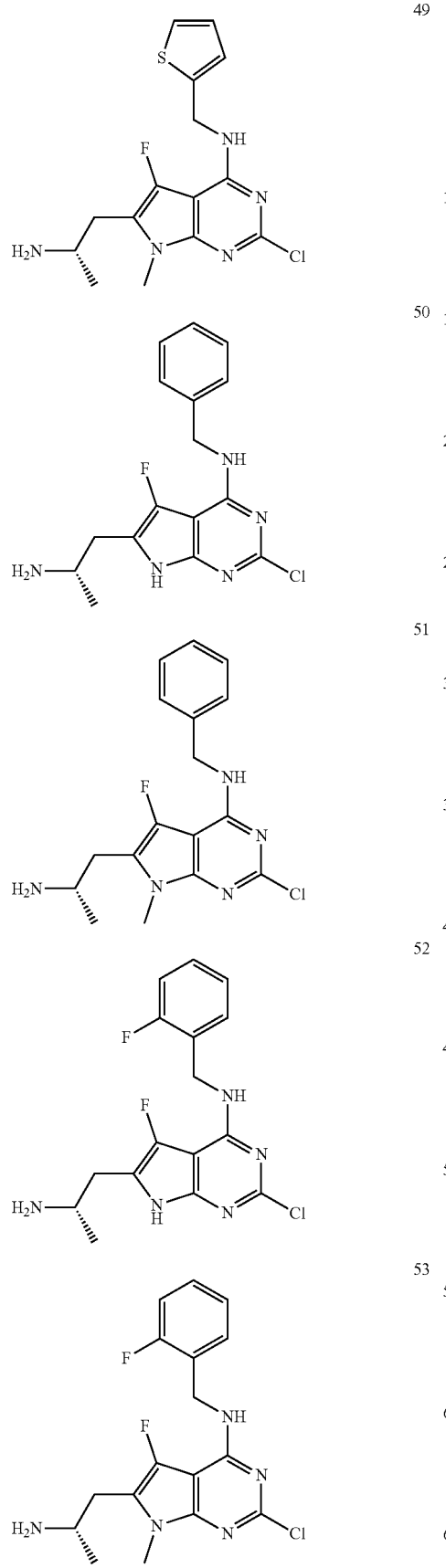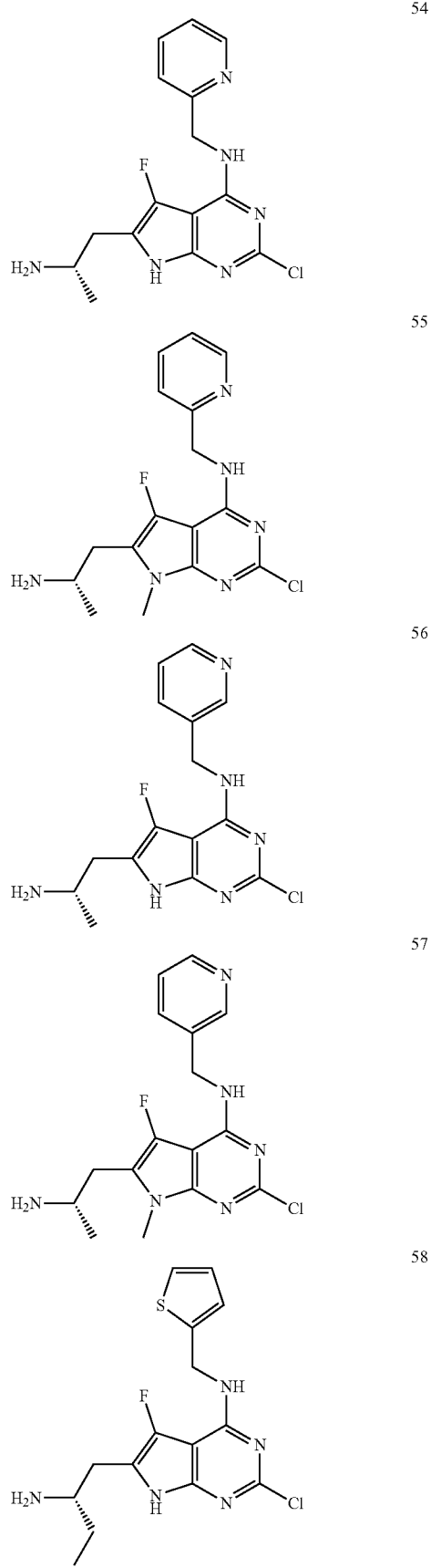

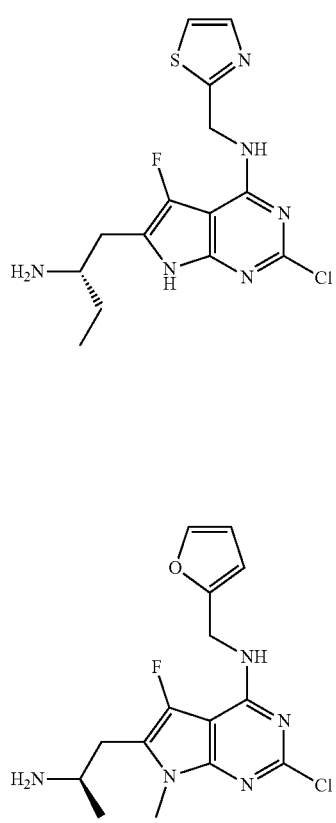

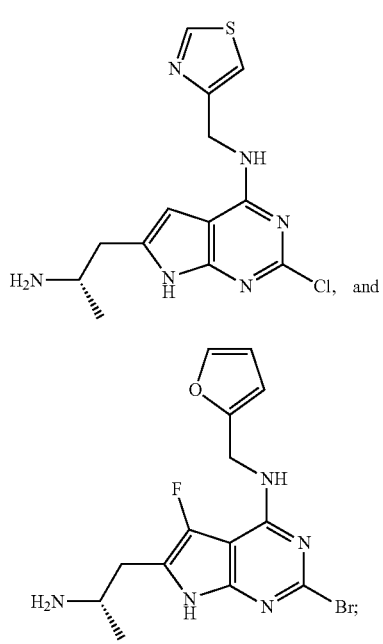

wherein the form of the compound is selected from the group consisting of a salt, hydrate, solvate, and tautomer form thereof.

An aspect the compound of Formula (I) or a form thereof (wherein compound number (#0) indicates that the salt form was isolated) includes a compound selected from the group consisting of:

| Cpd | Name |
|---|---|
| 1[1] | 6-(3-aminopropyl)-2-chloro-N-[(furan-2-yl)methyl]-7H-pyrrolo[2,3-d]pyrimidin-4-amine |
| 2[1] | 6-(3-aminopropyl)-2-chloro-5-fluoro-N-[(furan-2-yl)methyl]-7H-pyrrolo[2,3-d]pyrimidin-4-amine |
| 3[1] | 2-chloro-N-[(furan-2-yl)methyl]-6-[2-(methylamino)ethyl]-7H-pyrrolo[2,3-d]pyrimidin-4-amine |
| 4[1] | 2-chloro-N-[(furan-2-yl)methyl]-6-[2-(methylamino)propyl]-7H-pyrrolo[2,3-d]pyrimidin-4-amine |
| 5[1] | 2-chloro-6-[2-(methylamino)ethyl]-N-[(1,3-thiazol-2-yl)methyl]-7H-pyrrolo[2,3-d]pyrimidin-4-amine |
| 6[1] | 2-chloro-5-fluoro-N-[(furan-2-yl)methyl]-6-[2-(methylamino)ethyl]-7H-pyrrolo[2,3-d]pyrimidin-4-amine |
| 7 | 2-chloro-6-[2-(dimethylamino)ethyl]-N-[(furan-2-yl)methyl]-7H-pyrrolo[2,3-d]pyrimidin-4-amine |
| 8[1] | 6-(2-aminoethyl)-2-chloro-N-[(furan-2-yl)methyl]-7H-pyrrolo[2,3-d]pyrimidin-4-amine |
| 9[1] | 2-chloro-N-[(furan-2-yl)methyl]-6-{2-[($^{2}H_3$)methylamino]ethyl}-7H-pyrrolo[2,3-d]pyrimidin-4-amine |
| 10[1] | 6-[(2S)-2-aminopropyl]-2-chloro-5-fluoro-N-[(furan-2-yl)methyl]-7H-pyrrolo[2,3-d]pyrimidin-4-amine |
| 11[1] | 6-[(2R)-2-amino-3-methylbutyl]-2-chloro-N-[(furan-2-yl)methyl]-7H-pyrrolo[2,3-d]pyrimidin-4-amine |
| 12[1] | 6-[(2R)-2-amino-3-methylbutyl]-2-chloro-N-[(pyridin-4-yl)methyl]-7H-pyrrolo[2,3-d]pyrimidin-4-amine |
| 13[1] | 6-[(2S)-2-aminopropyl]-2,5-dichloro-N-[(furan-2-yl)methyl]-7H-pyrrolo[2,3-d]pyrimidin-4-amine |
| 14[1] | 6-[(2R)-2-amino-3-methylbutyl]-2-chloro-5-fluoro-N-[(furan-2-yl)methyl]-7H-pyrrolo[2,3-d]pyrimidin-4-amine |
| 15[1] | 6-[(2R)-2-amino-3-methylbutyl]-2-chloro-5-fluoro-N-[(pyridin-4-yl)methyl]-7H-pyrrolo[2,3-d]pyrimidin-4-amine |
| 16 | 6-[(2S)-2-aminopropyl]-2-chloro-N-[(furan-2-yl)methyl]-7H-pyrrolo[2,3-d]pyrimidin-4-amine |
| 17[1] | 2,5-dichloro-N-[(furan-2-yl)methyl]-6-[2-(methylamino)ethyl]-7H-pyrrolo[2,3-d]pyrimidin-4-amine |
| 18[1] | 5-bromo-2-chloro-N(furan-2-yl)methyl]-6-[2-(methylamino)ethyl]-7H-pyrrolo[2,3-d]pyrimidin-4-amine |

-continued

| Cpd | Name |
|---|---|
| 19[1] | 6-[(2S)-2-aminopropyl]-5-bromo-2-chloro-N-[(furan-2-yl)methyl]-7H-pyrrolo[2,3-d]pyrimidin-4-amine |
| 20 | 6-[(2S)-2-aminopropyl]-2-chloro-N-[(pyridin-4-yl)methyl]-7H-pyrrolo[2,3-d]pyrimidin-4-amine |
| 21[1] | 6-[(2S)-2-aminobutyl]-2,5-dichloro-N-[(furan-2-yl)methyl]-7H-pyrrolo[2,3-d]pyrimidin-4-amine |
| 22[1] | 6-[(2S)-2-aminopropyl]-2-chloro-N-[(1,3-thiazol-2-yl)methyl]-7H-pyrrolo[2,3-d]pyrimidin-4-amine |
| 23[1] | 6-[(2S)-2-aminopropyl]-2,5-dichloro-N-[(furan-2-yl)methyl]-7-methyl-7H-pyrrolo[2,3-d]pyrimidin-4-amine |
| 24[1] | 6-[(2S)-2-aminopropyl]-2-chloro-5-fluoro-N-[(furan-2-yl)methyl]-7-methyl-7H-pyrrolo[2,3-d]pyrimidin-4-amine |
| 25[1] | 6-[(2S)-2-aminopropyl]-2-chloro-N-[(thiophen-2-yl)methyl]-7H-pyrrolo[2,3-d]pyrimidin-4-amine |
| 26 | 6-[(2S)-2-aminobutyl]-2-chloro-N-[(furan-2-yl)methyl]-7H-pyrrolo[2,3-d]pyrimidin-4-amine |
| 27[1] | 6-[(2S)-2-aminopropyl]-2-chloro-N-[(1,3-oxazol-2-yl)methyl]-7H-pyrrolo[2,3-d]pyrimidin-4-amine |
| 28[1] | 6-[(2S)-2-aminopropyl]-5-butyl-2-chloro-N-[(furan-2-yl)methyl]-7H-pyrrolo[2,3-d]pyrimidin-4-amine |
| 29[1] | 6-[(2R)-2-amino-3,3-dimethylbutyl]-2-chloro-N-[(furan-2-yl)methyl]-7H-pyrrolo[2,3-d]pyrimidin-4-amine |
| 30[1] | 6-[(2S)-2-aminopropyl]-2-chloro-N-[(furan-3-yl)methyl]-7H-pyrrolo[2,3-d]pyrimidin-4-amine |
| 31[1] | 6-[(2S-2-aminopropyl]-2-chloro-N-[(3-fluoropyridin-4-yl)methyl]-7H-pyrrolo[2,3-d]pyrimidin-4-amine |
| 32[1] | 6-[(2R,3S)-2-amino-3-methylpentyl]-2-chloro-N-[(furan-2-yl)methyl]-7H-pyrrolo[2,3-d]pyrimidin-4-amine |
| 33[1] | 6-[(2S)-2-aminopropyl]-2-chloro-N-[(furan-2-yl)methyl]-5-methyl-7H-pyrrolo[2,3-d]pyrimidin-4-amine |
| 34[1] | 6-[(2S)-2-aminopropyl]-5-fluoro-N-[(furan-2-yl)methyl]-2-methyl-7H-pyrrolo[2,3-d]pyrimidin-4-amine |
| 35[1] | 6-[(2S)-2-aminopropyl]-2-chloro-N-[(furan-2-yl)methyl]-5,7-dimethyl-7H-pyrrolo[2,3-d]pyrimidin-4-amine |
| 36[1] | 6-[(2S)-2-aminopropyl]-2-chloro-5-fluoro-N-[(1,3-thiazol-2-yl)methyl]-7H-pyrrolo[2,3-d]pyrimidin-4-amine |
| 37[1] | 6-[(2R)-2-amino-3-methoxypropyl]-2-chloro-5-fluoro-N-[(furan-2-yl)methyl]-7-methyl-7H-pyrrolo[2,3-d]pyrimidin-4-amine |
| 38[1] | 6-[(2S)-2-aminopropyl]-2-chloro-5-fluoro-7-methyl-N-[(1,3-thiazol-2-yl)methyl]-7H-pyrrolo[2,3-d]pyrimidin-4-amine |
| 39[1] | (2R)-2-amino-3-(2-chloro-5-fluoro-4-{[(furan-2-yl)methyl]amino}-7-methyl-7H-pyrrolo[2,3-d]pyrimidin-6-yl)propan-1-ol |
| 40[1] | 6-[(2S)-2-aminopropyl]-2-chloro-5-fluoro-N-[(thiophen-2-yl)methyl]-7H-pyrrolo[2,3-d]pyrimidin-4-amine |
| 41[1] | 6-[(2S)-2-aminopropyl]-2-chloro-5-fluoro-N-[(3-fluoropyridin-4-yl)methyl]-7-methyl-7H-pyrrolo[2,3-d]pyrimidin-4-amine |
| 42[1] | 6-[(2S)-2-aminopropyl]-2-chloro-7-ethyl-5-fluoro-N-[(furan-2-yl)methyl]-7H-pyrrolo[2,3-d]pyrimidin-4-amine |
| 43[1] | 6-[(2S)-2-aminopropyl]-2-chloro-5-fluoro-7-methyl-N-[(pyridin-4-yl)methyl]-7H-pyrrolo[2,3-d]pyrimidin-4-amine |
| 44[1] | 6-[(2S)-2-aminobutyl]-2-chloro-5-fluoro-N-[(furan-2-yl)methyl]-7H-pyrrolo[2,3-d]pyrimidin-4-amine |
| 45[1] | 6-[(2S)-2-aminobutyl]-2-chloro-5-fluoro-N-[(furan-2-yl)methyl]-7-methyl-7H-pyrrolo[2,3-d]pyrimidin-4-amine |
| 46[1] | 6-[(2S)-2-aminopropyl]-2-chloro-5-fluoro-N-[(furan-2-yl)methyl]-7-(4-methoxyphenyl)-7H-pyrrolo[2,3-d]pyrimidin-4-amine |
| 47[1] | 6-[(2S)-2-aminopropyl]-2-chloro-5-fluoro-7-(4-methoxyphenyl)-N-[(thiophen-2-yl)methyl]-7H-pyrrolo[2,3-d]pyrimidin-4-amine |
| 48[1] | 6-[(2S)-2-aminopropyl]-2-chloro-5-fluoro-7-methyl-N-[(1,3-thiazol-5-yl)methyl]-7H-pyrrolo[2,3-d]pyrimidin-4-amine |
| 49[1] | 6-[(2S)-2-aminopropyl]-2-chloro-5-fluoro-7-methyl-N(thiophen-2-yl)methyl]-7H-pyrrolo[2,3-d]pyrimidin-4-amine |
| 50[1] | 6-[(2S)-2-aminopropyl]-N-benzyl-2-chloro-5-fluoro-7H-pyrrolo[2,3-d]pyrimidin-4-amine |
| 51[1] | 6-[(2S)-2-aminopropyl]-N-benzyl-2-chloro-5-fluoro-7-methyl-7H-pyrrolo[2,3-d]pyrimidin-4-amine |
| 52[1] | 6-[(2S)-2-aminopropyl]-2-chloro-5-fluoro-N-[(2-fluorophenyl)methyl]-7H-pyrrolo[2,3-d]pyrimidin-4-amine |
| 53[1] | 6-[(2S)-2-aminopropyl]-2-chloro-5-fluoro-N-[(2-fluorophenyl)methyl]-7-methyl-7H-pyrrolo[2,3-d]pyrimidin-4-amine |
| 54[1] | 6-[(2S)-2-aminopropyl]-2-chloro-5-fluoro-N-[(pyridin-2-yl)methyl]-7H-pyrrolo[2,3-d]pyrimidin-4-amine |
| 55[1] | 6-[(2S)-2-aminopropyl]-2-chloro-5-fluoro-7-methyl-N-[(pyridin-2-yl)methyl]-7H-pyrrolo[2,3-d]pyrimidin-4-amine |
| 56[1] | 6-[(2S)-2-aminopropyl]-2-chloro-5-fluoro-N-[(pyridin-3-yl)methyl]-7H-pyrrolo[2,3-d]pyrimidin-4-amine |

| Cpd | Name |
|---|---|
| 57[1] | 6-[(2S)-2-aminopropyl]-2-chloro-5-fluoro-7-methyl-N-[(pyridin-3-yl)methyl]-7H-pyrrolo[2,3-d]pyrimidin-4-amine |
| 58[1] | 6-[(2S)-2-aminobutyl]-2-chloro-5-fluoro-N-[(thiophen-2-yl)methyl]-7H-pyrrolo[2,3-d]pyrimidin-4-amine |
| 59[1] | 6-[(2S)-2-aminobutyl]-2-chloro-5-fluoro-N-[(1,3-thiazol-2-yl)methyl]-7H-pyrrolo[2,3-d]pyrimidin-4-amine |
| 60[1] | 6-[(2R)-2-aminopropyl]-2-chloro-5-fluoro-N-[(furan-2-yl)methyl]-7-methyl-7H-pyrrolo[2,3-d]pyrimidin-4-amine |
| 61 | 6-[(2S)-2-aminopropyl]-2-chloro-N-[(1,3-thiazol-4-yl)methyl]-7H-pyrrolo[2,3-d]pyrimidin-4-amine, and |
| 62 | 6-[(2S)-2-aminopropyl]-2-bromo-5-fluoro-N-[(furan-2-yl)methyl]-7H-pyrrolo[2,3-d]pyrimidin-4-amine; | wherein the form of the compound is selected from the group consisting of a salt, hydrate, solvate, and tautomer form thereof.

Another aspect of the compound of Formula (I) or a form thereof is a compound salt selected from the group consisting of:

| Cpd | Name |
|---|---|
| 1 | 6-(3-aminopropyl)-2-chloro-N-[(furan-2-yl)methyl]-7H-pyrrolo[2,3-d]pyrimidin-4-amine hydrochloride |
| 2 | 6-(3-aminopropyl)-2-chloro-5-fluoro-N-[(furan-2-yl)methyl]-7H-pyrrolo[2,3-d]pyrimidin-4-amine hydrochloride |
| 3 | 2-chloro-N-[(furan-2-yl)methyl]-6-[2-(methylamino)ethyl]-7H-pyrrolo[2,3-d]pyrimidin-4-amine hydrochloride |
| 4 | 2-chloro-N-[(furan-2-yl)methyl]-6-[2-(methylamino)propyl]-7H-pyrrolo[2,3-d]pyrimidin-4-amine hydrochloride |
| 5 | 2-chloro-6-[2-(methylamino)ethyl]-N-[(1,3-thiazol-2-yl)methyl]-7H-pyrrolo[2,3-d]pyrimidin-4-amine hydrochloride |
| 6 | 2-chloro-5-fluoro-N-[(furan-2-yl)methyl]-6-[2-(methylamino)ethyl]-7H-pyrrolo[2,3-d]pyrimidin-4-amine hydrochloride |
| 8 | 6-(2-aminoethyl)-2-chloro-N-[(furan-2-yl)methyl]-7H-pyrrolo[2,3-d]pyrimidin-4-amine hydrochloride |
| 9 | 2-chloro-N-[(furan-2-yl)methyl]-6-{2-[($^2$H$_3$)methylamino]ethyl}-7H-pyrrolo[2,3-d]pyrimidin-4-amine hydrochloride |
| 10 | 6-[(2S)-2-aminopropyl]-2-chloro-5-fluoro-N-[(furan-2-yl)methyl]-7H-pyrrolo[2,3-d]pyrimidin-4-amine hydrochloride |
| 11 | 6-[(2R)-2-amino-3-methylbutyl]-2-chloro-N-[(furan-2-yl)methyl]-7H-pyrrolo[2,3-d]pyrimidin-4-amine hydrochloride |
| 12 | 6-[(2R)-2-amino-3-methylbutyl]-2-chloro-N-[(pyridin-4-yl)methyl]-7H-pyrrolo[2,3-d]pyrimidin-4-amine dihydrochloride |
| 13 | 6-[(2S)-2-aminopropyl]-2,5-dichloro-N-[(furan-2-yl)methyl]-7H-pyrrolo[2,3-d]pyrimidin-4-amine hydrochloride |
| 14 | 6-[(2R)-2-amino-3-methylbutyl]-2-chloro-5-fluoro-N-[(furan-2-yl)methyl]-7H-pyrrolo[2,3-d]pyrimidin-4-amine hydrochloride |
| 15 | 6-[(2R)-2-amino-3-methylbutyl]-2-chloro-5-fluoro-N-[(pyridin-4-yl)methyl]-7H-pyrrolo[2,3-d]pyrimidin-4-amine dihydrochloride |
| 17 | 2,5-dichloro-N-[(furan-2-yl)methyl]-6-[2-(methylamino)ethyl]-7H-pyrrolo[2,3-d]pyrimidin-4-amine hydrochloride |
| 18 | 5-bromo-2-chloro-N-(furan-2-yl)methyl]-6-[2-(methylamino)ethyl]-7H-pyrrolo[2,3-d]pyrimidin-4-amine hydrochloride |
| 19 | 6-[(2S)-2-aminopropyl]-5-bromo-2-chloro-N-[(furan-2-yl)methyl]-7H-pyrrolo[2,3-d]pyrimidin-4-amine hydrochloride |
| 21 | 6-[(2S)-2-aminobutyl]-2,5-dichloro-N-[(furan-2-yl)methyl]-7H-pyrrolo[2,3-d]pyrimidin-4-amine hydrochloride |
| 22 | 6-[(2S)-2-aminopropyl]-2-chloro-N-[(1,3-thiazol-2-yl)methyl]-7H-pyrrolo[2,3-d]pyrimidin-4-amine hydrochloride |
| 23 | 6-[(2S)-2-aminopropyl]-2,5-dichloro-N-[(furan-2-yl)methyl]-7-methyl-7H-pyrrolo[2,3-d]pyrimidin-4-amine hydrochloride |
| 24 | 6-[(2S)-2-aminopropyl]-2-chloro-5-fluoro-N-[(furan-2-yl)methyl]-7-methyl-7H-pyrrolo[2,3-d]pyrimidin-4-amine hydrochloride |
| 25 | 6-[(2S)-2-aminopropyl]-2-chloro-N-[(thiophen-2-yl)methyl]-7H-pyrrolo[2,3-d]pyrimidin-4-amine hydrochloride |
| 27 | 6-[(2S)-2-aminopropyl]-2-chloro-N-[(1,3-oxazol-2-yl)methyl]-7H-pyrrolo[2,3-d]pyrimidin-4-amine hydrochloride |
| 28 | 6-[(2S)-2-aminopropyl]-5-butyl-2-chloro-N-[(furan-2-yl)methyl]-7H-pyrrolo[2,3-d]pyrimidin-4-amine hydrochloride |
| 29 | 6-[(2R)-2-amino-3,3-dimethylbutyl]-2-chloro-N-[(furan-2-yl)methyl]-7H-pyrrolo[2,3-d]pyrimidin-4-amine hydrochloride |
| 30 | 6-[(2S)-2-aminopropyl]-2-chloro-N-[(furan-3-yl)methyl]-7H-pyrrolo[2,3-d]pyrimidin-4-amine hydrochloride |
| 31 | 6-[(2S)-2-aminopropyl]-2-chloro-N-[(3-fluoropyridin-4-yl)methyl]-7H-pyrrolo[2,3-d]pyrimidin-4-amine dihydrochloride |

| Cpd | Name |
|---|---|
| 32 | 6-[(2R,3S)-2-amino-3-methylpentyl]-2-chloro-N-[(furan-2-yl)methyl]-7H-pyrrolo[2,3-d]pyrimidin-4-amine hydrochloride |
| 33 | 6-[(2S)-2-aminopropyl]-2-chloro-N-[(furan-2-yl)methyl]-5-methyl-7H-pyrrolo[2,3-d]pyrimidin-4-amine hydrochloride |
| 34 | 6-[(2S)-2-aminopropyl]-5-fluoro-N-[(furan-2-yl)methyl]-2-methyl-7H-pyrrolo[2,3-d]pyrimidin-4-amine hydrochloride |
| 35 | 6-[(2S)-2-aminopropyl]-2-chloro-N-[(furan-2-yl)methyl]-5,7-dimethyl-7H-pyrrolo[2,3-d]pyrimidin-4-amine hydrochloride |
| 36 | 6-[(2S)-2-aminopropyl]-2-chloro-5-fluoro-N-[(1,3-thiazol-2-yl)methyl]-7H-pyrrolo[2,3-d]pyrimidin-4-amine hydrochloride |
| 37 | 6-[(2R)-2-amino-3-methoxypropyl]-2-chloro-5-fluoro-N-[(furan-2-yl)methyl]-7-methyl-7H-pyrrolo[2,3-d]pyrimidin-4-amine hydrochloride |
| 38 | 6-[(2S)-2-aminopropyl]-2-chloro-5-fluoro-7-methyl-N-[(1,3-thiazol-2-yl)methyl]-7H-pyrrolo[2,3-d]pyrimidin-4-amine hydrochloride |
| 39 | (2R)-2-amino-3-(2-chloro-5-fluoro-4-{[(furan-2-yl)methyl]amino}-7-methyl-7H-pyrrolo[2,3-d]pyrimidin-6-yl)propan-1-ol hydrochloride |
| 40 | 6-[(2S)-2-aminopropyl]-2-chloro-5-fluoro-N-[(thiophen-2-yl)methyl]-7H-pyrrolo[2,3-d]pyrimidin-4-amine hydrochloride |
| 41 | 6-[(2S)-2-aminopropyl]-2-chloro-5-fluoro-N-[(3-fluoropyridin-4-yl)methyl]-7-methyl-7H-pyrrolo[2,3-d]pyrimidin-4-amine dihydrochloride |
| 42 | 6-[(2S)-2-aminopropyl]-2-chloro-7-ethyl-5-fluoro-N-[(furan-2-yl)methyl]-7H-pyrrolo[2,3-d]pyrimidin-4-amine hydrochloride |
| 43 | 6-[(2S)-2-aminopropyl]-2-chloro-5-fluoro-7-methyl-N-[(pyridin-4-yl)methyl]-7H-pyrrolo[2,3-d]pyrimidin-4-amine dihydrochloride |
| 44 | 6-[(2S)-2-aminobutyl]-2-chloro-5-fluoro-N-[(furan-2-yl)methyl]-7H-pyrrolo[2,3-d]pyrimidin-4-amine hydrochloride |
| 45 | 6-[(2S)-2-aminobutyl]-2-chloro-5-fluoro-N-[(furan-2-yl)methyl]-7-methyl-7H-pyrrolo[2,3-d]pyrimidin-4-amine hydrochloride |
| 46 | 6-[(2S)-2-aminopropyl]-2-chloro-5-fluoro-N-[(furan-2-yl)methyl]-7-(4-methoxyphenyl)-7H-pyrrolo[2,3-d]pyrimidin-4-amine hydrochloride |
| 47 | 6-[(2S)-2-aminopropyl]-2-chloro-5-fluoro-7-(4-methoxyphenyl)-N-[(thiophen-2-yl)methyl]-7H-pyrrolo[2,3-d]pyrimidin-4-amine hydrochloride |
| 48 | 6-[(2S)-2-aminopropyl]-2-chloro-5-fluoro-7-methyl-N-[(1,3-thiazol-5-yl)methyl]-7H-pyrrolo[2,3-d]pyrimidin-4-amine dihydrochloride |
| 49 | 6-[(2S)-2-aminopropyl]-2-chloro-5-fluoro-7-methyl-N-[(thiophen-2-yl)methyl]-7H-pyrrolo[2,3-d]pyrimidin-4-amine hydrochloride |
| 50 | 6-[(2S)-2-aminopropyl]-N-benzyl-2-chloro-5-fluoro-7H-pyrrolo[2,3-d]pyrimidin-4-amine hydrochloride |
| 51 | 6-[(2S)-2-aminopropyl]-N-benzyl-2-chloro-5-fluoro-7-methyl-7H-pyrrolo[2,3-d]pyrimidin-4-amine hydrochloride |
| 52 | 6-[(2S)-2-aminopropyl]-2-chloro-5-fluoro-N-[(2-fluorophenyl)methyl]-7H-pyrrolo[2,3-d]pyrimidin-4-amine hydrochloride |
| 53 | 6-[(2S)-2-aminopropyl]-2-chloro-5-fluoro-N-[(2-fluorophenyl)methyl]-7-methyl-7H-pyrrolo[2,3-d]pyrimidin-4-amine hydrochloride |
| 54 | 6-[(2S)-2-aminopropyl]-2-chloro-5-fluoro-N-[(pyridin-2-yl)methyl]-7H-pyrrolo[2,3-d]pyrimidin-4-amine dihydrochloride |
| 55 | 6-[(2S)-2-aminopropyl]-2-chloro-5-fluoro-7-methyl-N-[(pyridin-2-yl)methyl]-7H-pyrrolo[2,3-d]pyrimidin-4-amine dihydrochloride |
| 56 | 6-[(2S)-2-aminopropyl]-2-chloro-5-fluoro-N-[(pyridin-3-yl)methyl]-7H-pyrrolo[2,3-d]pyrimidin-4-amine dihydrochloride |
| 57 | 6-[(2S)-2-aminopropyl]-2-chloro-5-fluoro-7-methyl-N-[(pyridin-3-yl)methyl]-7H-pyrrolo[2,3-d]pyrimidin-4-amine dihydrochloride |
| 58 | 6-[(2S)-2-aminobutyl]-2-chloro-5-fluoro-N-[(thiophen-2-yl)methyl]-7H-pyrrolo[2,3-d]pyrimidin-4-amine hydrochloride |
| 59 | 6-[(2S)-2-aminobutyl]-2-chloro-5-fluoro-N-[(1,3-thiazol-2-yl)methyl]-7H-pyrrolo[2,3-d]pyrimidin-4-amine hydrochloride, and |
| 60 | 6-[(2R)-2-aminopropyl]-2-chloro-5-fluoro-N-[(furan-2-yl)methyl]-7-methyl-7H-pyrrolo[2,3-d]pyrimidin-4-amine hydrochloride; | wherein the form of the compound salt is selected from the group consisting of hydrate, solvate, and tautomer form thereof.

The present application further provides a pharmaceutical composition comprising a compound provided herein, or a pharmaceutically acceptable salt thereof, and at least one pharmaceutically acceptable carrier.

The present application further provides a method of treating familial dysautonomia, a disease of the central and peripheral nervous system associated with one or more pre-mRNA splicing defects in a subject in need thereof, the method comprising administering to the subject a therapeutically effective amount of a compound provided herein, or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used.

The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Chemical Definitions

The chemical terms used above and throughout the description herein, unless specifically defined otherwise, shall be understood by one of ordinary skill in the art to have the following indicated meanings.

As used herein, the term "$C_{1-6}$alkyl" generally refers to saturated hydrocarbon radicals having from one to six carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl, n-pentyl (also referred to as pentyl or pentanyl), n-hexyl (also referred to as hexyl or hexanyl) and the like. In certain aspects, $C_{1-6}$alkyl includes, but is not limited to, $C_{1-6}$alkyl, $C_{2-6}$alkyl, $C_{1-4}$alkyl, $C_{2-4}$alkyl and the like. A $C_{1-6}$alkyl radical is optionally substituted with substituent species as described herein where allowed by available valences.

As used herein, the terms "deutero" or "deutero-$C_{1-6}$alkyl" generally refer to saturated hydrocarbon radicals having from one to six carbon atoms in a straight or branched chain configuration, in which one or more carbon atom members have been substituted, where allowed by structural stability, with one or more deuterium atoms, including, but not limited to, but not limited to, deutero-methyl, deutero-ethyl, deutero-propyl, deutero-butyl, deutero-pentyl, deutero-hexyl and the like. In certain aspects, deutero-$C_{1-6}$alkyl includes, but is not limited to, deutero-$C_{1-4}$alkyl and the like. A deutero-$C_{1-6}$alkyl radical is optionally substituted with substituent species as described herein where allowed by available valences.

As used herein, the term "hetero-$C_{1-6}$alkyl" generally refers to saturated hydrocarbon radicals having from one to six carbon atoms in a straight or branched chain configuration, in which one or more heteroatoms, such as an O, S or N atom, are members in the chain, including, but not limited to, but not limited to, hetero-methyl, hetero-ethyl, hetero-propyl, hetero-butyl, hetero-pentyl, hetero-hexyl and the like. In certain aspects, hetero-$C_{1-6}$alkyl includes, but is not limited to, hetero-$C_{2-6}$alkyl, hetero-$C_{1-4}$alkyl, hetero-$C_{2-4}$alkyl and the like. A hetero-$C_{1-6}$alkyl radical is optionally substituted with substituent species as described herein where allowed by available valences.

As used herein, the term "$C_{2-6}$alkenyl" generally refers to partially unsaturated hydrocarbon radicals having from two to six carbon atoms in a straight or branched chain configuration and one or more carbon-carbon double bonds therein, including, but not limited to, ethenyl (also referred to as vinyl), allyl, propenyl and the like. In certain aspects, $C_{2-6}$alkenyl includes, but is not limited to, $C_{2-4}$alkenyl, $C_{2-4}$alkenyl and the like. A $C_{2-6}$alkenyl radical is optionally substituted with substituent species as described herein where allowed by available valences.

As used herein, the term "$C_{2-6}$alkynyl" generally refers to partially unsaturated hydrocarbon radicals having from two to six carbon atoms in a straight or branched chain configuration and one or more carbon-carbon triple bonds therein, including, but not limited to, ethynyl, propynyl, butynyl and the like. In certain aspects, $C_{2-6}$alkynyl includes, but is not limited to, $C_{2-6}$alkynyl, $C_{2-4}$alkynyl and the like. A $C_{2-6}$alkynyl radical is optionally substituted with substituent species as described herein where allowed by available valences.

As used herein, the term "$C_{1-6}$alkoxy" generally refers to saturated hydrocarbon radicals having from one to six carbon atoms in a straight or branched chain configuration of the formula: —O—$C_{1-6}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In certain aspects, $C_{1-6}$alkoxy includes, but is not limited to, $C_{1-6}$alkoxy, $C_{2-6}$alkoxy, $C_{1-4}$alkoxy, $C_{2-4}$alkoxy and the like. A $C_{1-6}$alkoxy radical is optionally substituted with substituent species as described herein where allowed by available valences.

As used herein, the term "$C_{3-10}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, cyclooctyl, 1H-indanyl, indenyl, tetrahydro-naphthalenyl and the like. In certain aspects, $C_{3-10}$cycloalkyl includes, but is not limited to, $C_{3-8}$cycloalkyl, $C_{5-8}$cycloalkyl and the like. A $C_{3-10}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl, thiophenyl, pyrrolyl, pyrazolyl, imidazolyl, isoxazolyl, isothiazolyl, oxazolyl, 1,3-thiazolyl, triazolyl, oxadiazolyl, thiadiazolyl, tetrazolyl, pyridinyl, pyrimidinyl, pyrazinyl, pyridazinyl, triazinyl, indolyl, indazolyl, indolizinyl, isoindolyl, benzofuranyl, benzothiophenyl, benzoimidazolyl, 1,3-benzothiazolyl, 1,3-benzoxazolyl, purinyl, quinolinyl, isoquinolinyl, quinazolinyl, quinoxalinyl and the like. A heteroaryl radical is optionally substituted on a carbon or nitrogen atom ring member with substituent species as described herein where allowed by available valences.

In certain aspects, the nomenclature for a heteroaryl radical may differ, such as in non-limiting examples where furanyl may also be referred to as furyl, thiophenyl may also be referred to as thienyl, pyridinyl may also be referred to as pyridyl, benzothiophenyl may also be referred to as benzothiothienyl and 1,3-benzoxazolyl may also be referred to as 1,3-benzooxazolyl.

In certain other aspects, the term for a heteroaryl radical may also include other regioisomers, such as in non-limiting examples where the term pyrrolyl may also include 2H-pyrrolyl, 3H-pyrrolyl and the like, the term pyrazolyl may also include 1H-pyrazolyl and the like, the term imidazolyl may also include 1H-imidazolyl and the like, the term triazolyl may also include 1H-1,2,3-triazolyl and the like, the term oxadiazolyl may also include 1,2,4-oxadiazolyl, 1,3,4-oxadiazolyl and the like, the term tetrazolyl may also include 1H-tetrazolyl, 2H-tetrazolyl and the like, the term indolyl may also include 1H-indolyl and the like, the term indazolyl may also include 1H-indazolyl, 2H-indazolyl and the like, the term benzoimidazolyl may also include 1H-benzoimidazolyl and the term purinyl may also include 9H-purinyl and the like.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, tetrahydropyranyl, thiopyranyl, 1,3-dioxanyl, 1,3-oxazinanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl, 1,4-benzodioxanyl and the like. A heterocyclyl radical is optionally substituted on a carbon or nitrogen atom ring member with substituent species as described herein where allowed by available valences.

As used herein, the term "$C_{1-6}$alkyl-amino" refers to a radical of the formula: —NH—$C_{1-6}$alkyl.

As used herein, the term "($C_{1-6}$alkyl)$_2$-amino" refers to a radical of the formula: —N($C_{1-6}$alkyl)$_2$.

As used herein, the term "aryl-amino" refers to a radical of the formula: —NH-aryl.

As used herein, the term "heterocyclyl-amino" refers to a radical of the formula: —NH-heterocyclyl.

As used herein, the term "heteroaryl-amino" refers to a radical of the formula: —NH-heteroaryl.

As used herein, the term "$C_{1-6}$alkyl-thio" refers to a radical of the formula: —S—$C_{1-6}$alkyl.

As used herein, the term "halo" or "halogen" generally refers to a halogen atom radical, including fluoro, chloro, bromo and iodo.

As used herein, the term "halo-$C_{1-6}$alkoxy" refers to a radical of the formula: —O—$C_{1-6}$alkyl-halo, wherein $C_{1-6}$alkyl is partially or completely substituted with one or more halogen atoms where allowed by available valences.

As used herein, the term "halo-$C_{1-6}$alkyl" refers to a radical of the formula: —$C_{1-6}$alkyl-halo, wherein $C_{1-6}$alkyl is partially or completely substituted with one or more halogen atoms where allowed by available valences.

As used herein, the term "deutero-$C_{1-6}$alkyl" refers to a radical of the formula: —$C_{1-6}$alkyl-deutero, wherein $C_{1-6}$alkyl is partially or completely substituted with one or more deuterium atoms where allowed by available valences.

As used herein, the term "hydroxy" refers to a radical of the formula: —OH.

As used herein, the term "hydroxy-$C_{1-6}$alkyl" refers to a radical of the formula: —$C_{1-6}$alkyl-OH, wherein $C_{1-6}$alkyl is partially or completely substituted with one or more hydroxy radicals where allowed by available valences.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances, one or more substituents having a double bond (e.g., "oxo" or "=O") as the point of attachment may be described, shown or listed herein within a substituent group, wherein the structure may only show a single bond as the point of attachment to the core structure of Formula (I). A person of ordinary skill in the art would understand that, while only a single bond is shown, a double bond is intended for those substituents.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) or a form thereof encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the terms "each instance of" or "in each instance, when present," when used preceding a phrase such as " . . . $C_{3-10}$cycloalkyl, $C_{3-10}$cycloalkyl-$C_{1-4}$alkyl, aryl, aryl-$C_{1-4}$alkyl, heteroaryl, heteroaryl-$C_{1-4}$alkyl, heterocyclyl and heterocyclyl-$C_{1-4}$alkyl," are intended to refer to the $C_{3-10}$cycloalkyl, aryl, heteroaryl and heterocyclyl ring systems when each are present either alone or as a substituent.

As used herein, the term "optionally substituted" means optional substitution with the specified substituent variables, groups, radicals or moieties.

Compound Forms

As used herein, the term "form" means a compound of Formula (I) having a form selected from the group consisting of a free acid, free base, salt, hydrate, solvate, racemate, enantiomer, diastereomer, stereoisomer, and tautomer form thereof.

In certain aspects described herein, the form of the compound of Formula (I) is a free acid, free base or salt thereof.

In certain aspects described herein, the form of the compound of Formula (I) is a salt thereof.

In certain aspects described herein, the form of the compound of Formula (I) is a stereoisomer, racemate, enantiomer, or diastereomer thereof.

In certain aspects described herein, the form of the compound of Formula (I) is a tautomer thereof.

In certain aspects described herein, the form of the compound of Formula (I) is a pharmaceutically acceptable form.

In certain aspects described herein, the compound of Formula (I) or a form thereof is isolated for use.

As used herein, the term "isolated" means the physical state of a compound of Formula (I) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterized by standard analytical techniques described herein or well known to the skilled artisan.

As used herein, the term "protected" means that a functional group in a compound of Formula (I) or a form thereof is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, methoxymethanol, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters. In certain instances, the protecting group may also be a polymer resin, such as a Wang resin or a 2-chlorotrityl-chloride resin. Protecting groups may be added or removed in accordance with standard techniques, which are well-known to those skilled in the art and as described herein. It will also be appreciated by those skilled in the art, although such protected derivatives of compounds described herein may not possess pharmacological activity as such, they may be administered to a subject and thereafter metabolized in the body to form compounds described herein which are pharmacologically active. Such derivatives may therefore be described as "prodrugs". All prodrugs of compounds described herein are included within the scope of the use described herein.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains a hydroxyl functional group, a prodrug form can be prepared by replacing the hydrogen atom of the hydroxyl with another functional group such as alkyl, alkylcarbonyl or a phosphonate ester and the like. In another example, when a compound of Formula (I) or a form thereof contains an amine functional group, a prodrug form can be prepared by replacing one or more amine hydrogen atoms with a functional group such as alkyl or substituted carbonyl. Pharmaceutically acceptable prodrugs of compounds of Formula (I) or a form thereof include those compounds substituted with one or more of the following groups: carboxylic acid esters, sulfonate esters, amino acid esters, phosphonate esters and mono-, di- or triphosphate esters or alkyl substituents, where appropriate. As described herein, it is understood by a person of ordinary skill in the art that one or more of such substituents may be used to provide a compound of Formula (I) or a form thereof as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

As used herein, the term "hydrate" means a solvate wherein the solvent molecule is water.

The compounds of Formula (I) can form salts, which are intended to be included within the scope of this description. Reference to a compound of Formula (I) or a form thereof herein is understood to include reference to salt forms thereof, unless otherwise indicated. The term "salt(s)", as employed herein, denotes acidic salts formed with inorganic and/or organic acids, as well as basic salts formed with inorganic and/or organic bases. In addition, when a compound of Formula (I) or a form thereof contains both a basic moiety, such as, without limitation an amine moiety, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I) may be formed, for example, by reacting a compound of Formula (I) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Particular aspects of acid addition salts include, and are not limited to, acetate, ascorbate, benzoate, benzenesulfonate, bisulfate, bitartrate, borate, bromide, butyrate, chloride, citrate, camphorate, camphorsulfonate, ethanesulfonate, formate, fumarate, gentisinate, gluconate, glucaronate, glutamate, iodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain particular aspects of acid addition salts include chloride or dichloride.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002)

Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium and zinc salts.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (I) and forms thereof, may further exist in a tautomeric form. All such tautomeric forms are contemplated and intended to be included within the scope of the compounds of Formula (I) or a form thereof as described herein.

The compounds of Formula (I) or a form thereof may contain asymmetric or chiral centers, and, therefore, exist in different stereoisomeric forms. The present description is intended to include all stereoisomeric forms of the compounds of Formula (I) as well as mixtures thereof, including racemic mixtures.

The compounds described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one particular aspect, the compounds described herein are (S) isomers and may exist as enantiomerically pure compositions substantially comprising only the (S) isomer. In another particular aspect, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "chiral" refers to a carbon atom bonded to four nonidentical substituents. Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511).

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) or a form thereof is a substantially pure (S) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) or a form thereof is a substantially pure (R) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I) or a form thereof incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates or isotopologues of the instant compounds.

The term "isotopologue" refers to isotopically-enriched compounds described herein which are identical to non-enriched compounds recited herein, but for the fact that, in the enriched form, one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, $^{35}$Cl and $^{36}$Cl, respectively, each of which are also within the scope of this description.

Certain isotopically-enriched compounds described herein (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances.

Compound Uses

Provided herein are methods of treating a disease in a subject in need thereof. As used herein, the term "subject," refers to any animal, including mammals. For example, mice, rats, other rodents, rabbits, dogs, cats, swine, cattle, sheep, horses, primates, and humans. In some aspects, the subject is a human. In some aspects, the method comprises administering to the subject a therapeutically effective amount of a compound provided herein (e.g., a compound of Formula (I)), or a pharmaceutically acceptable salt thereof. In a particular aspect, the disease is familial dysautonomia, a disease of the central and peripheral nervous system associated with one or more pre-mRNA splicing defects.

The present application further provides a method of treating familial dysautonomia in a subject in need thereof, comprising administering to the subject a therapeutically effective amount of a compound provided herein (i.e., a compound of Formula (I)).

In some aspects of the methods provided herein, the compound is selected from the group of compounds of Formula (I), or a pharmaceutically acceptable salt thereof.

In some aspects, the method of improving pre-mRNA splicing of the IKBKAP gene comprises contacting the gene (e.g., in a cell or subject expressing the gene) with a compound provided herein (e.g., a compound of Formula (I)).

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some aspects, the dosage of the compound, or a pharmaceutically acceptable salt thereof, administered to a subject or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Also provided herein are methods for increasing IKBKAP (also referred to as ELP1) protein expression in a patient in need thereof, the method comprising administering an effective amount of a compound provide herein, (i.e., a compound of Formula (I), or a pharmaceutically acceptable salt thereof), to the patient. For example, such methods include increasing IKBKAP protein expression in serum samples from the patient. Further provided herein are methods for increasing the mean percentage of IKBKAP protein expression in a patient in need thereof, the method comprising administering an effective amount of a compound provided herein (i.e., a compound of Formula (I), or a pharmaceutically acceptable salt thereof, to the patient.

Also provided herein are methods for increasing IKBKAP protein expression in a cell (e.g., ex vivo or in vivo), the method comprising contacting the cell with a therapeutically effective amount of a compound provided herein, (i.e., a compound of Formula (I), or a pharmaceutically acceptable salt thereof). In some aspects the method is an in vitro method. In some aspects, the method is an in vivo method. In some aspects, the amount IKBKAP protein expression is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof. In some aspects thereof, the amount of IKBKAP protein expression is increased in the plasma.

Also provided herein are methods for increasing IKBKAP protein level in a patient in need thereof, the method comprising administering an effective amount of a compound provide herein, (i.e., a compound of Formula (I), or a pharmaceutically acceptable salt thereof), to the patient. For example, such methods include increasing IKBKAP protein level in serum samples from the patient. Further provided herein are methods for increasing the mean percentage of IKBKAP protein level in a patient in need thereof, the method comprising administering an effective amount of a compound provided herein (i.e., a compound of Formula (I), or a pharmaceutically acceptable salt thereof, to the patient.

Also provided herein are methods for increasing IKBKAP protein level in a cell (e.g., ex vivo or in vivo), the method comprising contacting the cell with a therapeutically effective amount of a compound provided herein, (i.e., a compound of Formula (I), or a pharmaceutically acceptable salt thereof).

In some aspects, the method is an in vitro method. In some aspects, the method is an in vivo method. In some aspects, the amount IKBKAP protein level is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof. In some aspects thereof, the amount of IKBKAP protein level is increased in plasma.

Also provided herein are methods for increasing full-length IKBKAP mRNA in a patient in need thereof, the method comprising administering an effective amount of a compound provide herein, (i.e., a compound of Formula (I), or a pharmaceutically acceptable salt thereof), to the patient. For example, such methods include increasing full-length IKBKAP mRNA concentration in serum samples from the patient. Further provided herein are methods for increasing the mean percentage exon inclusion (i.e. the percentage of correctly spliced or full-length IKBKAP mRNA) in a patient in need thereof, the method comprising administering an effective amount of a compound provided herein (i.e., a compound of Formula (I), or a pharmaceutically acceptable salt thereof, to the patient.

In some aspects, full-length IKBKAP mRNA can be measured in the serum, for example, in blood samples obtained from the patient prior to administration of a compound as provided herein and in blood samples obtained from the patient following administration of a compound as provided herein. In some aspects, the blood samples obtained from the patient following administration are obtained after one day, two days, three days, four days, five days, six days, seven days, eight days, nine days, ten days, fourteen days, twenty-one days, twenty-eight days, and/or thirty days of administration of the compound as provided herein. See, for example, F. B. Axelrod et al., Pediatr Res (2011) 70(5): 480-483; and R. S. Shetty et al., Human Molecular Genetics (2011) 20(21): 4093-4101, both of which are incorporated by reference in their entirety.

Further provided herein is a method of increasing full-length IKBKAP mRNA in a cell, the method comprising contacting the cell with a therapeutically effective amount of a compound provided herein (i.e., a compound of Formula (I)). The amount of full-length IKBKAP mRNA in the treated cell is increased relative to a cell in a subject in the absence of a compound provided herein. The method of increasing the amount of full-length IKBKAP mRNA in a cell may be performed by contacting the cell with a compound provided herein (i.e., a compound of Formula (I), or a pharmaceutically acceptable salt form thereof), in vitro, thereby increasing the amount full-length IKBKAP mRNA of a cell in vitro. Uses of such an in vitro method of increasing the amount of full-length IKBKAP mRNA include, but are not limited to, use in a screening assay (for example, wherein a compound provided herein is used as a positive control or standard compared to a compound or compounds of unknown activity or potency in increasing the amount full-length IKBKAP mRNA).

In some aspects, the amount of full-length IKBKAP mRNA is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof. In some aspects thereof, the amount of full-length IKBKAP mRNA is increased in the plasma.

The method of increasing full-length IKBKAP mRNA in a cell may be performed, for example, by contacting a cell, (e.g., a lung cell, a muscle cell, a liver cell, a heart cell, a brain cell, a kidney cell, or a nerve cell), with a compound provided herein (i.e. a compound of Formula (I), or a pharmaceutically acceptable salt thereof), in vivo, thereby increasing the amount of full-length IKBKAP mRNA in a subject in vivo. The contacting is achieved by causing a compound provided herein, or a pharmaceutically acceptable salt form thereof, to be present in a subject in an amount effective to achieve an increase in the amount of full-length IKBKAP mRNA. This may be achieved, for example, by administering an effective amount of a compound provided herein, or a pharmaceutically acceptable salt form thereof, to a subject. Uses of such an in vivo method of increasing the amount of full-length IKBKAP mRNA include, but are not limited to, use in methods of treating a disease or condition, wherein an increase in the amount of full-length IKBKAP mRNA is beneficial.

In some aspects thereof, the amount of full-length IKBKAP mRNA is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof, for example in a patient suffering from a disease or disorder provided herein (e.g., familial dysautonomia). The method is preferably performed by administering an effective amount of a compound provided herein, or a pharmaceutically acceptable salt form thereof, to a subject who is suffering from familial dysautonomia.

In some aspects, one or more of the compounds provided herein may be administered to a subject in need thereof in combination with at least one additional pharmaceutical agent. In some embodiments, the additional pharmaceutical agent is a compound provided herein (e.g., a compound of Formula (I)).

Additional examples of suitable additional pharmaceutical agents for use in combination with the compounds of the present application for treatment of the diseases provided herein include, but are not limited to, antioxidants, anti-inflammatory agents, steroids, immunosuppressants, or other agents such as therapeutic antibodies. In some aspects, the compounds provided herein may be administered to a subject in need thereof in combination with at least one additional pharmaceutical agent for the treatment of familial dysautonomia. In some embodiments, the additional pharmaceutical agent is phosphatidylserine.

When employed as a therapeutic agent, the compounds provided herein can be administered in the form of a pharmaceutical composition; thus, the methods described herein can include administering a pharmaceutical composition. These compositions can be prepared as described herein or elsewhere, and can be administered by a variety of routes, depending upon whether local or systemic treatment is desired and upon the area to be treated. Administration may be pulmonary (e.g., by inhalation or insufflation of powders or aerosols, including by nebulizer, intratracheal or intranasal), oral, or parenteral. Parenteral administration may include, but is not limited to intravenous, intraarterial, subcutaneous, intraperitoneal, intramuscular injection or infusion; or intracranial, (e.g., intrathecal, intraocular, or intraventricular) administration. Parenteral administration can be in the form of a single bolus dose, or may be, for example, by a continuous perfusion pump. Conventional pharmaceutical carriers, aqueous, powder or oily bases, thickeners and the like may be necessary or desirable. In some aspects, the compounds provided herein are suitable for oral and parenteral administration. In some aspects, the compounds provided herein are suitable for oral administration. In some aspects, the compounds provided herein are suitable for parenteral administration. In some aspects, the compounds provided herein are suitable for intravenous administration. In some aspects, the compounds provided herein are suitable for transdermal administration (e.g., administration using a patch or microneedle). Pharmaceutical compositions for topical administration may include transdermal patches (e.g., normal or electrostimulated), ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein (e.g., a compound of Formula (I)), or a pharmaceutically acceptable salt thereof, in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood, that the amount of compound to be administered and the schedule of administration will usually be determined by a physician, according to the relevant circumstances, including the condition to be treated, the chosen route of administration, the actual compound administered, the age, weight, and response of the individual subject, the severity of the subject's symptoms, and the like.

Also provided herein are kits including a compound provided herein, more particularly to a compound of Formula (I), or a pharmaceutically acceptable salt thereof. In some embodiments, a kit can include one or more delivery systems, e.g., for a compound provided herein, or a pharmaceutically acceptable salt thereof, and directions for use of the kit (e.g., instructions for treating a subject). In some embodiments, a kit can include a compound provided herein, or a pharmaceutically acceptable salt thereof, and one or more additional agents as provided herein.

In some aspects, the kit can include one or more compounds or additional pharmaceutical agents as provided herein, or a pharmaceutically acceptable salt thereof, and a label that indicates that the contents are to be administered to a subject resistant to a standard of care agent or adjuvant used for the treatment of familial dysautonomia. In some aspects, the additional pharmaceutical agent is phosphatidylserine. In another aspect, the kit can include a compound provided herein, or a pharmaceutically acceptable salt thereof, and a label that indicates that the contents are to be administered to a subject with cells expressing abnormal IKBKAP pre-mRNA splicing. In another aspect, the kit can include one or more compounds or additional pharmaceutical agents as provided herein, or a pharmaceutically acceptable salt thereof, and a label that indicates that the contents are to be administered to a subject having a disease of the central nervous system or peripheral nervous system resulting from abnormal pre-mRNA splicing.

In another aspect, the kit can include one or more compounds or additional pharmaceutical agents as provided herein, or a pharmaceutically acceptable salt thereof, and a label that indicates that the contents are to be administered to a subject having familial dysautonomia. In some aspects, a kit can include one or more compounds as provided herein, or a pharmaceutically acceptable salt thereof and a label that indicates that the contents are to be administered with one or more additional pharmaceutical agents as provided herein.

In another aspect, the concentration-biological effect relationship observed with regard to a compound of Formula (I) or a form thereof indicate a target plasma concentration ranging from approximately 0.001 µg·hr/mL to approximately 50 µg·hr/mL, from approximately 0.01 µg·hr/mL to approximately 20 µg·hr/mL, from approximately 0.05 µg·hr/mL to approximately 10 µg·hr/mL, or from approximately 0.1 µg·hr/mL to approximately 5 µg·hr/mL. To achieve such plasma concentrations, the compounds described herein may be administered at doses that vary, such as, for example, without limitation, from 1.0 ng to 10,000 mg.

In one aspect, the dose administered to achieve an effective target plasma concentration may be administered based upon subject or patient specific factors, wherein the doses administered on a weight basis may be in the range of from about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 mg/kg/day to about 1000 mg/kg/day, or about 0.001 mg/kg/day to about 500 mg/kg/day, or about 0.001 mg/kg/day to about 250 mg/kg/day, or about 0.001 mg/kg/day to about 200 mg/kg/day, or about 0.001 mg/kg/day to about 150 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 25 mg/kg/day, or about 0.001 mg/kg/day to about 10 mg/kg/day, or about 0.001 mg/kg/day to about 5 mg/kg/day, or about 0.001 mg/kg/day to about 1 mg/kg/day, or about 0.001 mg/kg/day to about 0.5 mg/kg/day, or about 0.001 mg/kg/day to about 0.1 mg/kg/day, or from about 0.01 mg/kg/day to about 3500 mg/kg/day, or about 0.01 mg/kg/day to about 3000 mg/kg/day, or about 0.01 mg/kg/day to about 2500 mg/kg/day, or about 0.01 mg/kg/day to about 2000 mg/kg/day, or about 0.01 mg/kg/day to about 1500 mg/kg/day, or about 0.01 mg/kg/day to about 1000 mg/kg/day, or about 0.01 mg/kg/day to about 500 mg/kg/day, or about 0.01 mg/kg/day to about 250 mg/kg/day, or about 0.01 mg/kg/day to about 200 mg/kg/day, or about 0.01 mg/kg/day to about 150 mg/kg/day, or about 0.01 mg/kg/day to about 100 mg/kg/day, or about 0.01 mg/kg/day to about 75 mg/kg/day, or about 0.01 mg/kg/day to about 50 mg/kg/day, or about 0.01 mg/kg/day to about 25 mg/kg/day, or about 0.01 mg/kg/day to about 10 mg/kg/day, or about 0.01 mg/kg/day to about 5 mg/kg/day, or about 0.01 mg/kg/day to about 1 mg/kg/day, or about 0.01 mg/kg/day to about 0.5 mg/kg/day, or about 0.01 mg/kg/day to about 0.1 mg/kg/day, or from about 0.1 mg/kg/day to about 3500 mg/kg/day, or about 0.1 mg/kg/day to about 3000 mg/kg/day, or about 0.1 mg/kg/day to about 2500 mg/kg/day, or about 0.1 mg/kg/day to about 2000 mg/kg/day, or about 0.1 mg/kg/day to about 1500 mg/kg/day, or about 0.1 mg/kg/day to about 1000 mg/kg/day, or about 0.1 mg/kg/day to about 500 mg/kg/day, or about 0.1 mg/kg/day to about 250 mg/kg/day, or about 0.1 mg/kg/day to about 200 mg/kg/day, or about 0.1 mg/kg/day to about 150 mg/kg/day, or about 0.1 mg/kg/day to about 100 mg/kg/day, or about 0.1 mg/kg/day to about 75 mg/kg/day, or about 0.1 mg/kg/day to about 50 mg/kg/day, or about 0.1 mg/kg/day to about 25 mg/kg/day, or about 0.1 mg/kg/day to about 10 mg/kg/day, or about 0.1 mg/kg/day to about 5 mg/kg/day, or about 0.1 mg/kg/day to about 1 mg/kg/day, or about 0.1 mg/kg/day to about 0.5 mg/kg/day.

Effective amounts for a given subject may be determined by routine experimentation that is within the skill and judgment of a clinician or a practitioner skilled in the art in light of factors related to the subject. Dosage and administration may be adjusted to provide sufficient levels of the active agent(s) or to maintain the desired effect. Factors which may be taken into account include genetic screening, severity of the disease state, status of disease progression, general health of the subject, ethnicity, age, weight, gender, diet, time of day and frequency of administration, drug combination(s), reaction sensitivities, experience with other therapies, and tolerance/response to therapy.

The dose administered to achieve an effective target plasma concentration may be orally administered once (once in approximately a 24 hour period; i.e., "q.d."), twice (once in approximately a 12 hour period; i.e., "b.i.d." or "q.12 h"), thrice (once in approximately an 8 hour period; i.e., "t.i.d." or "q.8 h"), or four times (once in approximately a 6 hour period; i.e., "q.d.s.", "q.i.d." or "q.6 h") daily.

In certain aspects, the dose administered to achieve an effective target plasma concentration may also be administered in a single, divided, or continuous dose for a patient or subject having a weight in a range of between about 40 to about 200 kg (which dose may be adjusted for patients or subjects above or below this range, particularly children under 40 kg). The typical adult subject is expected to have a median weight in a range of about 70 kg. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, sublingual, transdermal, subcutaneous, intramuscular, intraveneous (bolus and infusion), intracerebral, and pulmonary routes of administration.

In another aspect, the dose administered may be adjusted based upon a dosage form described herein formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 3.0, 5.0, 10, 20, 30, 40, 50, 100, 150, 200, 250, 300, 400, 500, 1000, 1500, 2000, 2500, 3000 or 4000 mg/day.

For any compound, the effective amount can be estimated initially either in cell culture assays or in relevant animal models, such as a mouse, guinea pig, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is therapeutic index, and can be expressed as the ratio, $LD_{50}/ED_{50}$. In certain aspects, the effective amount is such that a large therapeutic index is achieved. In further particular aspects, the dosage is within a range of circulating concentrations that include an $ED_{50}$ with little or no toxicity. The dosage may vary within this range depending upon the dosage form employed, sensitivity of the patient, and the route of administration.

Another aspect included within the scope of the present description are the use of in vivo metabolic products of the compounds described herein. Such products may result, for example, from the oxidation, reduction, hydrolysis, amidation, esterification and the like of the administered compound, primarily due to enzymatic processes. Accordingly, the description includes the use of compounds produced by a process comprising contacting a compound described herein with a mammalian tissue or a mammal for a period of time sufficient to yield a metabolic product thereof.

Such products typically are identified by preparing a radio-labeled isotopologue (e.g., $^{14}C$ or $^{3}H$) of a compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. The conversion products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Preparation of Compounds

General Synthetic Methods

As disclosed herein, general methods for preparing the compounds of Formula (I) or a form thereof as described herein are available via standard, well-known synthetic methodology. Many of the starting materials are commercially available or, when not available, can be prepared using the routes described below using techniques known to those skilled in the art. The synthetic schemes provided herein comprise multiple reaction steps, each of which is intended to stand on its own and can be carried out with or without any preceding or succeeding step(s). In other words, each of the individual reaction steps of the synthetic schemes provided herein in isolation is contemplated.

Scheme A
Compounds of Formula (I)
may be prepared as described in Scheme A below.

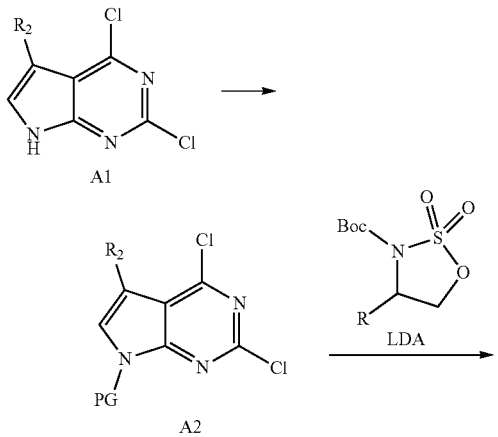

-continued

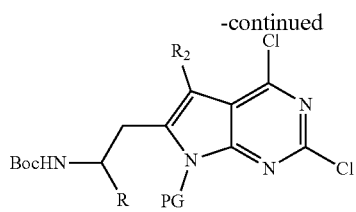
A3

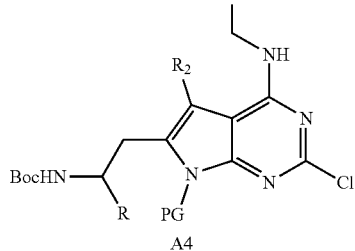
A4

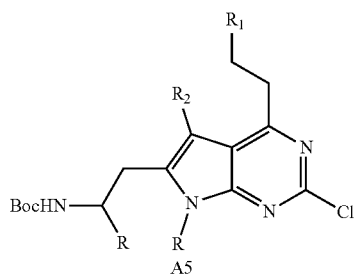
A5

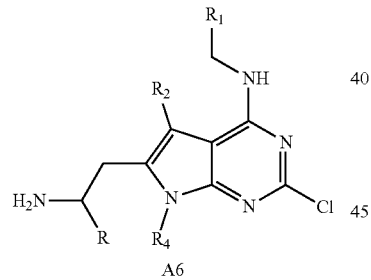
A6

Scheme B
Compounds of Formula (I) may be prepared as described in Scheme B below.

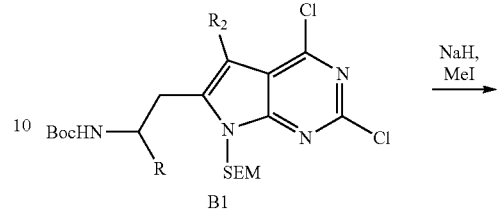
B1

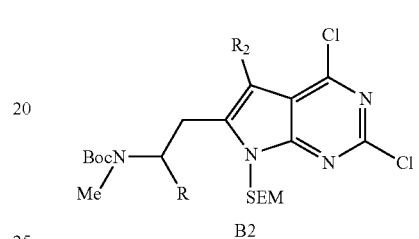
B2

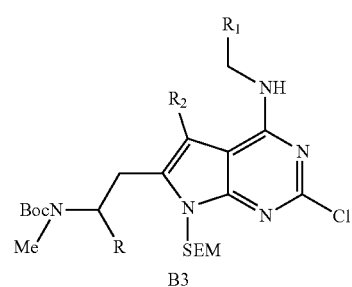
B3

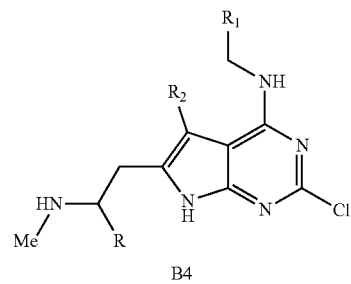
B4

Compound A1 is converted to compound A2 through reaction with a base such as NaH in a suitable solvent (such as DMF and the like) followed by treatment with either SEMCl or MesSO₂Cl. Compound A2 is converted to compound A3 through reaction with a suitable base such as LDA followed by treatment with an optionally substituted cyclic sulfamidate in a suitable solvent (such as THF and the like). Compound A3 is converted to compound A4 through nucleophilic substitution with a primary amine in the presence of a suitable base (such as DIPEA and the like) in a suitable solvent (such as dioxane and the like). Compound A4 is converted to compound A5 either through treatment with a fluoride source (such as TBAF and the like) or treatment with K₂CO₃ in MeOH. Compound A5 is converted to compound A6 either through treatment with acid (HCl or TFA in dioxane and the like) or by reaction with a suitable base such as NaH followed by treatment with MeI in a suitable solvent (such as DMF and the like) and then treatment with acid (HCl or TFA in dioxane and the like).

Compound B1 is converted to compound B2 by treatment with a suitable base such as NaH followed by MeI in a suitable solvent (such as DMF and the like). Compound B2 is converted to compound B3 through nucleophilic substitution with a primary amine in the presence of a suitable base (such as DIPEA and the like) in a suitable solvent (such as dioxane and the like). Finally, compound B3 is converted to compound B4 through treatment with a fluoride source (such as TBAF and the like) in a suitable solvent (such as THF and the like) followed by treatment with acid (such as HCl or TFA in dioxane and the like).

Scheme C
Compounds of Formula (I) may be prepared as described in Scheme C below.

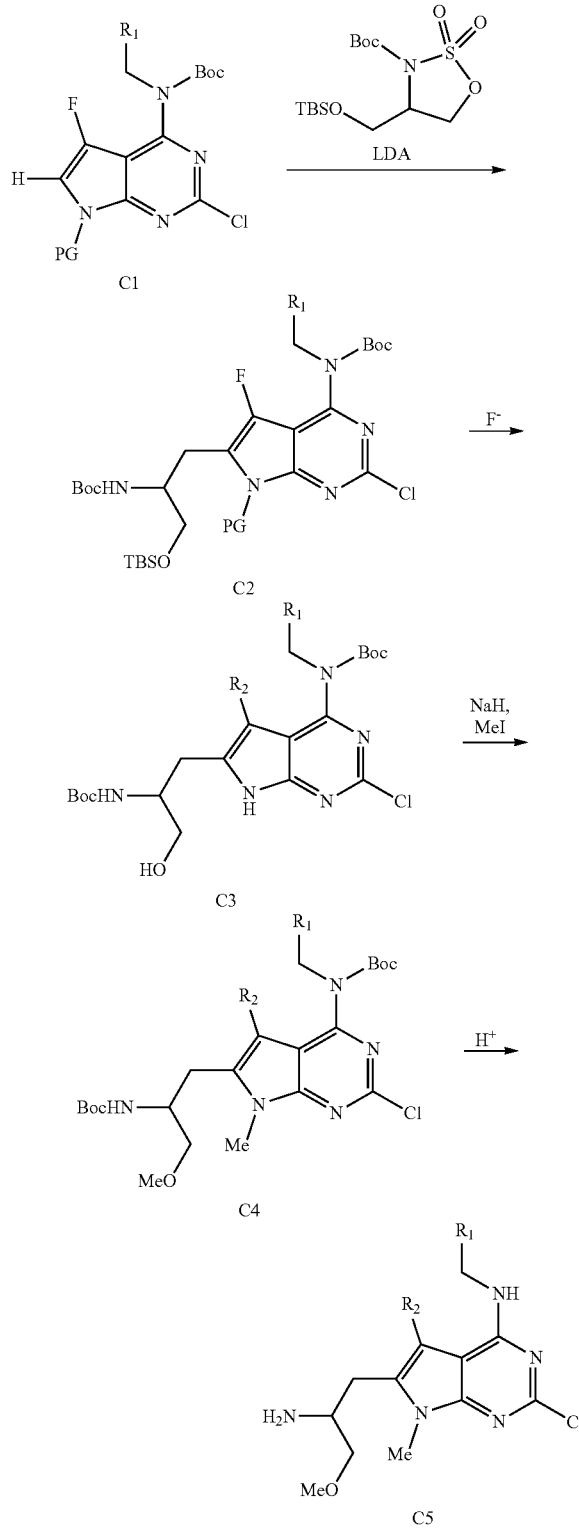

addition of cyclic sulfamidate. Compound C2 is converted to compound C3 by treatment with a fluoride source (such as TBAF and the like) in a suitable solvent (such as THF and the like). Compound C3 is converted to compound C4 through reaction with an appropriate base (such as NaH and the like) in a suitable solvent (such as DMF and the like) followed by treatment with MeI. Finally, compound C4 is converted to compound C5 by treatment with acid (such as HCl or TFA in dioxane and the like).

Scheme D
Compounds of Formula (I) may be prepared as described in Scheme D below.

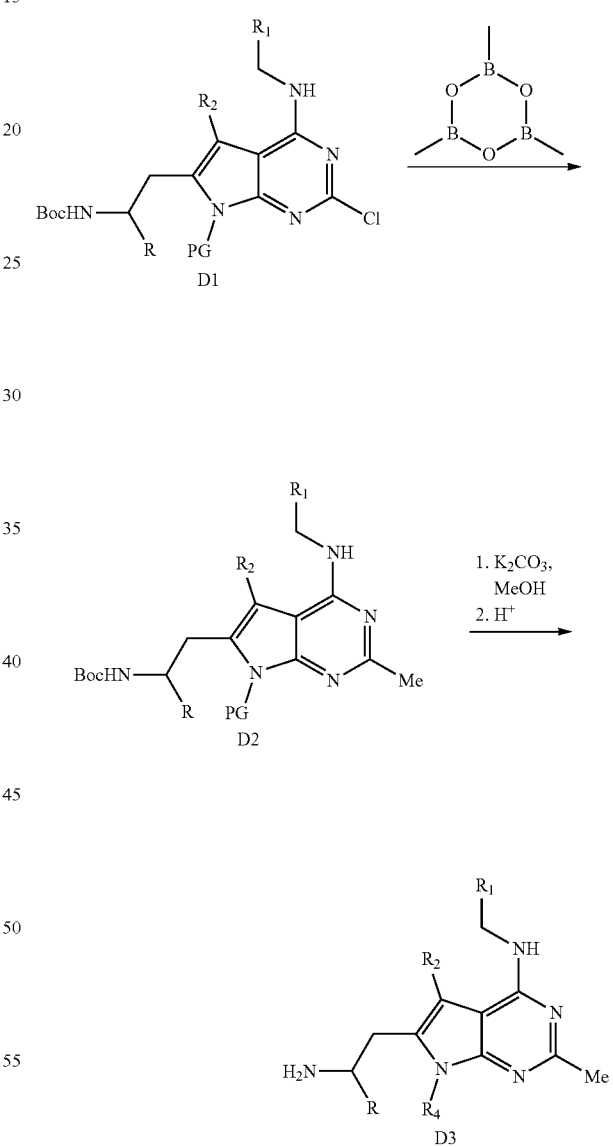

Compound C1 is converted to compound C2 through treatment with an appropriate base (such as LDA and the like) in a suitable solvent (such as THF and the like) followed by Compound D1 is converted to compound D2 through a Suzuki coupling with trimethylboroxine in the presence of a catalyst (such as Pd(dppf)Cl$_2$ and the like) and base (such as aqueous K$_2$CO$_3$ and the like) in a suitable solvent (such as 1,4-dioxane and the like). Compound D2 is converted to compound D3 via treatment with K$_2$CO$_3$ in MeOH followed by acid (such as HCl or TFA in dioxane and the like).

Scheme E
Compounds of Formula (I) may be prepared as described in Scheme E below.

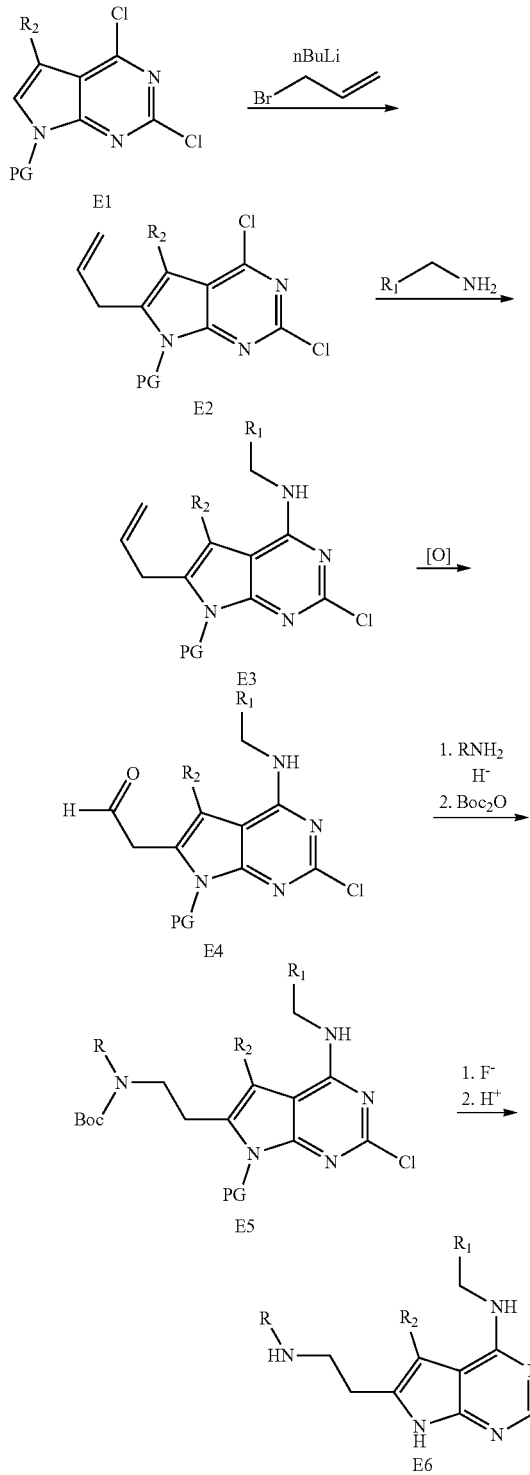

suitable solvent (such as dioxane and the like). Treatment of compound E3 with an appropriate oxidant (such as $OsO_4$ and the like) in a suitable solvent mixture (such as acetone/water and the like) followed by reaction with $NaIO_4$ in a suitable solvent (such as THF and the like) provides compound E4. Compound E4 is converted to compound E5 in a two-step process beginning with reductive amination with a primary amine and a hydride source (such as $NaBH(OAc)_3$ and the like) in a suitable solvent (such as DCE and the like) followed by treatment with $Boc_2O$. Compound E5 is converted to compound E6 by treatment with a fluoride source (such as TBAF and the like) in a suitable solvent (such as THF and the like) followed by acid (such as HCl or TFA in dioxane and the like).

Scheme F
Compounds of Formula (I) may be prepared as described in Scheme F below.

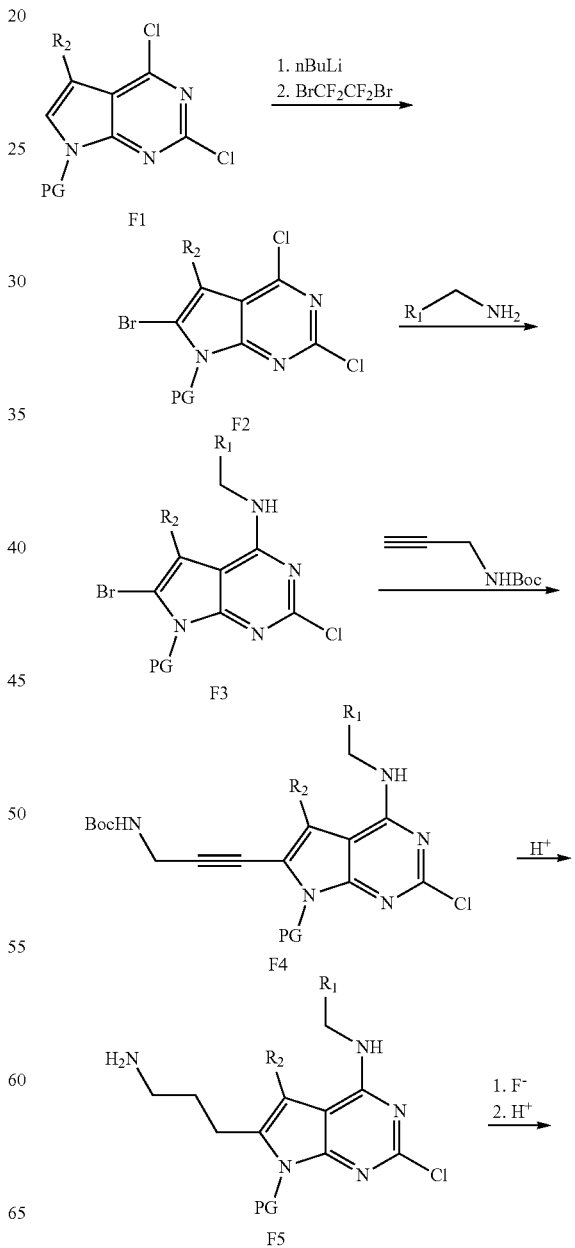

Compound E1 is converted to compound E2 by treatment with abase (such as nBuLi and the like) followed by addition of allyl bromide in a suitable solvent (such as THF and the like). Compound E2 is converted to compound E3 through nucleophilic substitution with a primary amine in the presence of a suitable base (such as DIPEA and the like) in a -continued

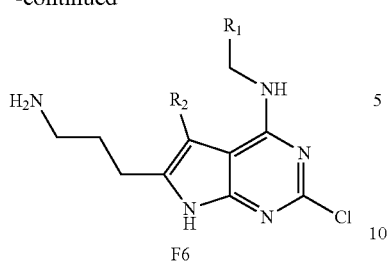

F6

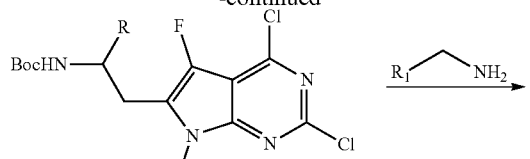

G3

Compound F1 is converted to compound F2 via treatment with an appropriate base (such as nBuLi and the like) followed by reaction with an electrophilic halogenating source (such as dibromotetrafluoroethane and the like) in a suitable solvent (such as THF and the like). Compound F2 is converted to compound F3 through nucleophilic substitution with a primary amine in the presence of a suitable base (such as DIPEA and the like) in a suitable solvent (such as dioxane and the like). Compound F3 is converted to compound F4 via a Sonogashira coupling with N-boc-propargylamine in the presence of a catalyst (such as $Pd(PPh_3)_2$ and CuI and the like) and a base (such as TEA and the like) in a suitable solvent (such as $CH_3CN$ and the like). Compound F4 is converted to compound F5 through reduction of the alkyne with $H_2$ in the presence of a catalyst (such as Pd/C and the like) in a suitable solvent (such as EtOAc and the like). Compound F5 is converted to compound F6 by treatment with a fluoride source (such as TBAF and the like) in a suitable solvent (such as THF and the like) followed by acid (such as HCl or TFA in dioxane and the like).

Scheme G
Compounds of Formula (I) may be prepared as described in Scheme G below.

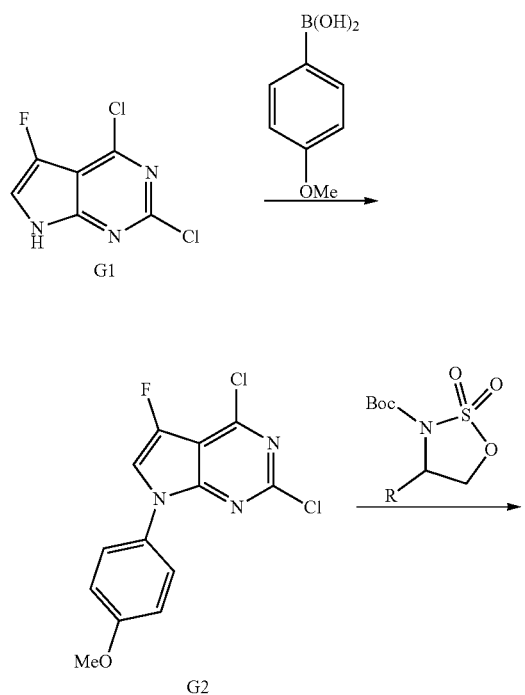

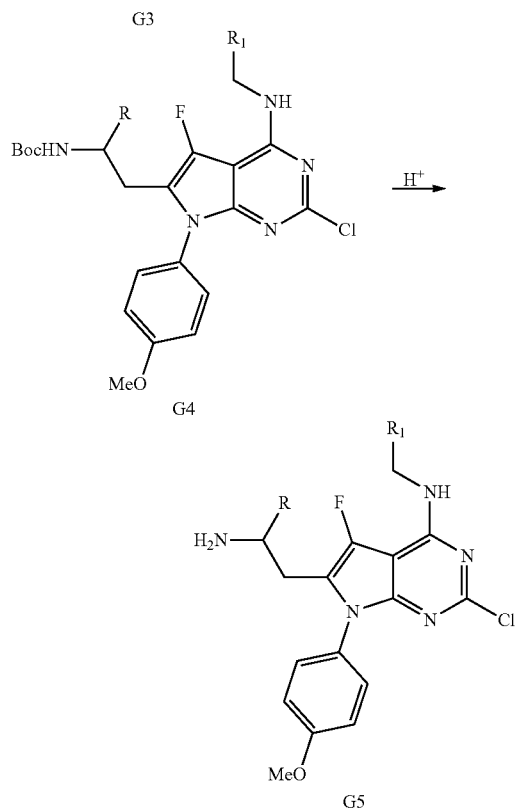

Compound G1 is converted to compound G2 through a Chan-Lam coupling with an arylboronic acid in the presence of a Cu(II) catalyst (such as $Cu(OAc)_2$ and the like) and a base (such as TEA and the like) in a solvent (such as $CH_2Cl_2$ and the like). Compound G2 is converted to compound G3 through reaction with a suitable base such as LDA followed by treatment with an optionally substituted cyclic sulfamidate in a suitable solvent (such as THF and the like). Compound G3 is converted to compound G4 through nucleophilic substitution with a primary amine in the presence of a suitable base (such as DIPEA and the like) in a suitable solvent (such as dioxane and the like). Finally, compound G4 is converted to compound G5 through treatment with acid (such as HCl or TFA in dioxane and the like).

SPECIFIC SYNTHETIC EXAMPLES

To describe in more detail and assist in understanding, the following non-limiting examples are offered to more fully illustrate the scope of compounds described herein and are not to be construed as specifically limiting the scope thereof. Such variations of the compounds described herein that may be now known or later developed, which would be within the purview of one skilled in the art to ascertain, are considered to fall within the scope of the compounds as described herein and hereinafter claimed. These examples illustrate the preparation of certain compounds. Those of skill in the art will understand that the techniques described in these examples represent techniques, as described by those of ordinary skill in the art, that function well in synthetic practice, and as such constitute preferred modes for the practice thereof. However, it should be appreciated that those of skill in the art should, in light of the present disclosure, appreciate that many changes can be made in the specific methods that are disclosed and still obtain a like or similar result without departing from the spirit and scope of the present description.

Other than in the following examples of the embodied compounds, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and rounding techniques used by those of skill in the art.

While the numerical ranges and parameters setting forth the broad scope of the present description are approximations, the numerical values set forth in the examples set forth below are reported as precisely as possible. Any numerical value, however, inherently contains certain errors necessarily resulting from the standard deviation found in their respective testing measurements.

COMPOUND EXAMPLES

As used above, and throughout the present description, the following abbreviations, unless otherwise indicated, shall be understood to have the following meanings:

| Abbreviation | Meaning |
| --- | --- |
| Δ | heating (chemistry), deletion (biology), lack of (biology) |
| AcOH or HOAc | acetic acid |
| Ar | argon |
| ACN or CH$_3$CN | acetonitrile |
| atm | atmosphere(s) |
| n-BuLi | n-butyl lithium |
| ° C. | degrees Celsius |
| Celite ® or Celite | diatomaceous earth |
| CuI | copper (I) iodide |
| d/h/hr/hrs/min/s | day(d)/hour(h, hr or hrs)/minute(min)/second(s) |
| DCM or CH$_2$Cl$_2$ | dichloromethane |
| DIEA or DIPEA | N,N-diisopropylethylamine |
| DMAP | 4-(dimethylamino)pyridine or N,N-dimethylpyridin-4-amine |
| DMF | dimethylformamide |
| DMSO | dimethylsulfoxide |
| EtOAc | ethyl acetate |

-continued

| Abbreviation | Meaning |
| --- | --- |
| EtOH | ethanol |
| Et$_2$O | diethyl ether |
| eq. | equivalent(s) |
| HCl | hydrochloric acid |
| H$_2$SO$_4$ | sulfuric acid |
| LC/MS, LCMS or LC-MS | liquid chromatographic mass spectroscopy |
| MeOH | methanol |
| MgSO$_4$ | magnesium sulfate |
| MS | mass spectroscopy |
| NEt$_3$ | triethylamine |
| NH$_4$Cl | ammonium chloride |
| NaH | sodium hydride |
| NaHCO$_3$ | sodium bicarbonate |
| NaOH | sodium hydroxide |
| Na$_2$SO$_4$ | sodium sulfate |
| N$_2$ | nitrogen |
| NH$_4$Cl | ammonium chloride |
| NMR | nuclear magnetic resonance |
| PhMe or PhCH$_3$ | toluene |
| Psi | pounds per square inch pressure |
| PTFE | polytetrafluoroethylene |
| Rt or rt | room temperature |
| RT | retention time |
| Selectfluor ® | 1-chloromethyl-4-fluoro-1,4-diazoniabicyclo[2.2.2]octane bis(tetrafluoroborate) |
| TBAF | tetrabutylammonium fluoride |
| TEA, Et$_3$N or NEt$_3$ | triethylamine |
| TFA | trifluoroacetic acid |
| THF | tetrahydrofuran |
| TLC | thin layer chromatography |
| t-Bu | tert-butyl |

Intermediate 1

2,4-Dichloro-7-((2-(trimethylsilyl)ethoxy)methyl)-7H-pyrrolo[2,3-d]pyrimidine

To a stirred solution of 2,4-dichloro-7H-pyrrolo[2,3-d]pyrimidine (5.87 g, 31.2 mmol, 1.0 eq.) in THF (60 mL) and DMF (20 mL) was added NaH (60 mass %) in mineral oil (1.4 g, 35.0 mmol, 1.1 eq.) at 0° C. The reaction was warmed up to room temperature then stirred for 20 min at room temperature. The reaction mixture was cooled to 0° C. before 2-(trimethylsilyl)ethoxymethyl chloride (5.84 g, 6.2 mL, 33.3 mmol, 1.07 eq.) was added at 0° C. The reaction progress was monitored by LC-MS analysis of an aliquot of the mixture. After 1.5 h, the reaction was quenched by ammonium chloride (aq. sat., 40 mL) then extracted with diethyl ether (3×50 mL). The combined organic layers were dried over sodium sulfate and then concentrated to give crude product which was purified by flash column chromatography (120 g, 0-10% EtOAc/hexanes) to afford the title compound (9.56 g, 30.0 mmol) as a solid in 96% yield. LC-MS: 318.2/320.0 [M+H]$^+$, RT 1.76 min. $^1$H NMR (500 MHz, acetone-d$_6$) δ ppm −0.05 (s, 9H), 0.86-0.96 (m, 2H), 3.54-3.70 (m, 2H), 5.68 (s, 2H), 6.75 (d, J=3.78 Hz, 1H), 7.78 (d, J=3.78 Hz, 1H).

Intermediate 2

2,4-Dichloro-5-fluoro-7-(mesitylsulfonyl)-7H-pyrrolo[2,3-d]pyrimidine

Step 1: 2,4-Dichloro-5-fluoro-7H-pyrrolo[2,3-d]pyrimidine

To a solution of 2,4-dichloro-7H-pyrrolo[2,3-d]pyrimidine (40.8 g, 217 mmol) in ACN (500 mL) was added AcOH (152 mL) at room temperature, followed by addition of Selectfluor® (116 g, 327 mmol). The reaction mixture was stirred at 75° C. overnight. The reaction mixture was concentrated and then diluted with 200 mL of ethyl acetate. The resulting solution was neutralized with saturated NaHCO$_3$, then washed with H$_2$O (3×200 mL), and then washed with brine (100 mL). The organic phase was dried over anhydrous sodium sulfate, and then concentrated. The crude product was purified by silica gel column chromatography eluting with EtOAc in DCM (0% to 20%, and then to 40%) to afford the tide product as a pink solid (19.2 g) in 43% yield. LC-MS: 206 [M+H]$^+$; RT=1.34 min.

Step 2: 2,4-Dichloro-5-fluoro-7-(mesitylsulfonyl)-7H-pyrrolo[2,3-d]pyrimidine

To a solution of 2,4-dichloro-5-fluoro-7H-pyrrolo[2,3-d]pyrimidine (19.2 g, 93.0 mmol) in DCM (500 mL) was added MeSO$_2$Cl (30.4 g, 139 mmol) and DMAP (0.284 g, 2.32 mmol), followed by addition of DIPEA (48.5 g, 375 mmol). The reaction mixture was stirred at room temperature for ~20 min, and TLC showed complete conversion. The reaction mixture was washed with H$_2$O (3×200 mL) and 100 mL of brine. The combined aqueous phases were back-extracted with DCM (100 mL). The combined organic phases were dried over anhydrous sodium sulfate, and concentrated to give the crude product. The crude product was purified by silica gel column chromatography eluting with EtOAc in petroleum ether (0% to 5%). The product was further purified by trituration in petroleum ether to give the title compound (28 g) as a white solid in 78% yield. LC-MS: 387.9 [M+H]$^+$; RT=2.18. $^1$H NMR (500 MHz, acetone-d$_6$) δ ppm 2.33 (s, 3H), 2.71 (s, 6H), 7.15 (s, 2H), 8.13 (d, J=2.44 Hz, 1H).

Intermediate 3

2,4-Dichloro-5-fluoro-7-((2-(trimethylsilyl)ethoxy)methyl)-7H-pyrrolo[2,3-d]pyrimidine The title compound was prepared from 2,4-dichloro-5-fluoro-7H-pyrrolo[2,3-d]pyrimidine (Intermediate 2 step 1) according to the procedure described for Intermediate 1.

Intermediate 4

2,4,5-Trichloro-7-((2-(trimethylsilyl)ethoxy)methyl)-7H-pyrrolo[2,3-d]pyrimidine The title compound was prepared from 2,4,5-trichloro-7H-pyrrolo[2,3-d]pyrimidine according to the procedure described for Intermediate 1.

Intermediate 5

5-Bromo-2,4-dichloro-7-((2-(trimethylsilyl)ethoxy)methyl)-7H-pyrrolo[2,3-d]pyrimidine The title compound was prepared from 5-bromo-2,4-dichloro-7H-pyrrolo[2,3-d]pyrimidine according to the procedure described for Intermediate 1.

Intermediate 6

2,4-Dichloro-7-(mesitylsulfonyl)-5-methyl-7H-pyrrolo[2,3-d]pyrimidine

Step 1: 2,4-Dichloro-5-iodo-7-(mesitylsulfonyl)-7H-pyrrolo[2,3-d]pyrimidine

The title compound was prepared from 2,4-dichloro-5-iodo-7H-pyrrolo[2,3-d]pyrimidine according to the procedure described for Intermediate 2, step 2.

Step 2: 2,4-Dichloro-7-(mesitylsulfonyl)-5-methyl-7H-pyrrolo[2,3-d]pyrimidine

To a 250 mL oven-dried round-bottom flask was added 2,4-dichloro-5-iodo-7-(mesitylsulfonyl)-7H-pyrrolo[2,3-d]pyrimidine (4.66 g, 9.4 mmol) followed by tetrakis(triphenylphosphine)palladium (200 mg, 0.17 mmol, 0.02 eq.). The flask was evacuated and then back-filled with an Ar balloon (I atm). To the solid mixture was added THF (80 mL) followed by methylzinc chloride solution (2.0 M in THF, 5.2 mL, 10.4 mmol, 1.1 eq.) at room temperature. Nitrogen was bubbled through the reaction mixture for 10 min before the reaction was heated to 60° C. and then stirred at 60° C. overnight. The reaction was monitored by LC-MS and TLC analysis. The reaction was quenched by sodium bicarbonate (aq. sat., ~40 mL) and then extracted with EtOAc (2×60 mL). The combined organic phases were washed with brine (50 mL), dried over sodium sulfate and then concentrated to give the crude product which was purified by flash column chromatography (0-10% EtOAc in hexanes) to afford the title compound (3.37 g, 8.6 mmol) as a white solid in 93% yield. $^1$H NMR (500 MHz, acetone-d$_6$) δ ppm 2.31 (s, 3H), 2.50 (d, J=1.53 Hz, 3H), 2.69 (s, 6H), 7.12 (s, 2H), 7.92 (d, J=1.22 Hz, 1H).

Intermediate 7

2,4-Dichloro-7-(mesitylsulfonyl)-7H-pyrrolo[2,3-d]pyrimidine

The title compound was prepared from 2,4-dichloro-7H-pyrrolo[2,3-d]pyrimidine according to the procedure described for Intermediate 2, step 2.

Intermediate 8

2,4,5-Trichloro-7-(mesitylsulfonyl)-7H-pyrrolo[2,3-d]pyrimidine

The title compound was prepared from 2,4,5-trichloro-7H-pyrrolo[2,3-d]pyrimidine according to the procedure described for Intermediate 2, step 2.

Intermediate 9 tert-Butyl (2-chloro-5-fluoro-7-(mesitylsulfonyl)-7H-pyrrolo[2,3-d]pyrimidin-4-yl)(furan-2-ylmethyl)carbamate Step 1: 2-Chloro-5-fluoro-N-(furan-2-ylmethyl)-7-mesitylsulfonyl-7H-pyrrolo[2,3-d]pyrimidin-4-amine To a stirred solution of 2,4-dichloro-5-fluoro-7-(mesitylsulfonyl)-7H-pyrrolo[2,3-d]pyrimidine (Intermediate 2, 1.98 g, 5.10 mmol, 1.0 eq.) in 1,4-dioxane (16.0 mL) was added furfurylamine (659 mg, 0.6 mL, 6.72 mmol, 1.32 eq.) followed by DIPEA (1.04 g, 1.4 mL, 7.96 mmol, 1.56 eq.) at room temperature. Then the reaction mixture was heated to 60° C. and stirred at 60° C. overnight. The reaction progress was monitored by LC-MS analysis of an aliquot of mixture. After 16 h, LC-MS analysis of an aliquot of the mixture indicated the presence of <5% of the starting material. The reaction was quenched with water (~10 mL) then the mixture was extracted with EtOAc (2×40 mL). The combined organic layers were washed with water followed by brine (50 mL) then dried over sodium sulfate. The volatiles were removed under reduced pressure to give crude product which was purified by flash column chromatography (0-15% EtAOc in hexanes) to afford 2-chloro-5-fluoro-N-(2-furylmethyl)-7-(2,4,6-trimethylphenyl)sulfonyl-pyrrolo[2,3-d]pyrimidin-4-amine (2.24 g, 4.99 mmol) as a light yellow foam in 98% yield. LC-MS: 449.2 [M+H]$^+$, 447.3 [M−H]$^−$; RT=1.72 min. $^1$H NMR (500 MHz, acetone-d$_6$) δ ppm 2.31 (s, 3H), 2.69 (s, 6H), 4.75 (d, J=6.10 Hz, 2H), 6.27-6.40 (m, 2H), 7.10 (s, 2H), 7.44 (d, J=0.92 Hz, 1H), 7.49-7.66 (m, 2H).

Step 2: tert-Butyl (2-chloro-5-fluoro-7-(mesitylsulfonyl)-7H-pyrrolo[2,3-d]pyrimidin-4-yl)(furan-2-ylmethyl)carbamate To a stirred solution of 2-chloro-5-fluoro-N-(furan-2-ylmethyl)-7-(mesitylsulfonyl)-7H-pyrrolo[2,3-d]pyrimidin-4-amine (2.24 g, 4.99 mmol, 1.000 eq.) in DCM (15 mL) was added di-tert-butyl dicarbonate (2.95 g, 13.1 mmol, 2.63 eq.) followed by DMAP (200 mg, 1.60 mmol, 0.32 eq.) at room temperature. The reaction mixture was stirred at room temperature overnight. The reaction progress was monitored by TLC and LC-MS analysis of an aliquot of the mixture. The volatiles were removed under reduced pressure to give a crude product which was purified by flash column chromatography (0-15% EtOAc in hexanes) to afford tert-butyl N-[2-chloro-5-fluoro-7-(2,4,6-trimethylphenyl)sulfonyl-pyrrolo[2,3-d]pyrimidin-4-yl]-N-(2-furylmethyl)carbamate (2.2 g, 4.01 mmol) as a white solid in 80% yield. $^1$H NMR (500 MHz, acetone-d$_6$) δ ppm 1.44 (s, 9H) 2.32 (s, 3H) 2.70 (s, 6H) 5.13 (s, 2H) 6.28-6.33 (m, 2H) 7.14 (s, 2H) 7.31-7.47 (m, 1H) 7.93 (d, J=2.44 Hz, 1H).

Intermediate 10 tert-Butyl (2-chloro-7-(mesitylsulfonyl)-5-methyl-7H-pyrrolo[2,3-d]pyrimidin-4-yl)(furan-2-ylmethyl)carbamate The title compound was prepared from Intermediate 6 according to the procedure described for Intermediate 9.

Intermediate 11

5-Butyl-2,4-dichloro-7-(mesitylsulfonyl)-7H-pyrrolo[2,3-d]pyrimidine

Step 1: 5-Butyl-2,4-dichloro-7H-pyrrolo[2,3-d]pyrimidine

To a stirred solution of 5-bromo-2,4-dichloro-7H-pyrrolo[2,3-d]pyrimidine (2.49 g, 9.3 mmol) in THF (20 mL) was added n-BuLi (2.5 M in hexanes, 11.0 mL, 28 mmol, 3.0 eq.) at ~78° C. via syringe pump over 10 min. The reaction mixture turned to an orange suspension. To the suspension was added THF (20 mL) and then the reaction mixture was stirred at ~78° C. for 1 h before a solution of MeI (1.37 g, 0.6 mL, 9.63 mmol, 1.03eq.) in THF (8 mL) was added to the reaction mixture at −78° C. via syringe pump over 1 h. The reaction mixture was stirred at −78° C. for 1 h and then the reaction mixture was warmed up to room temperature slowly overnight (keeping the −78° C. dry ice/acetone bath). After 16 h, the reaction was quenched with ammonium chloride (aq. sat. ~20 mL) then extracted with EtOAc (2×40 mL). The combined organic phases were dried over sodium sulfate and then concentrated to give the crude product which was carried over to the next step without any further purification.

Step 2: 5-Butyl-2,4-dichloro-7-(mesitylsulfonyl)-7H-pyrrolo[2,3-d]pyrimidine

The title compound was prepared from 5-butyl-2,4-dichloro-7H-pyrrolo[2,3-d]pyrimidine according to the procedure described for Intermediate 2 step 2. $^1$H NMR (500 MHz, acetone-d) δ ppm 0.97 (t, J=7.3 Hz, 3H), 1.41-1.51 (m, 2H), 1.74 (quin, J=7.6 Hz, 2H), 2.31 (s, 3H), 2.69 (s, 6H), 2.88-2.97 (m, 2H), 7.12 (s, 2H), 7.91 (s, 1H).

Intermediate 12 tert-Butyl (S)-(1-(2,4-dichloro-5-fluoro-7-(4-methoxyphenyl)-7H-pyrrolo[2,3-d]pyrimidin-6-yl)propan-2-yl)carbamate Step 1: 2,4-Dichloro-5-fluoro-7-(4-methoxyphenyl)-7H-pyrrolo[2,3-d]pyrimidine To a suspension of 2,4-dichloro-5-fluoro-7H-pyrrolo[2,3-d]pyrimidine (500 mg, 2.4 mmol), 4-methoxyphenylboronic acid (420 mg, 2.8 mmol, 1.2 eq.), and triethylamine (0.5 mL, 4 mmol, 1.7 eq.) in CH$_2$Cl$_2$ (20 mL) was added Cu(OAc)$_2$ (500 mg, 2.8 mmol, 1.2 eq.). After stirring open to air for 16 h, the crude reaction mixture was filtered through Celite, rinsed with CH$_2$Cl$_2$, and concentrated. The crude residue was purified on silica gel eluting with 5% ethyl acetate in hexanes to afford 2,4-dichloro-5-fluoro-7-(4-methoxyphenyl)pyrrolo[2,3-d]pyrimidine (360 mg, 48% yield) as a fluffy white solid. LC-MS: 312.0 [M+H]$^+$; RT=1.58 min. $^1$H NMR (500 MHz, CDCl$_3$) δ ppm 3.79 (s, 3H), 6.96 (d, J=8.85 Hz, 2H), 7.12-7.22 (m, 1H), 7.35-7.46 (m, 2H).

Step 2: tert-Butyl (S)-(1-(2,4-dichloro-5-fluoro-7-(4-methoxyphenyl)-7H-pyrrolo[2,3-d]pyrimidin-6-yl)propan-2-yl)carbamate The title compound was prepared from 2,4-dichloro-5-fluoro-7-(4-methoxyphenyl)-7H-pyrrolo[2,3-d]pyrimidine according to the procedure described in Example 1 step 1. LC-MS: 469.0 [M+H]$^+$; RT=1.63 min.

Example 1 (Compound 10)

6-[(2S)-2-Aminopropyl]-2-chloro-5-fluoro-N-[(furan-2-yl)methyl]-7H-pyrrolo[2,3-d]pyrimidin-4-amine hydrochloride Step 1: tert-Butyl (S)-(1-(2,4-dichloro-5-fluoro-7-((2-(trimethylsilyl)ethoxy)methyl)-7H-pyrrolo[2,3-d]pyrimidin-6-yl)propan-2-yl)carbamate To a stirred solution of 2,4-dichloro-5-fluoro-7-((2-(trimethylsilyl)ethoxy)methyl)-7H-pyrrolo[2,3-d]pyrimidine (Intermediate 3, 631.6 mg, 1.88 mmol) in THF (4.0 mL) was added n-BuLi (2.5 M in hexanes, 1.0 mL, 2.5 mmol, 1.3 eq.) at −78° C. via syringe pump over 10 min. The reaction was stirred at −78° C. for 1 h before a solution of ter-butyl (S)-4-methyl-1,2,3-oxathiazolidine-3-carboxylate 2,2-dioxide (500 mg, 2.0 mmol, 1.1 eq.) in THF (5.0 mL) was added to the reaction mixture at −78° C. The reaction mixture was stirred at −78° C. for 1 h then warmed up to room temperature slowly overnight (keeping the −78° C. dry ice/acetone bath). TLC analysis indicated the formation of a new spot with presence of the starting material. After 16 h, the reaction was quenched with citric acid (aq. 1N, ~10 mL) then extracted with EtOAc (2×40 mL). The combined organic phases were dried over sodium sulfate and then concentrated to give the crude product which was purified by flash column chromatography (24 g, 0-20% EtOAc/hexanes) to afford tert-butyl N-[(1S)-2-[2,4-dichloro-5-fluoro-7-(2-trimethylsilylethoxymethyl)pyrrolo[2,3-d]pyrimidin-6-yl]-1-methyl-ethyl]carbamate (690.5 mg, 1.4 mmol, 75%) as a light green oil. $^1$H NMR (500 MHz, acetone-$d_6$) δ ppm −0.04 (s, 9H), 0.91-1.01 (m, 2H), 1.22-1.33 (m, 2H), 1.29 (s, 9H), 2.96-3.16 (m, 2H), 3.54-3.67 (m, 2H), 3.99-4.16 (m, 1H), 5.73-5.85 (m, 2H), 6.10 (br d, J=8.24 Hz, 1H).

Step 2: tert-Butyl (S)-(1-(2-chloro-5-fluoro-4-((furan-2-ylmethyl)amino)-7-((2-(trimethylsilyl)ethoxy)methyl)-7H-pyrrolo[2,3-d]pyrimidin-6-yl)propan-2-yl)carbamate To a stirred solution of tert-butyl N-[(1S)-2-[2,4-dichloro-5-fluoro-7-(2-trimethylsilylethoxymethyl)pyrrolo[2,3-d]pyrimidin-6-yl]-1-methyl-ethyl]carbamate (356.0 mg, 0.72 mmol) in 1,4-dioxane (3.5 mL) was added furfurylamine (110 mg, 0.1 mL, 1.12 mmol, 1.55 eq.) followed by DIPEA (163 mg, 0.22 mL, 1.25 mmol, 1.73 eq.) at room temperature. Then the reaction mixture was heated to 90° C. and stirred at 90° C. overnight. The reaction progress was monitored by LC-MS analysis of an aliquot of the mixture. After 16 h, LC-MS analysis of an aliquot of the mixture indicated the presence of <5% of the starting material. The reaction was quenched with water (~10 mL) then the mixture was extracted by EtOAc (2×40 mL). The combined organic layers were washed with water followed by brine (50 mL) and then dried over sodium sulfate. The volatiles were removed under reduced pressure to give crude product which was purified by flash column chromatography (0-15% EtOAc in hexanes) to afford tert-butyl (S)-(1-(2-chloro-5-fluoro-4-((furan-2-ylmethyl)amino)-7-((2-(trimethylsilyl)ethoxy)methyl)-7H-pyrrolo[2,3-d]pyrimidin-6-yl)propan-2-yl)carbamate (361.8 mg, 0.65 mmol, 91%) as an off-white solid. LC-MS: 554.5 [M+H]$^+$, 576.5, 578.5 [M+Na]$^+$; RT=1.83 min. $^1$H NMR (500 MHz, acetone-$d_6$) δ ppm −0.04 (s, 9H), 0.86-1.00 (m, 2H), 1.19 (d, J=6.73 Hz, 3H), 1.32 (s, 9H), 2.88 (dd, J=14.80, 6.56 Hz, 1H), 2.98 (dd, J=15.26, 7.02 Hz, 1H), 3.56 (br t, J=8.09 Hz, 2H), 3.90-4.02 (m, 1H), 4.62-4.84 (m, 2H), 5.57 (br d, J=11.29 Hz, 1H), 5.64 (d, J=11.29 Hz, 1H), 5.98 (br d, J=8.24 Hz, 1H), 6.26-6.41 (m, 2H), 7.11 (br s, 1H), 7.45 (dd, J=1.83, 0.92 Hz, 1H).

Step 3: tert-Butyl (S-(1-(2-chloro-5-fluoro-4-((furan-2-ylmethyl)amino)-7H-pyrrolo[2,3-d]pyrimidin-6-yl)propan-2-yl)carbamate To a stirred solution of tert-butyl N-[(1S)-2-[2-chloro-5-fluoro-4-(2-furylmethylamino)-7-(2-trimethylsilylethoxymethyl)pyrrolo[2,3-d]pyrimidin-6-yl]-1-methyl-ethyl]carbamate (361.8 mg, 0.65 mmol) in THF (0.50 mL) was added TBAF (1 M in THF, 3.50 mL, 3.50 mmol, 5.36 eq.) followed by ethylenediamine (110 mg, 0.12 mL, 1.7 mmol, 2.7 eq.) at room temperature. Then the reaction was heated to 65° C. and stirred at 65° C. for 60 h. The volatiles were removed under reduced pressure to give the crude product which was purified by flash column chromatography (0-40% EtOAc in hexanes doped with 10% DCM) to afford tert-butyl (S)-(1-(2-chloro-5-fluoro-4-((furan-2-ylmethyl)amino)-7H-pyrrolo[2,3-d]pyrimidin-6-yl)propan-2-yl)carbamate (141.5 mg, 0.33 mmol, 51%) as an off-white solid. LC-MS: 424.5, 426.5 [M+H]$^+$, 422.6, 424.6 [M−H]$^-$; RT=1.48 min. $^1$H NMR (500 MHz, acetone-$d_6$) δ ppm 1.17 (d, J=6.71 Hz, 3H), 1.33 (s, 9H), 2.80-2.89 (m, 2H), 3.89-3.98 (m, 1H), 4.78 (d, J=5.80 Hz, 2H), 5.93 (br s, 1H), 6.27-6.44 (m, 2H), 6.99 (br s, 1H), 7.45 (dd, J=1.83, 0.92 Hz, 1H), 10.48 (br s, 1H).

Step 4: 6-[(2S)-2-Aminopropyl]-2-chloro-5-fluoro-N-[(furan-2-yl)methyl]-7H-pyrrolo[2,3-d]pyrimidin-4-amine To a solution of tert-Butyl (S)-(1-(2-chloro-5-fluoro-4-((furan-2-ylmethyl)amino)-7H-pyrrolo[2,3-d]pyrimidin-6-yl)propan-2-yl)carbamate (141.5 mg, 0.33 mmol) in THF (1.5 mL) was added hydrochloric acid (4 M in 1,4-dioxane 1.0 mL, 4.0 mmol, 12 eq.) at room temperature. The reaction was stirred for 1.5 h at room temperature and then additional hydrochloric acid (4 M in 1,4-dioxane 1.0 mL, 4.0 mmol, 12 eq.) was added to the reaction mixture. The reaction was stirred for an additional 1.5 h at room temperature and LC-MS analysis indicated complete consumption of the starting material. The volatiles were removed under reduced pressure and the residue was diluted with ether (10 mL). The heterogeneous mixture was filtered, and washed with ether (~100 mL) to give an off-white solid which was dried under high vacuum overnight to afford (S)-6-(2-aminopropyl)-2-chloro-5-fluoro-N-(furan-2-ylmethyl)-7H-pyrrolo[2,3-d]pyrimidin-4-amine hydrochloride (111.2 mg, 0.31 mmol, 92%) as an off-white solid. LC-MS: 324.3, 326.3 [M+H]$^+$, 322.1, 324.0 [M−H]$^-$; RT=0.96. $^1$H NMR (500 MHz, DMSO-$d_6$) δ ppm 1.17 (d, J=6.41 Hz, 3H), 2.83 (dd, J=14.95, 8.24 Hz, 1H), 3.00 (br dd, J=14.65, 6.10 Hz, 1H), 3.44-3.58 (m, 1H), 4.62 (d, J=6.10 Hz, 2H), 6.26 (d, J=2.75 Hz, 1H), 6.39 (dd, J=3.05, 1.83 Hz, 1H), 7.49-7.63 (m, 1H), 7.92 (br s, 1H), 8.10 (br s, 3H), 11.75 (s, 1H).

Example 2 (Compound 24)

6-[(2S)-2-Aminopropyl]-2-chloro-5-fluoro-N-[(furan-2-yl)methyl]-7-methyl-7H-pyrrolo[2,3-d]pyrimidin-4-amine hydrochloride Step 1: tert-Butyl (S)-(1-(2-chloro-5-fluoro-4-((furan-2-ylmethyl)amino)-7-methyl-7H-pyrrolo[2,3-d]pyrimidin-6-yl)propan-2-yl)carbamate To a stirred solution of tert-butyl (S)-(1-(2-chloro-5-fluoro-4-((furan-2-ylmethyl)amino)-7H-pyrrolo[2,3-d]pyrimidin-6-yl)propan-2-yl)carbamate (Example 1 step 3, 170.0 mg, 0.40 mmol) in DMF (3.0 mL) was added cesium carbonate (140.0 mg, 0.43 mmol, 1.07 eq.) followed by iodomethane (2.0 M in tert-butyl methyl ether 0.22 mL, 0.44 mmol, 1.1 eq.) at room temperature. Then the reaction was stirred at room temperature overnight. The reaction progress was monitored by LC-MS analysis of an aliquot of the mixture and the LC-MS analysis indicated the complete consumption of starting material. The reaction was quenched with water (~5 mL) then extracted with EtOAc (2×40 mL). The combined organic phases were washed with water followed by brine (~30 mL). The volatiles were removed under reduced pressure to give the crude product which was purified by flash column chromatography (0-30% EtAOc in hexanes doped with 10% DCM) to afford tert-butyl (S)-(1-(2-chloro-5-fluoro-4-((furan-2-ylmethyl)amino)-7-methyl-7H-pyrrolo[2,3-d]pyrimidin-6-yl)propan-2-yl)carbamate (157.4 mg, 0.36 mmol, 90%) as an off-white solid. LC-MS: 438.5, 440.5 [M+H]$^+$; RT=1.55 min. $^1$H NMR (500 MHz, acetone-d$_6$) δ ppm 1.21 (d, J=7.02 Hz, 3H), 1.30 (s, 9H), 2.80-2.95 (m, 2H), 3.68 (s, 3H), 3.87-3.94 (m, 1H), 4.72-4.82 (m, 2H), 5.98 (br d, J=8.24 Hz, 1H), 6.30-6.36 (m, 2H) 6.99 (br s, 1H), 7.45 (s, 1H).

Step 2: 6-[(2S)-2-Aminopropyl]-2-chloro-5-fluoro-N-[(furan-2-yl)methyl]-7-methyl-7H-pyrrolo[2,3-d]pyrimidin-4-amine hydrochloride The title compound was prepared from tert-butyl (S)-(1-(2-chloro-5-fluoro-4-((furan-2-ylmethyl)amino)-7-methyl-7H-pyrrolo[2,3-d]pyrimidin-6-yl)propan-2-yl)carbamate according to the procedure described for Example 1 step 4. LC-MS: 338.2, 340.3 [M+H]$^+$; RT=1.02 min. $^1$H NMR (500 MHz, DMSO-d$_6$) δ ppm 1.20 (d, J=6.41 Hz, 3H), 2.95 (dd, J=15.11, 8.70 Hz, 1H), 3.11 (dd, J=15.11, 5.65 Hz, 1H), 3.29-3.40 (m, 1H), 3.59 (s, 3H), 4.62 (d, J=5.80 Hz, 2H), 6.26 (d, J=3.05 Hz, 1H), 6.39 (dd, J=3.05, 1.83 Hz, 1H), 7.56 (d, J=0.92 Hz, 1H), 7.99 (br s, 1H), 8.19 (br s, 3H).

The compounds below were prepared according to the procedures described for Example 1 or Example 2 starting from the indicated starting material.

Example 3 (Compound 6)

2-Chloro-5-fluoro-N-(furan-2-ylmethyl)-6-(2-(methylamino)ethyl)-7H-pyrrolo[2,3-d]pyrimidin-4-amine hydrochloride Step 1: tert-Butyl (2-(2,4-dichloro-5-fluoro-7-((2-(trimethylsilyl)ethoxy)methyl-7H-pyrrolo[2,3-d]pyrimidin-6-yl)ethyl)carbamate The title compound was prepared from Intermediate 3 according to the procedure described for Example 1, step 1.

Step 2: tert-Butyl (2-(2,4-dichloro-5-fluoro-7-((2-(trimethylsilyl)ethoxy)methyl)-7H-pyrrolo[2,3-d]pyrimidin-6-yl)ethyl)(methyl)carbamate To a stirred solution of tert-butyl N-[2-[2,4-dichloro-5-fluoro-7-(2-trimethylsilylethoxymethyl)pyrrolo[2,3-d]pyrimidin-6-yl]ethyl]carbamate (902.7 mg, 1.88 mmol) in THF (9.0 mL) and DMF (3.0 mL) was added NaH (60 mass %) in mineral oil (95.0 mg, 2.38 mmol, 1.26 eq.) at 0° C. The reaction was stirred for 20 min at 0° C. before iodomethane (342 mg, 0.15 mL, 2.41 mmol, 1.28 eq.) was added. The reaction was warmed to room temperature and then stirred at room temperature overnight. The reaction progress was monitored by LC-MS analysis of an aliquot of the mixture. After 16 h, the reaction was quenched by ammonium chloride (aq. sat., 40 mL) then extracted with diethyl ether (3×40 mL). The combined organic layers were dried over sodium sulfate and then concentrated to give crude product which was purified by a flash silica-gel column (24 g, 0-20% EtOAc in hexanes) to afford tert-butyl N-[2-[2,4-dichloro-

| Cpd | Starting Material/ Procedure | Spectral Data |
|---|---|---|
| 8 | Intermediate 1/ Example 1 | LC-MS: 292.3, 294.3 [M + H]$^+$, 290.1 [M − H]$^-$; RT 0.96 min. $^1$H NMR (500 MHz, DMSO-d$_6$) δ ppm 2.90-3.00 (m, 2H), 3.05-3.16 (m, 2H), 4.58-4.68 (m, 2H), 6.26-6.32 (m, 1H), 6.36-6.45 (m, 2H), 7.56-7.61 (m, 1H), 7.93 (br s, 3H), 8.18-8.29 (m, 1H), 11.72 (br s, 1H). |
| 13 | Intermediate 4/ Example 1 | LC-MS: 340.3, 342.3, 344.2 [M + H]$^+$, 338.2, 340.1 [M − H]$^-$; RT 1.09 min. $^1$H NMR (500 MHz, DMSO-d$_6$) δ ppm 1.14 (d, J = 6.41 Hz, 3H), 2.86 (dd, J = 14.50, 8.70 Hz, 1H), 3.03 (dd, J = 14.34, 5.80 Hz, 1H), 3.44-3.65 (m, 1H), 4.67 (d, J = 6.10 Hz, 2H), 6.27 (d, J = 3.05 Hz, 1H), 6.39 (dd, J = 3.36, 1.83 Hz, 1H), 7.41 (t, J = 5.95 Hz, 1H), 7.51-7.63 (m, 1H), 8.09 (br s, 3H), 12.24 (s, 1H). |
| 19 | Intermediate 5/ Example 1 | LC-MS: 384.1, 386.1, 388.1 [M + H]$^+$, 382.1, 384.2 [M − H]$^-$; RT 1.13 min. $^1$H NMR (500 MHz, DMSO-d$_6$) δ ppm 1.13 (d, J = 6.71 Hz, 3H), 2.85 (dd, J = 14.50, 9.00 Hz, 1H), 3.02 (dd, J = 14.34, 5.80 Hz, 1H), 3.45-3.63 (m, 1H), 4.70 (d, J = 6.10 Hz, 2H), 6.24-6.34 (m, 1H), 6.40 (dd, J = 3.36, 1.83 Hz, 1H), 7.17 (t, J = 5.95 Hz, 1H), 7.58 (dd, J = 1.83, 0.92 Hz, 1H), 8.08 (br s, 3H), 12.35 (s, 1H). |
| 23 | Intermediate 4/ Example 2 | LC-MS: 356.3 [M + H]$^+$; RT 1.00 min. $^1$H NMR (500 MHz, methanol-d$_4$) δ ppm 1.33 (d, J = 6.71 Hz, 3H), 3.04-3.26 (m, 2H), 3.54-3.65 (m, 1H), 3.70 (s, 3H), 4.72-4.77 (m, 2H), 6.21-6.39 (m, 2H), 7.42 (s, 1H); 3 NHs not observed. |
| 38 | Intermediate 3/ Example 2 | LC-MS: 355.3, 357.3 [M + H]$^+$; RT 1.19 min. $^1$H NMR (500 MHz, DMSO-d$_6$) δ ppm 1.22 (d, J = 6.41 Hz, 3H), 2.93-3.01 (m, 1H), 3.07-3.15 (m, 1H), 3.40-3.49 (m, 1H), 3.61 (s, 3H), 4.86-4.97 (m, 2H), 7.57-7.64 (m, 1H), 7.71-7.77 (m, 1H), 8.15 (br s, 3H), 8.38 (br t, J = 5.80 Hz, 1H). |

5-fluoro-7-(2-trimethylsilylethoxymethyl)pyrrolo[2,3-d]pyrimidin-6-yl]ethyl]-N-methyl-carbamate (418.0 mg, 0.85 mmol, 45%) as a pale yellow oil. $^1$H NMR (500 MHz, acetone-d$_6$) δ ppm −0.04 (s, 9H), 0.84-1.02 (m, 2H), 1.32 (s, 9H), 2.82-2.97 (br d, 3H), 3.12-3.26 (m, 2H), 3.54-3.67 (m, 4H), 5.76 (s, 2H).

Step 3-5: 2-Chloro-5-fluoro-N-(furan-2-ylmethyl)-6-(2-(methylamino)ethyl)-7H-pyrrolo[2,3-d]pyrimidin-4-amine hydrochloride The title compound was prepared from tert-butyl (2-(2,4-dichloro-5-fluoro-7-((2-(trimethylsilyl)ethoxy)methyl)-7H-pyrrolo[2,3-d]pyrimidin-6-yl)ethyl)(methyl)carbamate according to the procedures described for Example 1 steps 2-4. LC-MS: 324.3, 326.4 [M+H]$^+$, 322.2, 324.1 [M−H]$^-$; RT=0.99 min. $^1$H NMR (500 MHz, DMSO-d$_6$) δ ppm 2.52-2.57 (m, 3H), 3.04 (t, J=7.48 Hz, 2H), 3.14-3.23 (m, 2H), 4.62 (d, J=5.80 Hz, 2H), 6.25 (d, J=3.05 Hz, 1H), 6.38 (dd, 0.1=3.05, 1.83 Hz, 1H), 7.56 (d, J=0.92 Hz, 1H), 7.92 (br s, 1H), 8.98-9.16 (m, 2H), 11.82 (s, 1H).

The compounds below were prepared according to the procedure for Example 3 starting from the indicated starting material.

5-methyl-7H-pyrrolo[2,3-d]pyrimidin-6-yl)propan-2-yl)carbamate (202.7 mg, 0.34 mmol) and potassium carbonate (180 mg, 1.30 mmol, 3.87 eq.). To the solid mixture was added MeOH (2.5 mL), then the reaction mixture was heated to 60° C. and then stirred at 60° C. overnight. The reaction progress was monitored by LC-MS analysis of an aliquot of the mixture. The volatiles were removed under reduced pressure then the reaction mixture was diluted with DCM (~10 mL). The resulting mixture was quenched by HCl (1N, ~1.0 mL) then was extracted by DCM (5×20 mL) using a phase separator. The combined organic layers were dried over sodium sulfate. The volatiles were removed under reduced pressure to give crude product which was purified by flash column chromatography (12 g, 0-25% EtAOc in DCM) to afford tert-butyl (S)-(1-(2-chloro-4-((furan-2-ylmethyl)amino)-5-methyl-7H-pyrrolo[2,3-d]pyrimidin-6-yl)propan-2-yl)carbamate (102.0 mg, 0.24 mmol, 72%) as a light yellow foam. LC-MS: 420.3, 422.4 [M+H]$^+$, 418.4 [M−H]$^-$; RT=1.55 min. $^1$H NMR (500 MHz, DMSO-d$_6$) δ ppm 0.99 (br d, J=6.41 Hz, 3H), 1.12-1.35 (br s, 9H), 2.28 (s, 3H), 2.53-2.74 (m, 2H), 3.59-3.74 (m, 1H), 4.51-4.69 (m, 2H), 6.23 (br s, 1H), 6.37 (br d, J=1.83 Hz, 1H), 6.69 (brd, 4-8.24 Hz, 1H), 7.15 (br t, J=5.95 Hz, 1H), 7.55 (s, 1H), 11.30 (s, 4H).

| Cpd | Starting Material | Spectral Data |
| --- | --- | --- |
| 5 | Intermediate 1 | LC-MS: 323.2, 325.2 [M + H]$^+$, 321.2, 323.2 [M − H]$^-$; RT 0.79 min. $^1$H NMR (500 MHz, DMSO-d$_6$) δ ppm 2.56 (s, 3H), 2.99-3.08 (m, 2H), 3.14-3.27 (m, 2H), 4.86-4.97 (m, 2H), 6.35-6.46 (m, 1H), 7.57-7.65 (m, 1H), 7.71-7.79 (m, 1H), 8.70 (br s, 1H), 8.86 (br s, 2H), 11.85 (br s, 1H). |
| 9 | Intermediate 1 | LC-MS: 309.4, 311.4 [M + H]$^+$; RT 1.02 min. $^1$H NMR (500 MHz, DMSO-d$_6$) δ ppm 2.96-3.03 (m, 2H), 3.14-3.23 (m, 2H), 4.60-4.66 (m, 2H), 6.27-6.32 (m, 1H), 6.37-6.43 (m, 2H), 7.56-7.61 (m, 1H), 8.21-8.30 (m, 1H), 8.64 (br s, 2H), 11.74 (br s, 1H). |
| 17 | Intermediate 4 | LC-MS: 340.3, 342.3, 344.2 [M + H]$^+$, 338.2, 340.1 [M − H]$^-$; RT 1.00 min. $^1$H NMR (500 MHz, DMSO-d$_6$) δ ppm 2.56 (s, 3H), 2.97-3.12 (m, 2H), 3.14-3.22 (m, 2H), 4.67 (d, J = 6.10 Hz, 2H), 6.19-6.33 (m, 1H), 6.39 (dd, J = 3.36, 1.83 Hz, 1H), 7.41 (t, J = 5.95 Hz, 1H), 7.57 (dd, J = 1.83, 0.92 Hz, 1H), 8.93 (br s, 2H), 12.27 (s, 1H). |
| 18 | Intermediate 5 | LC-MS: 382.1, 384.1, 386.2 [M − H]$^-$; RT 1.11 min. $^1$H NMR (500 MHz, DMSO-d$_6$) δ ppm 2.57 (s, 3H), 2.95-3.10 (m, 2H), 3.11-3.29 (m, 2H), 4.70 (d, J = 5.80 Hz, 2H), 6.21-6.34 (m, 1H), 6.40 (dd, J = 3.05, 1.83 Hz, 1H), 7.18 (t, J = 5.95 Hz, 1H), 7.48-7.68 (m, 1H), 8.82 (br s, 2H), 12.37 (s, 1H). |

Example 4 (Compound 33)

6-[(2S)-2-Aminopropyl]-2-chloro-N-[(furan-2-yl)methyl]-5-methyl-7H-pyrrolo[2,3-d]pyrimidin-4-amine hydrochloride Steps 1-2: tert-Butyl (S)-(1-(2-chloro-4-((furan-2-ylmethyl)amino)-7-(mesitylsulfonyl)-5-methyl-7H-pyrrolo[2,3-d]pyrimidin-6-yl)propan-2-yl)carbamate The title compound was prepared from Intermediate 6 according to the procedures described for Example 1, steps 1-2.

Step 3: tert-Butyl (S)-(1-(2-chloro-4-((furan-2-ylmethyl)amino)-5-methyl-7H-pyrrolo[2,3-d]pyrimidin-6-yl)propan-2-yl)carbamate To a 20 mL scintillation vial was added tert-butyl (S)-(1-(2-chloro-4-((furan-2-ylmethyl)amino)-7-(mesitylsulfonyl)-

Step 4: 6-[(2S)-2-Aminopropyl]-2-choro-N-[(furan-2-yl)methyl]-5-methyl-7H-pyrrolo[2,3-d]pyrimidin-4-amine The title compound was prepared from tert-butyl (S)-(1-(2-chloro-4-((furan-2-ylmethyl)amino)-5-methyl-7H-pyrrolo[2,3-d]pyrimidin-6-yl)propan-2-yl)carbamate according to the procedure described for Example 1 step 4. LC-MS: 320.3, 322.3 [M+H]$^+$, 318.2 [M−H]$^-$; RT=1.06 min. $^1$H NMR (500 MHz, DMSO-d$_6$) δ ppm 1.12 (d, J=6.41 Hz, 3H), 2.30 (s, 3H), 2.75 (dd, J=14.50, 8.39 Hz, 1H), 2.96 (dd, J=14.65, 6.10 Hz, 3H), 3.35-3.46 (m, 1H), 4.53-4.70 (m, 2H), 6.25 (d, J=3.36 Hz, 1H), 6.32-6.44 (m, 1H), 7.27 (br, J=5.95 Hz, 1H), 7.56 (s, 1H), 7.94 (br s, 3H), 11.51 (s, (H).

The compounds below were prepared according to the procedure for Example 4 starting from the indicated starting material.

| Cpd | Starting Material | Spectral Data |
|---|---|---|
| 11 | Intermediate 7 | LC-MS: 334.4 [M + H]$^+$, 332.5 [M − H]$^-$; RT 1.01 min. $^1$H NMR (500 MHz, DMSO-d$_6$) δ ppm 0.87-1.04 (m, 6H), 1.89 (td, J = 6.87, 4.27 Hz, 1H), 2.85-2.99 (m, 2H), 3.24-3.44 (m, 1H), 4.55-4.67 (m, 2H), 6.22-6.35 (m, 1H), 6.36-6.49 (m, 2H), 7.58 (dd, J = 1.83, 0.92 Hz, 1H), 7.98 (br s, 3H), 8.27 (br t, J = 5.19 Hz, 1H), 11.74 (s, 1H). |
| 12 | Intermediate 7 | LC-MS: 345.4 [M + H]$^+$, 343.3 [M − H]$^-$; RT 0.78 min. $^1$H NMR (500 MHz, DMSO-d$_6$) δ ppm 0.91-1.03 (m, 6H), 1.87-1.95 (m, 1H), 2.90-3.03 (m, 2H), 3.34-3.39 (m, 1H), 4.85-4.96 (m, 2H), 6.49-6.55 (m, 1H), 7.91-7.99 (m, 2H), 8.03-8.13 (m, 3H), 8.73-8.82 (m, 1H), 8.83-8.89 (m, 2H), 11.85-11.93 (m, 1H). |
| 14 | Intermediate 2 | LC-MS: 352.3 [M + H]$^+$, 350.5 [M − H]$^-$; RT 1.08 min. $^1$H NMR (500 MHz, DMSO-d$_6$) δ ppm 0.93 (d, J = 7.02 Hz, 3H), 0.98 (d, J = 7.02 Hz, 3H), 1.87 (td, J = 6.94, 4.43 Hz, 1H), 2.84-3.00 (m, 2H), 3.33-3.38 (m, 1H), 4.54-4.68 (m, 2H), 6.19-6.33 (m, 1H), 6.39 (dd, J = 3.36, 1.83 Hz, 1H), 7.56 (dd, J = 1.83, 0.61 Hz, 1H), 7.75-7.94 (m, 1H), 7.95-8.10 (m, 3H), 11.74 (s, 1H). |
| 15 | Intermediate 2 | LC-MS: 363.4 [M + H]$^+$, 361.5 [M − H]$^-$; RT 0.71 min. $^1$H NMR (500 MHz, DMSO-d$_6$) δ ppm 0.94 (d, J = 7.02 Hz, 3H), 1.00 (d, J = 7.02 Hz, 3H), 1.88 (td, J = 6.87, 4.27 Hz, 1H), 2.97 (br d, J = 6.71 Hz, 2H), 3.29-3.40 (m, 1H), 4.88 (br d, J = 6.10 Hz, 2H), 7.94 (d, J = 6.41 Hz, 2H), 8.07-8.20 (m, 3H), 8.27 (br t, J = 5.80 Hz, 1H), 8.83 (d, J = 6.41 Hz, 2H), 11.93 (s, 1H). |
| 16 | Intermediate 7 | LC-MS: 306.1, 308.1 [M + H]$^+$; RT 1.42 min. $^1$H NMR (400 MHz, DMSO-d$_6$) δ ppm 1.18 (d, J = 6.70 Hz, 3H), 2.77-2.88 (m, 1H), 2.99-3.10 (m, 1H), 3.45-3.56 (m, 1H), 4.60-4.66 (m, 2H), 6.29-6.33 (m, 1H), 6.38-6.44 (m, 2H), 7.56-7.62 (m, 1H), 8.17 (br s, 2H), 8.29 (br s, 1H), 11.78 (br s, 1H). |
| 20 | Intermediate 7 | LC-MS: 317.0, 319.0 [M + H]$^+$; RT 0.74 min. $^1$H NMR (400 MHz, DMSO-d$_6$) δ ppm 0.98 (d, J = 6.70 Hz, 3H), 1.70 (s, 2H), 2.55-2.63 (m, 2H), 3.07-3.17 (m, 1H), 4.63-4.70 (m, 2H), 6.27-6.35 (m, 1H), 6.61-6.86 (m, 1H), 7.29-7.36 (m, 2H), 8.30-8.37 (m, 1H), 8.47-8.53 (m, 2H). |
| 21 | Intermediate 8 | LC-MS: 354.3 [M + H]$^+$, 352.4 [M − H]$^-$; RT 1.03 min. $^1$H NMR (500 MHz, DMSO-d$_6$) δ ppm 0.90 (t, J = 7.20 Hz, 3H), 1.54 (quin, J = 7.17 Hz, 2H), 2.89-3.06 (m, 2H), 3.40-3.47 (m, 1H), 4.61-4.72 (m, 2H), 6.27 (d, J = 3.05 Hz, 1H), 6.39 (dd, J = 3.05, 1.83 Hz, 1H), 7.40 (t, J = 5.95 Hz, 1H), 7.57 (s, 1H), 8.03-8.19 (m, 3H), 12.26 (s, 1H). |
| 22 | Intermediate 7 | LC-MS: 323.2, 325.2 [M + H]$^+$, 321.1, 323.2 [M − H]$^-$; RT 0.91 min. $^1$H NMR (500 MHz, methanol-d$_4$) δ ppm 1.34 (d, J = 6.71 Hz, 3H), 2.95-3.15 (m, 2H), 3.56-3.67 (m, 1H), 5.07 (s, 2H), 6.43 (s, 1H), 7.61 (d, J = 3.05 Hz, 1H), 7.82 (d, J = 3.05 Hz, 1H); 4 NHs not observed. |
| 25 | Intermediate 7 | LC-MS: 322.1, 324.3 [M + H]$^+$, 320.1, 322.2 [M − H]$^-$; RT 1.00 min. $^1$H NMR (500 MHz, methanol-d$_4$) δ ppm 1.33 (d, J = 6.71 Hz, 3H), 2.92-3.06 (m, 2H), 3.53-3.68 (m, 1H), 4.90 (s, 2H), 6.39 (s, 1H), 6.94 (dd, J = 5.04, 3.51 Hz, 1H), 7.06 (d, J = 3.05 Hz, 1H), 7.16-7.37 (m, 1H); 4 NHs not observed. |
| 26 | Intermediate 7 | LC-MS: 320.3 [M + H]$^+$, 318.1 [M − H]$^-$; RT 1.01 min. $^1$H NMR (500 MHz, DMSO-d$_6$) δ ppm 0.92 (t, J = 7.63 Hz, 3H), 1.50-1.61 (m, 2H), 2.87-3.03 (m, 2H), 3.28-3.42 (m, 1H), 4.62 (br d, J = 4.88 Hz, 2H), 6.30 (d, J = 3.05 Hz, 1H), 6.35-6.48 (m, 2H), 7.59 (d, J = 0.92 Hz, 1H), 8.15 (br s, 3H), 8.21-8.36 (m, 1H), 11.77 (s, 1H). |
| 27 | Intermediate 7 | LC-MS: 307.2, 309.3 [M + H]$^+$, 305.4, 307.4 [M − H]$^-$; RT 0.80 min. $^1$H NMR (500 MHz, methanol-d$_4$) δ ppm 1.33 (br d, J = 6.41 Hz, 3H), 2.93-3.07 (m, 2H), 3.54-3.67 (m, 1H), 4.95 (s, 2H), 6.43 (s, 1H), 7.16 (br s, 1H), 7.89 (br s, 1H); 4 NHs not observed. |
| 28 | Intermediate 11 | LC-MS: 362.4, 364.3 [M + H]$^+$, 360.2, 362.1 [M − H]$^-$; RT 1.17 min. $^1$H NMR (500 MHz, methanol-d$_4$) δ ppm 0.90 (t, J = 7.32 Hz, 3H), 1.27-1.41 (m, 4H), 1.43-1.57 (m, 2H), 2.79 (br t, J = 7.48 Hz, 2H), 2.93 (dd, J = 14.60, 8.20 Hz, 1H), 3.10 (dd, J = 14.50, 6.30 Hz, 1H), 3.34-3.54 (m, 1H), 3.62 (br d, J = 6.41 Hz, 1H), 4.82 (s, 2H), 6.30-6.41 (m, 2H), 7.40-7.47 (m, 1H); 4 NHs not observed. |
| 29 | Intermediate 7 | LC-MS: 348.4 [M + H]$^+$, 346.4 [M − H]$^-$; RT 1.07 min. $^1$H NMR (500 MHz, DMSO-d$_6$) δ ppm 1.00 (s, 9H), 2.81 (m, 1H), 3.06 (m, 1H), 3.20 (m, 1H), 4.55-4.73 (m, 2H), 6.30 (d, J = 3.05 Hz, 1H), 6.40 (dd, J = 3.05, 1.83 Hz, 1H), 6.47 (m, 1H), 7.58 (m, 1H), 7.85 (br s, 3H), 8.28 (br s, 1H), 11.77 (s, 1H). |

| Cpd | Starting Material | Spectral Data |
|---|---|---|
| 30 | Intermediate 7 | LC-MS: 306.3, 308.3 [M + H]⁺, 304.3, 306.4 [M − H]⁻; RT 1.01 min. ¹H NMR (500 MHz, methanol-d₄) δ ppm 1.33 (d, J = 6.71 Hz, 3H), 2.93-3.06 (m, 2H), 3.54-3.67 (m, 1H), 4.57 (s, 2H), 6.42 (s, 1H), 6.44-6.53 (m, 1H), 7.43 (t, J = 1.68 Hz, 1H), 7.50 (s, 1H); 4 NHs not observed. |
| 31 | Intermediate 7 | LC-MS: 335.3, 337.3 [M + H]⁺, 333.4, 335.5 [M − H]⁻; RT 0.83 min. ¹H NMR (500 MHz, methanol-d₄) δ ppm 1.35 (d, J = 6.41 Hz, 3H), 2.98 (dd, J = 14.80, 7.48 Hz, 1H), 3.08 (dd, J = 14.95, 6.71 Hz, 1H), 3.55-3.70 (m, 1H), 4.94 (s, 2H), 6.48 (s, 1H), 7.76 (br t, J = 5.49 Hz, 1H), 8.49 (br s, 1H), 8.71 (br s, 1H); 4 NHs not observed. |
| 32 | Intermediate 7 | LC-MS: 348.3 [M + H]⁺, 346.7 [M − H]⁻; RT 1.05 min. ¹H NMR (500 MHz, DMSO-d₆) δ ppm 0.87 (t, J = 7.32 Hz, 3H), 0.97 (d, J = 6.71 Hz, 3H), 1.03-1.16 (m, 1H), 1.36-1.53 (m, 1H), 1.59-1.76 (m, 1H), 2.83-2.97 (m, 2H), 3.34-3.47 (m, 1H), 4.55-4.69 (m, 2H), 6.30 (d, J = 3.05 Hz, 1H), 6.35-6.50 (m, 2H), 7.58 (s, 1H), 8.05 (br s, 3H), 8.28 (br s, 1H), 11.79 (s, 1H). |
| 36 | Intermediate 2 | LC-MS: 341.1 [M + H]⁺, 363.1, 365.1 [M + Na]⁺; RT 0.93 min. ¹H NMR (500 MHz, methanol-d₄) δ ppm 1.35 (d, J = 6.41 Hz, 3H), 2.98 (dd, J = 14.95, 7.02 Hz, 1H), 3.07 (br dd, J = 15.11, 6.87 Hz, 1H), 3.59-3.66 (m, 1H), 5.06 (s, 2H), 7.57 (d, J = 3.36 Hz, 1H), 7.78 (d, J = 3.36 Hz, 1H); 4 NHs not observed. |
| 40 | Intermediate 2 | LC-MS: 340.3, 342.3 [M + H]⁺, 338.4 [M − H]⁻; RT 1.03 min. ¹H NMR (500 MHz, methanol-d₄) δ ppm 1.33 (d, J = 6.41 Hz, 3H), 2.91-2.99 (m, 1H), 3.00-3.08 (m, 1H), 3.55-3.63 (m, 1H), 4.89 (s, 2H), 6.90-6.96 (m, 1H), 7.04-7.09 (m, 1H), 7.23-7.27 (m, 1H); 4 NHs not observed. |
| 44 | Intermediate 2 | LC-MS: 338.3, 340.3 [M + H]⁺, 336.1, 338.1 [M − H]⁻; RT 1.07 min. ¹H NMR (500 MHz, methanol-d₄) δ ppm 1.03-1.10 (m, 3H), 1.62-1.79 (m, 2H), 2.95-3.09 (m, 2H), 3.40-3.50 (m, 1H), 4.69-4.78 (m, 2H), 6.28-6.33 (m, 1H), 6.33-6.36 (m, 1H), 7.39-7.43 (m, 1H); 4 NHs not observed. |
| 50 | Intermediate 2 | LC-MS: 334.2, 336.3 [M + H]⁺, 332.2, 334.2 [M − H]⁻; RT 1.21 min. ¹H NMR (500 MHz, DMSO-d₆) δ ppm 1.18 (d, J = 6.41 Hz, 3H), 2.79-2.88 (m, 1H), 2.94-3.06 (m, 1H), 3.45-3.56 (m, 1H), 4.60-4.69 (m, 2H), 7.20-7.27 (m, 1H), 7.28-7.39 (m, 4H), 8.03 (br s, 1H), 8.11 (br s, 3H), 11.73 (s, 1H). |
| 52 | Intermediate 2 | LC-MS: 352.3, 354.3 [M + H]⁺, 350.2 [M − H]⁻; RT 1.24 min. ¹H NMR (500 MHz, methanol-d₄) δ ppm 1.34 (d, J = 6.71 Hz, 3H), 2.93-3.00 (m, 1H), 3.01-3.08 (m, 1H), 3.56-3.65 (m, 1H), 4.81 (s, 2H), 7.04-7.15 (m, 2H), 7.24-7.33 (m, 1H), 7.38-7.46 (m, 1H); 4 NHs not observed. |
| 54 | Intermediate 2 | LC-MS: 335.3, 337.3 [M + H]⁺, 333.2 [M − H]⁻; RT 0.87 min. ¹H NMR (500 MHz, methanol-d₄) δ ppm 1.35 (d, J = 6.41 Hz, 3H), 2.94-3.03 (m, 1H), 3.08-3.16 (m, 1H), 3.60-3.68 (m, 1H), 5.00-5.10 (m, 2H), 7.94 (t, J = 6.71 Hz, 1H), 8.05 (d, J = 8.24 Hz, 1H), 8.53 (td, J = 7.93, 1.22 Hz, 1H), 8.75 (d, J = 5.19 Hz, 1H); 4 NHs not observed. |
| 56 | Intermediate 2 | LC-MS: 335.3, 337.3 [M + H]⁺, 333.2, 335.1 [M − H]⁻; RT 0.77 min. ¹H NMR (500 MHz, methanol-d₄) δ ppm 1.33 (d, J = 6.41 Hz, 3H), 2.92-3.01 (m, 1H), 3.05-3.12 (m, 1H), 3.57-3.65 (m, 1H), 4.87-4.91 (m, 2H), 7.95-8.05 (m, 1H), 8.54-8.63 (m, 1H), 8.69-8.78 (m, 1H), 8.87-8.97 (m, 1H); 4 NHs not observed. |
| 58 | Intermediate 2 | LC-MS: 354.1, 356.2 [M + H]⁺, 352.2, 354.2 [M − H]⁻; RT 1.09 min. ¹H NMR (500 MHz, methanol-d₄) δ ppm 1.09 (t, J = 7.63 Hz, 3H), 1.60-1.81 (m, 2H), 2.92-3.14 (m, 2H), 3.42-3.49 (m, 1H), 4.89-4.96 (m, 2H), 6.92-7.02 (m, 1H), 7.02-7.17 (m, 1H), 7.18-7.39 (m, 1H); 4 NHs not observed. |
| 59 | Intermediate 2 | LC-MS: 355.1, 357.1 [M + H]⁺, 353.2, 355.2 [M − H]⁻; RT 0.89 min. ¹H NMR (500 MHz, methanol-d₄) δ ppm 1.10 (t, J = 7.48 Hz, 3H), 1.62-1.82 (m, 2H), 3.02-3.13 (m, 2H), 3.41-3.54 (m, 1H), 5.13 (s, 2H), 7.72 (d, J = 3.40 Hz, 1H), 7.91 (d, J = 3.40 Hz, 1H); 4 NHs not observed. |
| 61 | Intermediate 7 | LC-MS: 323.0, 325.1 [M + H]⁺; RT 1.25 min. ¹H NMR (400 MHz, DMSO-d₆) δ ppm 0.99 (d, J = 6.36 Hz, 3H), 2.52-2.68 (m, 2H), 3.08-3.20 (m, 1H), 4.77 (d, J = 5.62 Hz, 2H), 6.32 (s, 1H), 6.74 (s, 1H), 7.45 (s, 1H), 8.24 (br t, J = 5.87 Hz, 1H), 9.07 (s, 1H); 2 NHs not observed. |

| Cpd | Starting Material | Spectral Data |
|---|---|---|
| 62 | Intermediate 13 | LC-MS: 368.3, 370.3 [M + H]$^+$; RT 0.94 min. $^1$H NMR (500 MHz, DMSO-d$_6$) δ 0.97 (d, J = 6.10 Hz, 3H), 2.52-2.67 (m, 2H), 3.08-3.17 (m, 1H), 4.60 (br d, J = 5.80 Hz, 2H), 6.22-6.32 (m, 1H), 6.38 (br s, 1H), 7.56 (s, 1H), 7.79 (br s, 1H); 3 NHs not observed. |

Example 5 (Compound 37)

6-[(2R)-2-Amino-3-methoxypropyl]-2-chloro-5-fluoro-N-[(furan-2-yl)methyl]-7-methyl-7H-pyrrolo[2,3-d]pyrimidin-4-amine hydrochloride

Step 1: tert-Butyl (R)-(6-(2-((tert-butoxycarbonyl)amino)-3-((tert-butyldimethylsilyl)oxy)propyl)-2-chloro-5-fluoro-7-(mesitylsulfonyl)-7H-pyrrolo[2,3-d]pyrimidin-4-yl)(furan-2 ylmethyl)carbamate The title compound was prepared from Intermediate 9 according to the procedure described for Example 1 step 1.

Step 2: tert-Butyl (R)-(6-(2-((tert-butoxycarbonyl)amino)-3-hydroxypropyl)-2-chloro-5-fluoro-7H-pyrrlo[2,3-d]pyrimidin-4-yl)(furan-2-ylmethyl)carbamate To a stirred solution of tert-butyl N-[6-[(2R)-2-(tert-butoxycarbonylamino)-3-[tert-butyl(dimethyl)silyl]oxy-propyl]-2-chloro-5-fluoro-7-(2,4,6-trimethylphenyl)sulfonyl-pyrrolo[2,3-d]pyrimidin-4-yl]-N-(2-furylmethyl)carbamate (1.01 g, 1.20 mmol) in THF (8.0 mL) was added TBAF (1 M in THF 2.0 mL, 2.0 mmol, 1.66 eq.) at 0° C. The reaction was stirred at 0° C. for 45 min and the reaction progress was monitored by LC-MS analysis of an aliquot of the mixture. The volatiles were removed under reduced pressure to give the crude product which was purified by flash column chromatography (40 g, 0-50% EtOAc/hexanes) to afford tert-butyl N-[6-[(2R)-2-(tert-butoxycarbonylamino)-3-hydroxy-propyl]-2-chloro-5-fluoro-7H-pyrrolo[2,3-d]pyrimidin-4-yl]-N-(2-furylmethyl)carbamate (136.0 mg, 0.25 mmol, 21%) as an off-white foam. LC-MS: 562.4, 564.3 [M+Na]$^+$, 538.3, 540.2 [M−H]$^−$; RT=1.64 min. $^1$H NMR (500 MHz, acetone-d$_6$) δ ppm 1.31 (s, 9H). 1.44 (s, 9H), 2.35 (br s, 1H), 2.98 (br dd, J=14.95, 8.54 Hz, 1H), 3.12 (br dd, J=14.95, 5.80 Hz, 1H), 3.63 (br s, 2H), 3.94-4.02 (m, 1H), 5.07-5.22 (m, 2H), 5.89 (br d, J=7.63 Hz, 1H), 6.27 (dd, J=3.20, 0.70 Hz, 1H), 6.31 (dd, J=3.20, 1.83 Hz, 1H), 7.39 (dd, J=1.68, 0.76 Hz, 1H), 10.97 (br s, 1H).

Step 3: tert-Butyl (R)-(6-(2-((tert-butoxycarbonyl)amino)-3-methoxypropyl-2-chloro-5-fluoro-7-methyl-7H-pyrrolo[2,3-d]pyrimidin-4-yl(furan-2-ylmethyl)carbamate The title compound was prepared from tert-butyl (R)-(6-(2-((tert-butoxycarbonyl)amino)-3-hydroxypropyl)-2-chloro-5-fluoro-7H-pyrrolo[2,3-d]pyrimidin-4-yl)(furan-2-ylmethyl)carbamate according to the procedure described for Example 2 step 1.

Step 4: 6-[(2R)-2-Amino-3-methoxypropyl]-2-chloro-5-fluoro-N-[(furan-2-yl)methyl]-7-methyl-7H-pyrrolo[2,3-d]pyrimidin-4-amine The title compound was prepared from tert-butyl (R)-(6-(2-((tert-butoxycarbonyl)amino)-3-methoxypropyl)-2-chloro-5-fluoro-7-methyl-7H-pyrolo[2,3-d]pyrimidin-4-yl)(furan-2-ylmethyl)carbamate according to the procedure described for Example 1 step 4. LC-MS: 371.4 [M+H]$^+$; RT=1.17 min. $^1$H NMR (500 MHz, DMSO-d) δ ppm 2.99 (dd, J=5.96, 15.20 Hz, 1H), 3.07 (dd, J=8.60, 15.20 Hz, 1H), 3.33 (s, 3H), 3.35-3.55 (m, 3H), 3.58 (s, 3H), 4.63 (br d, J=7.93 Hz, 2H), 6.26 (br d, J=3.36 Hz, 1H), 6.33-6.48 (m, 1H), 7.57 (s, 1H), 8.01 (br s, 1H), 8.08 (br s, 3H).

The compounds below were prepared according to the procedure for Example 5 starting from the indicated starting material.

| Cpd | Starting Material | Spectral Data |
|---|---|---|
| 35 | Intermediate 10 | LC-MS: 334.2, 336.2 [M + H]$^+$; RT 1.01 min. $^1$H NMR (500 MHz, methanol-d$_4$) δ ppm 1.29 (d, J = 6.41 Hz, 3H), 2.40 (s, 3H), 2.95-3.10 (m, 2H), 3.47-3.54 (m, 1H), 3.65 (s, 3H), 4.69-4.77 (m, 2H), 6.26-6.37 (m, 2H), 7.40 (d, J = 1.22 Hz, 1H); 3 NHs not observed. |
| 39 | Intermediate 9 | LC-MS: 354.3 [M + H]$^+$; RT 1.24 min. $^1$H NMR (500 MHz, methanol-d$_4$) δ ppm 3.02-3.11 (m, 1H), 3.13-3.23 (m, 2H), 3.50-3.56 (m, 1H), 3.57-3.62 (m, 1H), 3.66 (s, 3H), 3.75-3.81 (m, 1H), 4.68-4.76 (m, 2H), 6.28-6.31 (m, 1H), 6.32-6.36 (m, 1H), 7.39-7.42 (m, 1H); 3 NHs not observed. |
| 42 | Intermediate 9 | LC-MS: 352.4, 354.4 [M + H]$^+$; RT 1.24 min. $^1$H NMR (500 MHz, methanol-d$_4$) δ ppm 1.31 (t, J = 7.17 Hz, 3H), 1.35 (d, J = 6.41 Hz, 3H), 3.00-3.12 (m, 2H), 3.53-3.63 (m, 1H), 4.08-4.23 (m, 2H), 4.68-4.76 (m, 2H), 6.28-6.32 (m, 1H), 6.32-6.37 (m, 1H), 7.39-7.43 (m, 1H); 3 NHs not observed. |

| Cpd | Starting Material | Spectral Data |
|---|---|---|
| 45 | Intermediate 9 | LC-MS: 352.3 [M + H]$^+$; RT 1.14 min. $^1$H NMR (500 MHz, methanol-d$_4$) δ ppm 1.08 (s, 3H), 1.64-1.74 (m, 1H), 1.74-1.84 (m, 1H), 2.99-3.07 (m, 1H), 3.12-3.18 (m, 1H), 3.40-3.47 (m, 1H), 3.65 (s, 3H), 4.68-4.77 (m, 2H), 6.28-6.32 (m, 1H), 6.33-6.36 (m, 1H), 7.39-7.43 (m, 1H); 3 NHs not observed. |

Example 6 (Compound 41)

6-[(2S)-2-Amninopropyl]-2-chloro-5-fluoro-N-[(3-fluoropyridin-4-yl)methyl]-7-methyl-7H-pyrrolo[2,3-d]pyrimidin-4-amine dihydrochloride

Step 1: tert-Butyl (S)-(1-(2,4-dichloro-5-fluoro-7-(mesitylsulfonyl)-7H-pyrrolo[2,3-d]pyrimidin-6-yl)propan-2-yl)carbamate The title compound was prepared from Intermediate 2 according to the procedure described for Example 1 step 1.

Step 2: tert-Butyl (S)-(1-(2,4-dichloro-5-fluoro-7H-pyrrolo[2,3-d]pyrimidin-6-yl)propan-2-yl)carbamate The title compound was prepared from tert-butyl (S)-(1-(2,4-dichloro-5-fluoro-7-(mesitylsulfonyl)-7H-pyrrolo[2,3-d]pyrimidin-6-yl)propan-2-yl)carbamate according to the procedure described for Example 5 step 2.

Step 3: tert-Butyl (S)-(1-(2,4-dichloro-5-fluoro-7-methyl-7H-pyrrolo[2,3-d]pyrimidin-6-yl)propan-2-yl)carbamate The title compound was prepared from tert-butyl (S)-(1-(2,4-dichloro-5-fluoro-7H-pyrrolo[2,3-d]pyrimidin-6-yl)propan-2-yl)carbamate according to the procedures described for Example 2 step 1.

Step 4: tert-Butyl (S)-(1-(2-chloro-5-fluoro-4-(((3-fluoropyridin-4-yl)methyl)amino)-7-methyl-7H-pyrrolo[2,3-d]pyrimidin-6-yl)propan-2-yl)carbamate The title compound was prepared from tert-butyl (S)-(1-(2,4-dichloro-5-fluoro-7-methyl-7H-pyrrolo[2,3-d]pyrimidin-6-yl)propan-2-yl)carbamate according to the procedure described for Example 1 step 2.

Step 5: 6-[(2S)-2-Aminopropyl]-2-chloro-5-fluoro-N-[(3-fluoropyridin-4-yl)methyl]-7-methyl-7H-pyrrolo[2,3-d]pyrimidin-4-amine dihydrochloride The title compound was prepared from tert-butyl (S)-(1-(2-chloro-5-fluoro-4-(((3-fluoropyridin-4-yl)methyl)amino)-7-methyl-7H-pyrrolo[2,3-d]pyrimidin-6-yl)propan-2-yl)carbamate according to the procedure described for Example 1 step 4. LC-MS: 367.4, 369.4 [M+H]$^+$; RT=0.92 min. $^1$H NMR (500 MHz, DMSO-d$_6$) δ ppm 1.22 (br d, J=6.41 Hz, 2H), 2.97 (br dd, J=14.95, 8.85 Hz, 1H), 3.13 (br dd, J=14.95, 5.49 Hz, 1H), 3.29-3.50 (m, 1H), 3.60 (s, 3H), 4.75 (d, J=6.10 Hz, 2H), 7.41 (t, J=5.80 Hz, 1H), 8.21 (br s, 3H), 8.26 (br s, 1H), 8.40 (d, J=5.19 Hz, 1H), 8.61 (d, J=1.83 Hz, 1H).

The compounds below were prepared according to the procedure for Example 6 starting from the indicated starting material.

| Cpd | Starting Material | Spectral Data |
|---|---|---|
| 43 | Intermediate 2 | LC-MS: 349.3, 351.3 [M + H]$^+$; RT 1.14 min. $^1$H NMR (500 MHz, methanol-d$_4$) δ ppm 1.37 (d, J = 6.71 Hz, 3H), 3.04-3.12 (m, 1H), 3.12-3.20 (m, 1H), 3.56-3.65 (m, 1H), 3.68 (s, 3H), 5.01 (s, 2H), 8.02-8.11 (m, 2H), 8.73-8.83 (m, 2H); 3 NHs not observed. |
| 48 | Intermediate 2 | LC-MS: 355.3, 357.3 [M + H]$^+$; RT 0.91 min. $^1$H NMR (500 MHz, DMSO-d$_6$) δ ppm 1.20 (d, J = 6.10 Hz, 3H), 2.90-3.00 (m, 1H), 3.07-3.16 (m, 1H), 3.34-3.47 (m, 1H), 3.60 (s, 3H), 4.78-4.85 (m, 2H), 7.86 (s, 1H), 8.23 (br s, 4H), 9.00 (s, 1H). |
| 49 | Intermediate 2 | LC-MS: 354.2, 356.1 [M + H]$^+$; RT 1.16 min. $^1$H NMR (500 MHz, DMSO-d$_6$) δ 1.20 (d, J = 6.41 Hz, 3H), 2.95 (br dd, J = 14.95, 8.85 Hz, 1H), 3.11 (br dd, J = 15.11, 5.65 Hz, 1H), 3.36-3.46 (m, 1H), 3.59 (s, 3H), 4.75-4.79 (m, 2H), 6.93-6.97 (m, 1H), 7.02-7.06 (m, 1H), 7.34-7.38 (m, 1H), 8.14-8.19 (m, 1H), 8.22 (br s, 3H). |
| 51 | Intermediate 2 | LC-MS: 348.3, 350.3 [M + H]$^+$; RT 1.26 min. $^1$H NMR (500 MHz, DMSO-d$_6$) δ ppm 1.21 (d, J = 6.41 Hz, 3H), 2.89-3.01 (m, 1H), 3.04-3.14 (m, 1H), 3.36-3.47 (m, 1H), 3.59 (s, 3H), 4.59-4.71 (m, 2H), 7.19-7.26 (m, 1H), 7.28-7.37 (m, 4H), 8.08 (br s, 1H), 8.17 (br s, 3H). |
| 53 | Intermediate 2 | LC-MS: 366.3, 368.3 [M + H]$^+$; RT 1.28 min. $^1$H NMR (500 MHz, methanol-d$_4$) δ ppm 1.36 (d, J = 6.71 Hz, 3H), 3.01-3.14 (m, 2H), 3.65 (s, 3H), 3.56-3.63 (m, 1H), 4.80 (s, 2H), 7.07-7.14 (m, 2H), 7.23-7.31 (m, 1H), 7.38-7.45 (m, 1H); 3 NHs not observed. |

-continued

| Cpd | Starting Material | Spectral Data |
|-----|-------------------|---------------|
| 55 | Intermediate 2 | LC-MS: 349.3, 351.3 [M + H]$^+$; RT 0.88 min. $^1$H NMR (500 MHz, methanol-d$_4$) δ ppm 1.37 (d, J = 6.71 Hz, 3H), 3.03-3.12 (m, 1H), 3.13-3.21 (m, 1H), 3.58-3.65 (m, 1H), 3.68 (s, 3H), 5.06 (s, 2H), 7.96-8.04 (m, 1H), 8.07-8.13 (m, 1H), 8.54-8.63 (m, 1H), 8.74-8.83 (m, 1H); 3 NHs not observed. |
| 57 | Intermediate 2 | LC-MS: 349.3, 351.3 [M + H]$^+$; RT 0.84 min. $^1$H NMR (500 MHz, DMSO-d$_6$) δ ppm 1.21 (d, J = 6.41 Hz, 3H), 2.93-3.02 (m, 1H), 3.13-3.21 (m, 1H), 3.37-3.47 (m, 1H), 3.61 (s, 3H), 4.78-4.85 (m, 2H), 7.99-8.06 (m, 1H), 8.25-8.31 (m, 1H), 8.37 (br s, 3H), 8.51-8.57 (m, 1H), 8.79-8.85 (m, 1H), 8.88-8.92 (m, 1H). |
| 60 | Intermediate 2 | LC-MS: 338.1 [M + H]$^+$; RT 1.16 min. $^1$H NMR (500 MHz, DMSO-d$_6$) δ ppm 1.20 (d, J = 6.41 Hz, 3H), 2.95 (dd, J = 15.11, 9.00 Hz, 1H), 3.11 (dd, J = 14.95, 5.49 Hz, 1H), 3.36-3.46 (m, 1H), 3.59 (s, 3H), 4.62 (d, J = 6.10 Hz, 2H), 6.26 (d, J = 3.05 Hz, 1H), 6.39 (dd, J = 3.05, 1.83 Hz, 1H), 7.52-7.59 (m, 1H), 7.99 (br s, 1H), 8.11-8.33 (m, 3H) |

Example 7 (Compound 34)

6-[(2S)-2-Aminopropyl]-5-fluoro-N-[(furan-2-yl)methyl]-2-methyl-7H-pyrrolo[2,3-d]pyrimidin-4-amine dihydrochloride Step 1: tert-Butyl (S)-(6-(2-((tert-butoxycarbonyl)amino)propyl)-2-chloro-5-fluoro-7-(mesitylsulfonyl)-7H-pyrrolo[2,3-d]pyrimidin-4-yl)furan-2-ylmethyl)carbamate The title compound was prepared from Intermediate 9 according to the procedure described for Example 1 step 1.

Step 2: tert-Butyl (S)-(6-(2-((tert-butoxycarbonyl)amino)propyl)-5-fluoro-7-(mesitylsulfonyl)-2-methyl-7H-pyrrolo[2,3-d]pyrimidin-4-yl)furan-2-ylmethyl)carbamate To an oven-dried 20 mL scintillation vial was added tert-butyl (S)-(6-(2-((tert-butoxycarbonyl)amino)propyl)-2-chloro-5-fluoro-7-(mesitylsulfonyl)-7H-pyrrolo[2,3-d]pyrimidin-4-yl)(furan-2-ylmethyl)carbamate (119.0 mg, 0.17 mmol), cesium carbonate (150 mg, 0.46 mmol, 2.73 eq.), 1,1'-bis(diphenylphosphino)ferrocene-palladium(ii)dichloride dichloromethane complex (20 mg, 0.024 mmol, 0.14 eq.) followed by trimethylboroxine (45 mg, 0.05 mL, 0.35 mmol, 2.1 eq.). The flask was evacuated and then back-filled by an Ar balloon (I atm). To the solid mixture was added 1,4-dioxane (1.2 mL) followed by water (0.15 mL) at room temperature. Nitrogen was bubbled through the reaction mixture for 10 min before the reaction was heated to 100° C. and stirred at 100° C. for 24 h. The reaction progress was monitored by LC-MS analysis of an aliquot of the mixture. The reaction was diluted with DCM (10 mL) then quenched by sodium bicarbonate (aq. sat., 5 mL). The bi-phasic mixture was placed into a phase separator (70 mL), then the aqueous layer was washed by DCM (4×15 mL). The combined organic layers were dried over sodium sulfate and then concentrated to give the crude product which was purified by flash column chromatography (12 g, 0-15% EtAOc in hexanes doped with 10% DCM) to afford tert-butyl (S)-(6-(2-((tert-butoxycarbonyl)amino)propyl)-5-fluoro-7-(mesitylsulfonyl)-2-methyl-7H-pyrrolo[2,3-d]pyrimidin-4-yl)(furan-2-ylmethyl)carbamate as a light yellow foam. LC-MS: 708.2 [M+Na]$^+$; RT=2.06 min. $^1$H NMR (500 MHz, acetone-do) S ppm 1.27 (t, J=6.7 Hz, 3H), 1.31 (s, 9H), 1.41 (s, 9H), 2.28 (s, 3H), 2.42 (s, 3H), 2.62 (s, 6H), 3.24-3.45 (m, 2H), 4.13-4.25 (m, 1H), 4.99-5.19 (m, 2H), 5.92 (br d, J=7.02 Hz, 1H), 6.23 (br s, 1H), 6.25-6.45 (m, 1H), 7.06 (s, 2H), 7.37 (s, 1H).

Steps 3-4: 6-[(2S)-2-Aminopropyl]-5-fluoro-N-[(furan-2-yl)methyl]-2-methyl-7H-pyrrolo[2,3-d]pyrimidin-4-amine dihydrochloride The title compound was prepared from tert-butyl (S)-(6-(2-((tert-butoxycarbonyl)amino)propyl)-5-fluoro-7-(mesitylsulfonyl)-2-methyl-7H-pyrrolo[2,3-d]pyrimidin-4-yl)(furan-2-ylmethyl)carbamate according to the procedures described for Example 4 step 3 and Example 1 step 4. LC-MS: 304.2 [M+H]$^+$; RT=0.74 min. $^1$H NMR (500 MHz, methanol-d$_4$) δ ppm 1.35 (d, J=6.71 Hz, 3H), 2.66 (s, 3H), 3.00 (br dd, J=15.11, 7.78 Hz, 1H), 3.13 (dd, J=15.26, 6.1 Hz, 1H), 3.54-3.69 (m, 1H), 4.89 (s, 2H), 6.40 (s, 2H), 7.48 (s, 1H).

Example 8 (Compound 3)

2-Chloro-N-(furan-2-ylmethyl)-6-(2-(methylamino)ethyl)-7H-pyrrolo[2,3-d]pyrimidin-4-amine hydrochloride Step 1: 6-Allyl-2,4-dichlor-7-((2-(trimethylsilyl)ethoxy)methyl)-7H-pyrrolo[2,3-d]pyrimidine To a stirred solution of 2,4-dichloro-7-((2-(trimethylsilyl)ethoxy)methyl)-7H-pyrrolo[2,3-d]pyrimidine (Intermediate 1, 2.2 g, 6.3 mmol) in THF (15.0 mL) was added n-BuLi (2.5 M in hexanes, 4.0 mL, 10 mmol, 1.6 eq.) at −78° C. via syringe pump over 10 min. The reaction was stirred at −78° C. for 30 min before Copper(I) cyanide di(lithium chloride) complex solution (10 mL, 10 mmol, 1.6 eq.) was added to the reaction mixture at −78° C. The reaction was stirred at −78° C. for 30 min before allyl bromide (1.4 g, 1.0 mL, 11.44 mmol, 1.8 eq.) was added to the reaction mixture at −78° C. The reaction mixture was warmed to room temperature slowly (kept in the −78° C. cooling bath) and stirred overnight. After 12 h, the reaction was quenched by NH$_4$Cl (aq. sat., 30 mL) then extracted with diethyl ether (3×50 mL). The combined organic phases were dried over sodium sulfate and then concentrated to give the crude product which was purified by flash column chromatography (40 g, 0-10% EtOAc/hexanes) to afford 2-[(6-allyl-2,4-dichloropyrrolo[2,3-d]pyrimidin-7-yl)methoxy]ethyl-trimethyl-silane (1.74 g, 4.8 mmol, 76%) as a light yellow oil which solidified slowly upon standing at room temperature.

Step 2: 6-Allyl-2-chloro-N-(furan-2-ylmethyl)-7-((2-trimethylsilyl)ethoxy)methyl)-7H-pyrrolo[2,3-d]pyrimidin-4-amine The title compound was prepared from 6-allyl-2,4-dichloro-7-((2-(trimethylsilyl)ethoxy)methyl)-7H-pyrrolo[2,3-d]pyrimidine according to the procedure described for Example 1 step 2.

Step 3: 342-Chloro-4-((furan-2-ylmethyl)amino)-7-((2-(trimethylsilyl)ethoxy)methyl)-7H-pyrrolo[2,3-d]pyrimidin-6-yl)propane-1,2-diol To a stirred suspension of 6-allyl-2-chloro-N-(2-furylmethyl)-7-(2-trimethylsilylethoxymethyl)pyrrolo[2,3-d]pyrimidin-4-amine (945 mg, 2.26 mmol) in acetone (10 mL) and water (3 mL) was added 4-methylmorpholine n-oxide (396 mg, 3.28 mmol, 1.5 eq.) followed by potassium osmate (VI) dihydrate (50 mg, 0.15 mmol, 0.07 eq.) at room temperature. Then the reaction mixture was stirred at room temperature for 4-5 h. The reaction progress was monitored by TLC and LC-MS analysis of an aliquot of the mixture. After completion, the reaction was quenched with sodium thiosulfate (aq. sat., ~20 mL) then the mixture was extracted by EtOAc (2×40 mL). The combined organic layers were washed with brine (40 mL) then dried over sodium sulfate. The volatiles were removed under reduced pressure to give crude product which was purified by flash column chromatography (0-60% EtOAc in DCM) to afford 3-[2-chloro-4-(2-furylmethylamino)-7-(2-trimethylsilylethoxymethyl)pyrrolo[2,3-d]pyrimidin-6-yl]propane-1,2-diol (722.3 mg, 1.59 mmol, 71%) as a light yellow foam. LC-MS: 453.4, 455.4 [M+H]$^+$, 451.3 [M−H]$^-$; RT=1.48 min. $^1$H NMR (500 MHz, acetone-d$_6$) δ ppm −0.05 (s, 9H), 0.85-0.97 (m, 2H), 2.89 (dd, J=15.13, 7.70 Hz, 1H), 3.07 (dd, J=15.13, 4.73 Hz, 1H), 3.43-3.60 (m, 4H), 3.65-3.82 (m, 1H), 3.84-4.00 (m, 2H), 4.76 (d, J=5.67 Hz, 2H), 5.60 (d, J=11.20 Hz, 1H), 5.63 (d, J=11.20 Hz, 1H), 6.33 (dd, J=3.00, 0.80 Hz, 1H), 6.36 (dd, J=3.30, 1.89 Hz, 1H), 6.49 (s, 1H), 7.34 (br s, 1H), 7.46 (dd, J=1.89, 0.95 Hz, 1H).

Steps 4-6: tert-Butyl (2-(2-chloro-4-((furan-2-ylmethyl)amino)-7-((2-(trimethylsilyl)ethoxy)methyl)-7H-pyrrolo[2,3-d]pyrimidin-6-yl)ethyl)(methyl)carbamate To a stirred solution of 3-[2-chloro-4-(2-furylmethyl-amino)-7-(2-trimethylsilylethoxymethyl)pyrrolo[2,3-d]pyrimidin-6-yl]propane-1,2-diol (209.3 mg, 0.46 mmol) in THF (2.5 mL) and water (2.0 mL) was added sodium periodate (110.0 mg, 0.5 mmol, 1.1 eq.) at 0° C. The reaction mixture was stirred at 0° C. for 30 min before it was warmed to room temperature and then stirred at room temperature for an additional 1 h. TLC analysis of an aliquot of the mixture indicated the presence of starting material (~10%). The reaction was quenched with water (~10 mL) then the mixture was extracted with EtOAc (2×40 mL). The combined organic layers were washed with brine (30 mL) then dried over sodium sulfate. The volatiles were removed under reduced pressure to give 2-[2-chloro-4-(2-furylmethylamino)-7-(2-trimethylsilylethoxymethyl)pyrrolo[2,3-d]pyrimidin-6-yl]acetaldehyde (200.3 mg, 0.48 mmol) as a light brown foam which was carried over immediately to the next step without further purification. To a stirred solution of 2-[2-chloro-4-(2-furylmethylamino)-7-(2-trimethylsilylethoxymethyl)pyrrolo[2,3-d]pyrimidin-6-yl]acetaldehyde (200.3 mg, 0.48 mmol) in 1,2-dichloroethane (2.5 mL) was added methylamine (2 M in THF, 1.0 mL, 2.0 mmol, 4.2 eq.) followed by acetic acid (105 mg, 0.1 mL, 1.75 mmol, 3.67 eq.) at room temperature. The reaction mixture was stirred at room temperature for 10 min before sodium triacetoxyborohydride (305 mg, 1.44 mmol, 3.0 eq.) was added at room temperature. The reaction was stirred at room temperature overnight and the LC-MS analysis indicated the complete consumption of starting material. The reaction was quenched with sodium bicarbonate (aq. sat. ~5 mL) then extracted by DCM (5×10 mL) using a phase separator. The combined organic phases were dried over sodium sulfate and then concentrated to give 2-chloro-N-(2-furylmethyl)-6-[2-(methylamino)ethyl]-7-(2-trimethylsilylethoxymethyl) pyrrolo[2,3-d]pyrimidin-4-amine (204.0 mg, 0.47 mmol, 98%) which was carried over to the next step without further purification. LC-MS: 436.1, 438.1 [M+H]$^+$; RT=1.13 min. To a stirred solution of 2-chloro-N-(2-furylmethyl)-6-[2-(methylamino)ethyl]-7-(2-trimethylsilylethoxymethyl)pyrrolo[2,3-d]pyrimidin-4-amine (204.0 mg, 0.47 mmol) in THF (5.0 mL) was added di-tert-butyl dicarbonate (550 mg, 2.4 mmol, 5.2 eq.) at room temperature. The reaction was stirred overnight and the reaction progress was monitored by TLC analysis. The volatiles were removed under reduced pressure to give the crude product which was purified by flash column chromatography (0-40% EtOAc in hexanes doped with 10% DCM) to afford tert-butyl N-[2-[2-chloro-4-(2-furylmethylamino)-7-(2-trimethylsilylethoxymethyl) pyrrolo[2,3-d]pyrimidin-6-yl]ethyl]-N-methyl-carbamate (109.3 mg, 0.2 mmol) as an off-white foam in 44% yield over 3-steps. $^1$H NMR (500 MHz, acetone-d$_6$) δ ppm −0.04 (s, 9H), 0.85-1.00 (m, 2H), 1.30-1.44 (br d, -NBoc rotamer, 9H), 2.71-2.89 (br d, 3H), 2.93-3.10 (m, 2H), 3.47-3.63 (m, 4H), 4.75 (d, J=5.67 Hz, 2H), 5.69 (s, 2H), 6.27-6.39 (m, 2H), 6.42 (br s, 1H), 7.38 (br s, 1H), 7.46 (dd, J=1.73, 0.79 Hz, 1H).

Steps 7-8: 2-Chloro-N-(furan-2-ylmethyl)-6-(2-(methylamino)ethyl)-7H-pyrrolo[2,3-d]pyrimidin-4-amine hydrochloride The title compound was prepared from tert-butyl (2-(2-chloro-4-((furan-2-ylmethyl)amino)-7-((2-(trimethylsilyl)ethoxy)methyl)-7H-pyrolo[2,3-d]pyrimidin-6-yl)ethyl)(methyl)carbamate according to the procedures described for Example 1 step 3-4. LC-MS: 306.3, 308.3 [M+H]$^+$; RT=0.84 min. $^1$H NMR (500 MHz, DMSO-d$_6$) δ ppm 2.54 (t, t=5.60 Hz, 3H), 3.04 (t, J=7.70 Hz, 2H), 3.11-3.24 (m, 2H), 4.55-4.69 (m, 2H), 6.29 (dd, J=3.15, 0.95 Hz, 1H), 6.40 (dd, J=3.20, 1.89 Hz, 1H), 6.41 (d, J=1.90 Hz, 1H), 7.58 (dd, J=1.89, 0.95 Hz, 1H), 8.28 (br s, 1H), 9.06 (br s, 2H), 11.78 (br s, 1H).

The compounds below were prepared according to the procedure for Example 8 starting from the indicated starting material.

| Cpd | Starting Material | Spectral Data |
|---|---|---|
| 4 | Intermediate 1 | LC-MS: 320.3, 322.4 [M + H]$^+$, 318.4, 320.3 [M − H]$^-$; RT 0.91 min. $^1$H NMR (500 MHz, DMSO-d$_6$) δ ppm 1.18 (d, J = 6.71 Hz, 3H), 2.55 (s, 3H), 2.77-2.89 (m, 1H), 3.07-3.22 (m, 1H), 3.39-3.51 (m, 1H), 4.57-4.66 (m, 2H), 6.26-6.34 (m, 1H), 6.38-6.48 (m, 2H), 7.53-7.63 (m, 1H), 8.28 (br s, 1H), 8.93 (br s, 2H), 11.77 (br s, 1H). |
| 7 | Intermediate 1 | LC-MS: 320.1, 322.0 [M + H]$^+$; RT 1.03 min. $^1$H NMR (400 MHz, DMSO-d$_6$) δ ppm 2.21 (s, 6H), 2.54-2.63 (m, 2H), 2.73-2.82 (m, 2H), 4.58-4.67 (m, 2H), 6.27-6.35 (m, 2H), 6.37-6.44 (m, 1H), 7.55-7.63 (m, 1H), 8.09-8.18 (m, 1H), 11.57 (br s, 1H). |

Example 9 (Compound 1)

6-(3-Aminopropyl)-2-chloro-N-(furan-2-ylmethyl)-7H-pyrrolo[2,3-d]pyrimidin-4-amine hydrochloride

Step 1: 6-Bromo-2,4-dichloro-7-((2-(trimethylsilyl)ethoxy)methyl)-7H-pyrrolo[2,3-d]pyrimidine To a stirred solution of Intermediate 1 (924 mg, 2.9 mmol) in THF (8.0 mL) was added n-BuLi (2.5 M in hexanes, 1.5 mL, 3.8 mmol, 1.3 eq.) at −78° C. via syringe pump over 15 min. The reaction was stirred at −78° C. for 1 h before 1,2-dibromotetrafluoroethane (1.2 g, 0.55 mL, 4.6 mmol, 1.6 eq.) was added to the reaction mixture at −78° C. The reaction mixture was stirred at −78° C. for 1 h then allowed to warm to room temperature slowly overnight. The reaction mixture was quenched with ammonium chloride (aq. sat., ~10 mL) then extracted with diethyl ether (3×40 mL). The combined organic phases were washed with brine (50 mL) then dried over sodium sulfate. The drying agent was removed and then filtrate was concentrated to afford the crude product which was purified by flash column chromatography (0-10% EtAOc in hexanes) to afford 2-[(6-bromo-2,4-dichloro-pyrrolo[2,3-d]pyrimidin-7-yl)methoxy]ethyl-trimethyl-silane (882.0 mg, 2.2 mmol, 76%) as a light yellow oil.

Step 2: 6-Bromo-2-chloro-N-(furan-2-ylmethyl)-7-((2-trimethylsilyl)ethoxy)methyl-7H-pyrrolo[2,3-d]pyrimidin-4-amine The title compound was prepared from 6-bromo-2,4-dichloro-7-((2-(trimethylsilyl)ethoxy)methyl)-7H-pyrrolo[2,3-d]pyrimidine according to the procedure described for Example 1 step 2. LC-MS: 457.1, 459.1, 461.1 [M+H]$^+$; RT=1.79 min. $^1$H NMR (500 MHz, acetone-d$_6$) δ ppm −0.04 (s, 9H), 0.85-0.95 (m, 2H), 3.54-3.65 (m, 2H), 4.76 (d, J=5.67 Hz, 2H), 5.56 (s, 2H), 6.28-6.45 (m, 2H), 6.82 (s, 1H), 7.47 (dd, J=1.85, 0.94 Hz, 1H), 7.56 (br s, 1H).

Step 3: tert-Butyl (3-(2-chloro-4-((furan-2-ylmethyl)amino)-7-((2-(trimethylsilyl)ethoxy)methyl)-7H-pyrrolo[2,3-d]pyrimidin-6-yl)prop-2-yn-1-yl)carbamate To a 20 mL vial was added 6-bromo-2-chloro-N-(2-furylmethyl)-7-(2-trimethylsilylethoxymethyl)pyrrolo[2,3-d]pyrimidin-4-amine (248.6 mg, 0.54 mmol), CuI (12.0 mg, 0.062 mmol, 0.115 eq.), bis(triphenylphosphine)palladium (ii) dichloride (25 mg, 0.035 mmol, 0.065 eq.) and N-boc-propargylamine (150.0 mg, 0.94 mmol, 1.73 eq.). The vial was evacuated then back filled with Argon. To the solid mixture was added ACN (2.0 mL) followed by triethylamine (109 mg, 0.15 mL, 1.07 mmol, 1.96 eq.) at room temperature. Then the reaction was heated to 65° C. and then stirred for 4 h at 65° C.

The reaction progress was monitored by LC-MS and TLC analysis of an aliquot of the mixture. The reaction was quenched with water (~5 mL) then extracted with EtOAc (3×25 mL). The combined organic phases were washed with brine (40 mL) then dried over sodium sulfate. The drying agent was filtered and then the filtrate was concentrated to give the crude product which was purified by flash column chromatography (0-30% EtAOc in hexanes) to afford tert-butyl N-[3-[2-chloro-4-(2-furylmethylamino)-7-(2-trimethylsilylethoxymethyl)pyrrolo[2,3-d]pyrimidin-6-yl]prop-2-ynyl]carbamate (207 mg, 0.39 mmol, 72%) as a light yellow foam. LC-MS: 532.2, 534.4 [M+H]$^+$, 530.4, 532.4 [M−H]$^-$; RT=1.78 min.

Step 4: tert-Butyl (3-(2-chloro-4-((furan-2-ylmethyl)amino)-7-((2-(trimethylsilyl)ethoxy)methyl)-7H-pyrrolo[2,3-d]pyrimidin-6-ylpropyl)carbamate To a 50 mL round bottomed flask containing tert-butyl N-[3-[2-chloro-4-(2-furylmethylamino)-7-(2-trimethylsilylethoxymethyl)pyrrolo[2,3-d]pyrimidin-6-yl]prop-2-ynyl]carbamate (207.0 mg, 0.39 mmol) was added 10% palladium on carbon (Degussa type, ~30 mg) followed by EtOAc (6.0 mL). The reaction mixture was evacuated under vacuum then back-filled with a 1 atm hydrogen balloon in three cycles. The reaction was stirred at room temperature for 2 h. The reaction mixture was filtered through a 5 µm PTFE filter and then washed thoroughly with EtOAc (~30 mL). The filtrate was concentrated to give the crude product which was purified by flash column chromatography (0-30% EtAOc in hexanes) to afford tert-butyl N-[3-[2-chloro-4-(2-furylmethylamino)-7-(2-trimethylsilylethoxymethyl)pyrrolo[2,3-d]pyrimidin-6-yl]propyl]carbamate (152 mg, 0.28 mmol, 73%) as a light yellow foam. $^1$H NMR (500 MHz, acetone-d$_6$) δ ppm −0.05 (s, 9H), 0.82-0.97 (m, 2H), 1.40 (s, 9H), 1.83-2.00 (m, 2H), 2.83 (t, J=7.75 Hz, 2H), 3.18 (q, J=6.90 Hz, 2H), 3.47-3.60 (m, 2H), 4.76 (d, J=5.67 Hz, 2H), 5.54 (s, 2H), 6.02 (br s, 1H), 6.26-6.39 (m, 2H), 6.43 (s, 1H), 7.31 (br s, 1H), 7.46 (dd, J=1.73, 0.79 Hz, 1H).

Steps 5-6: 6-(3-Aminopropyl)-2-chloro-N-(furan-2-ylmethyl)-7H-pyrrolo[2,3-d]pyrimidin-4-amine hydrochloride The title compound was prepared from tert-butyl (3-(2-chloro-4-((furan-2-ylmethyl)amino)-7-((2-(trimethylsilyl)ethoxy)methyl)-7H-pyrrolo[2,3-d]pyrimidin-6-yl)propyl)carbamate according to the procedures described for Example 1 steps 3-4. LC-MS: 306.3, 308.3 [M+H]$^+$; RT=0.87 min. $^1$H NMR (500 MHz, DMSO-d$_6$) δ ppm 1.83-1.97 (m, 2H), 2.70 (t, J=7.57 Hz, 2H), 2.74-2.83 (m, 2H), 4.58-4.66 (m, 2H), 6.29 (dd, J=3.15, 0.63 Hz, 1H), 6.32 (d, J=1.89 Hz, 1H), 6.40 (dd, J=3.31, 1.73 Hz, 1H), 7.58 (dd, J=1.89, 0.95 Hz, 1H), 8.01 (br s, 3H), 8.21 (br s, 1H), 11.69 (s, 1H).

The compound below was prepared according to the procedures for Example 9 starting from the indicated starting material.

| Cpd | Starting Material | Spectral Data |
|---|---|---|
| 2 | Intermediate 3 | LC-MS: 324.3, 326.3 [M + H]$^+$, 322.1, 324.2 [M − H]$^-$; RT 0.88 min. $^1$H NMR (500 MHz, DMSO-d$_6$) δ ppm 1.85-1.95 (m, 2H), 2.67-2.74 (m, 2H), 2.74-2.84 (m, 2H), 4.61 (d, J = 5.67 Hz, 2H), 6.26 (dd, J = 3.15, 0.63 Hz, 1H), 6.38 (dd, J = 3.15, 1.89 Hz, 1H), 7.51-7.60 (m, 1H), 7.86 (br s, 1H), 7.99 (br s, 3H), 11.72 (s, 1H). |

Example 10 (Compound 46)

6-[(2S)-2-Aminopropyl]-2-chloro-5-fluoro-N-[(furan-2-yl)methyl]-7-(4-methoxyphenyl)-7H-pyrrolo[2,3-d]pyrimidin-4-amine hydrochloride Step 1: tert-Butyl (S)-(1-(2-chloro-5-fluoro-4-((furan-2-ylmethyl)amino)-7-(4-methoxyphenyl)-7H-pyrrolo[2,3-d]pyrimidin-6-yl)propan-2-yl)carbamate The title compound was prepared from Intermediate 12 according to the procedure described in Example 1 step 2. LC-MS: 530.2 [M+H]$^+$; RT=1.56 min. $^1$H NMR (500 MHz, CDCl$_3$) δ ppm 0.93 (d, J=6.71 Hz, 3H), 1.24 (s, 9H), 2.53-2.68 (m, 2H), 3.79 (s, 3H), 4.16 (br s, 1H), 4.68-4.81 (m, 2H), 6.29 (d, J=1.53 Hz, 2H), 6.87-7.00 (m, 2H), 7.18-7.25 (m, 2H), 7.33 (t, J=1.37 Hz, 1H).

Step 2: 6-[(2S)-2-Aminopropyl]-2-chloro-5-fluoro-N-[(furan-2-yl)methyl]-7-(4-methoxyphenyl)-7H-pyrrolo[2,3-d]pyrimidin-4-amine hydrochloride The title compound was prepared from tert-butyl (S)-(1-(2-chloro-5-fluoro-4-((furan-2-ylmethyl)amino)-7-(4-methoxyphenyl)-7H-pyrrolo[2,3-d]pyrimidin-6-yl)propan-2-yl)carbamate according to the procedure described in Example 1 step 4. LC-MS: 430.3, 432.2 [M+H]$^+$; RT=1.17 min. $^1$H NMR (500 MHz, DMSO-d$_6$) δ ppm 1.06 (d, J=6.41 Hz, 3H), 2.73-2.89 (m, 1H), 2.93-3.06 (m, 2H), 3.85 (s, 3H), 4.66 (d, J=6.10 Hz, 2H), 6.30 (d, J=3.36 Hz, 1H), 6.41 (dd, J=3.05, 1.83 Hz, 1H), 7.04-7.21 (m, 2H), 7.32-7.40 (m, 2H), 7.50-7.68 (m, 1H), 8.06 (br s, 3H), 8.15 (br s, 1H).

The compound below was prepared according to the procedure for Example 7 starting from the indicated starting material.

| Cpd | Starting Material | Spectral Data |
|---|---|---|
| 47 | Intermediate 12 | LC-MS: 446.3, 448.2 [M + H]$^+$; RT = 1.19 min. $^1$H NMR (500 MHz, DMSO-d$_6$) δ ppm 1.05 (d, J = 7.60 Hz, 3H), 2.72-2.87 (m, 1H), 2.92-3.05 (m, 2H), 3.85 (s, 3H), 4.80 (d, J = 5.80 Hz, 2H), 6.97 (dd, J = 5.04, 3.51 Hz, 1H), 7.04-7.17 (m, 3H), 7.33-7.41 (m, 3H), 8.08 (br s, 3H), 8.31 (br t, J = 5.95 Hz, 1H). |

BIOLOGICAL EXAMPLES

The following in vitro biological examples demonstrate the usefulness of the compounds of the present description for treating familial dysautonomia.

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed.

Example 1

IKBKAP-HTRF Assay

The assay is used for the quantitative determination of Elongator complex protein 1 (ELPI, also referred to as IKBKAP) concentration in cell lysates using the HTRF® (Homogeneous Time-Resolved Fluorescence) technology. IKBKAP is detected in a sandwich HTRF assay by use of an anti-IKAP antibody labeled with a donor and an anti-IKAP antibody labeled with an acceptor.

| Materials | Source |
|---|---|
| FD Patient-derived fibroblasts | GM04589 (Coriell Institute) |
| DMEM | Invitrogen Catalogue No. 11960-044 |
| LB4 (4X) Lysis Buffer | Cisbio |
| Protease Inhibitor Cocktail | Roche Catalogue No. 11836145001 |
| Anti IKAP-K(9 + 8) 50X | Cisbio |
| Anti IKAP-d2 50X | Cisbio |
| IKAP Detection Buffer | Cisbio |
| EnVision Plate Reader | Perkin Elmer Model No. 2103 |

Protocol

Cells were thawed and incubated in DMEM-10% FBS for 72 hours. Cells were trypsinized, counted, and re-suspended to a concentration of 50,000 cells/ml in DMEM-10% FBS. A 199 μL aliquot of the cell suspensions were plated at 10,000 cells per well in a 96 well microtiter plate and incubated for 3 to 5 hours. To provide a control signal, three wells did not receive cells and served as Blank control wells. Test compounds were serially diluted 3.16-fold in 100% DMSO to generate a 7-point concentration curve. A 1 μL aliquot of 200× compound solution was transferred to cell-containing wells, and cells were incubated for 48 hours in a cell culture incubator (37° C., 5% CO$_2$, 100% relative humidity). Triplicate samples were set up for each compound concentration. After 48 hours, the supernatant was removed from the cells and 50 µL of the 1×LB4 lysis buffer, containing protease inhibitors, was added to the cells and incubated with shaking at room temperature for 1 hour. A 36 µL aliquot of this lysate was subsequently transferred to the 384-well plate containing 4 µL of the antibody solution (1:50 dilution of anti IKAP d2 and anti-IKAP K(9+8) in detection buffer). The 384-well plate was then centrifuged for 1 minute to bring the solutions to the bottom of the plate and incubated overnight at 4° C. Fluorescence for each well of the plate at 665 nm and 620 nm was measured was on the EnVision plate reader (Perkin Elmer). The ΔF for each sample is calculated by:

$$\Delta F = \frac{(\text{Signal} - \text{Blank}) \times 100}{\text{Blank}}$$

wherein Signal is the normalized fluorescence for each sample well and Blank is the average normalized average fluorescence for the Blank control wells.

The maximum fold increase (MFI) in IKBKAP protein abundance for compounds of Formula (I) or a form thereof relative to the vehicle control are provided in Table 1. MFI was calculated by dividing the ΔF value for each sample well by the sample ΔF for the vehicle control wells.

An MFI≤1.9 is indicated by one star (*), between >1.9 and ≤2.9 is indicated by two stars (), between >2.9 and ≤3.9 is indicated by three stars (*), between >3.9 and ≤4.9 is indicated by four stars (**), and >4.9 is indicated by five stars (***).

The $EC_{2x}$ for IKBKAP protein expression obtained from the 7-point concentration curve generated for each test compound according to the protocol in Biological Example 1 are also provided in Table 1. The term "$EC_{2x}$ for IKBKAP protein expression" is defined as the concentration of test compound that is effective in producing two times the amount of IKBKAP protein in a FD patient cell compared to the amount produced from the DMSO vehicle control.

An $EC_{2x}$>1 µM is indicated by one star (*), between >0.5 µM and ≤1 µM is indicated by two stars (), between >0.02 µM and ≤0.5 µM is indicated by three stars (*), between >0.005 µM and ≤0.02 µM is indicated by four stars (**), and ≤0.005 µM is indicated by five stars (***)

TABLE 1

An $EC_{2x}$ >1 µM is indicated by one star (*), between >0.5 µM and ≤1 µM is indicated by two stars (), between >0.02 µM and ≤0.5 µM is indicated by three stars (*), between >0.005 µM and ≤0.02 µM is indicated by four stars (**), and ≤0.005 µM is indicated by five stars (***).

| Cpd | MFI | $EC_{2x}$ |
|---|---|---|
| 1 | **** | *** |
| 2 | *** | *** |
| 3 | ***** | *** |
| 4 | **** | *** |
| 5 | ***** | *** |
| 6 | ***** | *** |
| 7 | * | * |
| 8 | *** | *** |
| 9 | **** | *** |
| 10 | ***** | **** |
| 11 | **** | *** |
| 12 | ***** | *** |
| 13 | ***** | ***** |

TABLE 1-continued

An $EC_{2x}$ >1 µM is indicated by one star (*), between >0.5 µM and ≤1 µM is indicated by two stars (), between >0.02 µM and ≤0.5 µM is indicated by three stars (*), between >0.005 µM and ≤0.02 µM is indicated by four stars (**), and ≤0.005 µM is indicated by five stars (***).

| Cpd | MFI | $EC_{2x}$ |
|---|---|---|
| 14 | ***** | **** |
| 15 | **** | *** |
| 16 | **** | **** |
| 17 | **** | *** |
| 18 | **** | *** |
| 19 | **** | **** |
| 20 | ***** | *** |
| 21 | **** | **** |
| 22 | ***** | **** |
| 23 | ***** | **** |
| 24 | ***** | **** |
| 25 | ***** | **** |
| 26 | **** | **** |
| 27 | ***** | *** |
| 28 | * | * |
| 29 | **** | *** |
| 30 | ***** | *** |
| 31 | ***** | **** |
| 32 | ***** | **** |
| 33 | ***** | ***** |
| 34 | ***** | *** |
| 35 | ***** | **** |
| 36 | ***** | **** |
| 37 | ***** | *** |
| 38 | ***** | *** |
| 39 | ***** | **** |
| 40 | ***** | **** |
| 41 | ***** | *** |
| 42 | ** | *** |
| 43 | ***** | *** |
| 44 | ***** | **** |
| 45 | ***** | *** |
| 46 | * | * |
| 47 | * | * |
| 48 | * | * |
| 49 | ***** | **** |
| 50 | *** | *** |
| 51 | *** | *** |
| 52 | **** | *** |
| 53 | **** | *** |
| 54 | ** | *** |
| 55 | * | * |
| 56 | * | * |
| 57 | * | * |
| 58 | **** | *** |
| 59 | ***** | *** |
| 60 | * | * |
| 61 | * | * |
| 62 | ***** | **** |

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or particular aspects described herein. It is intended that the appended claims be interpreted to include all such equivalents.

What is claimed is:

1. A compound of Formula (I):

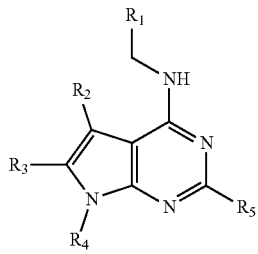

or a pharmaceutically acceptable salt, stereoisomer, or tautomer thereof,
wherein:
- $R_1$ is phenyl or heteroaryl;
  - wherein the heteroaryl is a monocyclic or bicyclic 5-8 membered aromatic carbon atom ring structure radical containing 1, 2, or 3 heteroatoms independently selected from the group consisting of N, O, and S; and
  - wherein the phenyl or heteroaryl is optionally substituted with one, two, three, or four Independently selected $R_{1a}$ substituents;
- each $R_{1a}$ is independently halo, cyano, $C_{1-6}$ alkyl, deutero-$C_{1-6}$ alkyl, halo-$C_{1-6}$ alkyl, hydroxy, or $C_{1-6}$ alkoxy;
- $R_2$ is hydrogen, halo, or $C_{1-6}$ alkyl;
- $R_3$ is $C_{2-6}$ alkyl;
  - wherein the $C_{2-6}$ alkyl optionally contains a chiral carbon having an (R) configuration or (S) configuration; and
  - wherein the $C_{2-6}$ alkyl is optionally substituted with one, two, three, or four independently selected $R_{3a}$ substituents;
- each $R_{3a}$ is independently halo, cyano, $C_{1-6}$ alkyl, deutero-$C_{1-6}$ alkyl, halo-$C_{1-6}$ alkyl, amino, $C_{1-6}$ alkyl-amino, deutero-$C_{1-6}$ alkyl-amino, ($C_{1-6}$ alkyl)$_2$-amino, hydroxy, or $C_{1-6}$ alkoxy;
- $R_4$ is hydrogen, $C_{1-6}$ alkyl, or phenyl, wherein the $C_{1-6}$ alkyl or phenyl is optionally substituted with one, two, three, or four independently selected $R_{4a}$ substituents;
- each $R_{4a}$ is independently halo, cyano, $C_{1-6}$ alkyl, halo-$C_{1-6}$ alkyl, hydroxy, or $C_{1-6}$ alkoxy; and
- $R_5$ is hydrogen, halo, or $C_{1-6}$ alkyl.

2. The compound of claim 1, or a pharmaceutically acceptable salt, stereoisomer, or tautomer thereof, wherein $R_1$ is phenyl, furanyl, thiophenyl, 1H-pyrazolyl, 1H-imidazolyl, isoxazolyl, 1,3-oxazolyl, 1,3-thiazolyl, 1,2,3-triazolyl, 1,2,4-oxadiazolyl, 1,3,4-oxadiazolyl, 1,2,3-thiadiazolyl, pyridinyl, pyridazinyl, pyrimidinyl, or pyrazinyl.

3. The compound of claim 1, or a pharmaceutically acceptable salt, stereoisomer, or tautomer thereof, wherein $R_1$ is furanyl, thiophenyl, 1,3-oxazolyl, 1,3-thiazolyl, or pyridinyl.

4. The compound of claim 1, or a pharmaceutically acceptable salt, stereoisomer, or tautomer thereof, wherein $R_3$ is $C_{2-6}$ alkyl containing a chiral carbon having an (R) configuration.

5. The compound of claim 1, or a pharmaceutically acceptable salt, stereoisomer, or tautomer thereof, wherein $R_3$ is $C_{2-6}$ alkyl containing a chiral carbon having an (S) configuration.

6. A pharmaceutical composition comprising a pharmaceutically acceptable excipient in admixture with a therapeutically effective amount of the compound of claim 1, or a pharmaceutically acceptable salt, stereoisomer, or tautomer thereof.

7. A method for treating familial dysautonomia in a subject, wherein the method comprises administering to the subject in need thereof a therapeutically effective amount of the compound of claim 1, or a pharmaceutically acceptable salt, stereoisomer, or tautomer thereof.

8. A compound selected from the group consisting of:
- 6-(3-aminopropyl)-2-chloro-N-[(furan-2-yl)methyl]-7H-pyrrolo[2,3-d]pyrimidin-4-amine;
- 6-(3-aminopropyl)-2-chloro-5-fluoro-N-[(furan-2-yl)methyl]-7H-pyrrolo[2,3-d]pyrimidin-4-amine;
- 2-chloro-N-[(furan-2-yl)methyl]-6-[2-(methylamino)ethyl]-7H-pyrrolo[2,3-d]pyrimidin-4-amine;
- 2-chloro-N-[(furan-2-yl)methyl]-6-[2-(methylamino)propyl]-7H-pyrrolo[2,3-d]pyrimidin-4-amine;
- 2-chloro-6-[2-(methylamino)ethyl]-N-[(1,3-thiazol-2-yl)methyl]-7H-pyrrolo[2,3-d]pyrimidin-4-amine;
- 2-chloro-5-fluoro-N-[(furan-2-yl)methyl]-6-[2-(methylamino)ethyl]-7H-pyrrolo[2,3-d]pyrimidin-4-amine;
- 2-chloro-6-[2-(dimethylamino)ethyl]-N-[(furan-2-yl)methyl]-7H-pyrrolo[2,3-d]pyrimidin-4-amine;
- 6-(2-aminoethyl)-2-chloro-N-[(furan-2-yl)methyl]-7H-pyrrolo[2,3-d]pyrimidin-4-amine;
- 2-chloro-N-[(furan-2-yl)methyl]-6-{2-[($^2H_3$)methylamino]ethyl}-7H-pyrrolo[2,3-d]pyrimidin-4-amine;
- 6-[(2S)-2-aminopropyl]-2-chloro-5-fluoro-N-[(furan-2-yl)methyl]-7H-pyrrolo[2,3-d]pyrimidin-4-amine;
- 6-[(2R)-2-amino-3-methylbutyl]-2-chloro-N-[(furan-2-yl)methyl]-7H-pyrrolo[2,3-d]pyrimidin-4-amine;
- 6-[(2R)-2-amino-3-methylbutyl]-2-chloro-N-[(pyridin-4-yl)methyl]-7H-pyrrolo[2,3-d]pyrimidin-4-amine;
- 6-[(2S)-2-aminopropyl]-2,5-dichloro-N-[(furan-2-yl)methyl]-7H-pyrrolo[2,3-d]pyrimidin-4-amine;
- 6-[(2R)-2-amino-3-methylbutyl]-2-chloro-5-fluoro-N-[(furan-2-yl)methyl]-7H-pyrrolo[2,3-d]pyrimidin-4-amine;
- 6-[(2R)-2-amino-3-methylbutyl]-2-chloro-5-fluoro-N-[(pyridin-4-yl)methyl]-7H-pyrrolo[2,3-d]pyrimidin-4-amine;
- 6-[(2S)-2-aminopropyl]-2-chloro-N-[(furan-2-yl)methyl]-7H-pyrrolo[2,3-d]pyrimidin-4-amine;
- 2,5-dichloro-N-[(furan-2-yl)methyl]-6-[2-(methylamino)ethyl]-7H-pyrrolo[2,3-d]pyrimidin-4-amine;
- 5-bromo-2-chloro-N-[(furan-2-yl)methyl]-6-[2-(methylamino)ethyl]-7H-pyrrolo[2,3-d]pyrimidin-4-amine;
- 6-[(2S)-2-aminopropyl]-5-bromo-2-chloro-N-[(furan-2-yl)methyl]-7H-pyrrolo[2,3-d]pyrimidin-4-amine;
- 6-[(2S)-2-aminopropyl]-2-chloro-N-[(pyridin-4-yl)methyl]-7H-pyrrolo[2,3-d]pyrimidin-4-amine;
- 6-[(2S)-2-aminobutyl]-2,5-dichloro-N-[(furan-2-yl)methyl]-7H-pyrrolo[2,3-d]pyrimidin-4-amine;
- 6-[(2S)-2-aminopropyl]-2-chloro-N-[(1,3-thiazol-2-yl)methyl]-7H-pyrrolo[2,3-d]pyrimidin-4-amine;
- 6-[(2S)-2-aminopropyl]-2,5-dichloro-N-[(furan-2-yl)methyl]-7-methyl-7H-pyrrolo[2,3-d]pyrimidin-4-amine;
- 6-[(2S)-2-aminopropyl]-2-chloro-5-fluoro-N-[(furan-2-yl)methyl]-7-methyl-7H-pyrrolo[2,3-d]pyrimidin-4-amine;
- 6-[(2S)-2-aminopropyl]-2-chloro-N-[(thiophen-2-yl)methyl]-7H-pyrrolo[2,3-d]pyrimidin-4-amine;
- 6-[(2S)-2-aminobutyl]-2-chloro-N-[(furan-2-yl)methyl]-7H-pyrrolo[2,3-d]pyrimidin-4-amine;

6-[(2S)-2-aminopropyl]-2-chloro-N-[(1,3-oxazol-2-yl) methyl]-7H-pyrrolo[2,3-d]pyrimidin-4-amine;

6-[(2S)-2-aminopropyl]-5-butyl-2-chloro-N-[(furan-2-yl) methyl]-7H-pyrrolo[2,3-d]pyrimidin-4-amine;

6-[(2R)-2-amino-3,3-dimethylbutyl]-2-chloro-N-[(furan-2-yl)methyl]-7H-pyrrolo[2,3-d]pyrimidin-4-amine;

6-[(2S)-2-aminopropyl]-2-chloro-N-[(furan-3-yl) methyl]-7H-pyrrolo[2,3-d]pyrimidin-4-amine;

6-[(2S)-2-aminopropyl]-2-chloro-N-[(3-fluoropyridin-4-yl)methyl]-7H-pyrrolo[2,3-d]pyrimidin-4-amine;

6-[(2R,3S)-2-amino-3-methylpentyl]-2-chloro-N-[(furan-2-yl)methyl]-7H-pyrrolo[2,3-d]pyrimidin-4-amine;

6-[(2S)-2-aminopropyl]-2-chloro-N-[(furan-2-yl) methyl]-5-methyl-7H-pyrrolo[2,3-d]pyrimidin-4-amine;

6-[(2S)-2-aminopropyl]-5-fluoro-N-[(furan-2-yl)methyl]-2-methyl-7H-pyrrolo[2,3-d]pyrimidin-4-amine;

6-[(2S)-2-aminopropyl]-2-chloro-N-[(furan-2-yl) methyl]-5,7-dimethyl-7H-pyrrolo[2,3-d]pyrimidin-4-amine;

6-[(2S)-2-aminopropyl]-2-chloro-5-fluoro-N-[(1,3-thiazol-2-yl)methyl]-7H-pyrrolo[2,3-d]pyrimidin-4-amine;

6-[(2R)-2-amino-3-methoxypropyl]-2-chloro-5-fluoro-N-[(furan-2-yl)methyl]-7-methyl-7H-pyrrolo[2,3-d]pyrimidin-4-amine;

6-[(2S)-2-aminopropyl]-2-chloro-5-fluoro-7-methyl-N-[(1,3-thiazol-2-yl)methyl]-7H-pyrrolo[2,3-d]pyrimidin-4-amine;

(2R)-2-amino-3-(2-chloro-5-fluoro-4-{[(furan-2-yl) methyl]amino}-7-methyl-7H-pyrrolo[2,3-d]pyrimidin-6-yl)propan-1-ol;

6-[(2S)-2-aminopropyl]-2-chloro-5-fluoro-N-[(thiophen-2-yl)methyl]-7H-pyrrolo[2,3-d]pyrimidin-4-amine;

6-[(2S)-2-aminopropyl]-2-chloro-5-fluoro-N-[(3-fluoropyridin-4-yl)methyl]-7-methyl-7H-pyrrolo[2,3-d]pyrimidin-4-amine;

6-[(2S)-2-aminopropyl]-2-chloro-7-ethyl-5-fluoro-N-[(furan-2-yl)methyl]-7H-pyrrolo[2,3-d]pyrimidin-4-amine;

6-[(2S)-2-aminopropyl]-2-chloro-5-fluoro-7-methyl-N-[(pyridin-4-yl)methyl]-7H-pyrrolo[2,3-d]pyrimidin-4-amine;

6-[(2S)-2-aminobutyl]-2-chloro-5-fluoro-N-[(furan-2-yl)methyl]-7H-pyrrolo[2,3-d]pyrimidin-4-amine;

6-[(2S)-2-aminobutyl]-2-chloro-5-fluoro-N-[(furan-2-yl)methyl]-7-methyl-7H-pyrrolo[2,3-d]pyrimidin-4-amine;

6-[(2S)-2-aminopropyl]-2-chloro-5-fluoro-N-[(furan-2-yl)methyl]-7-(4-methoxyphenyl)-7H-pyrrolo[2,3-d]pyrimidin-4-amine;

6-[(2S)-2-aminopropyl]-2-chloro-5-fluoro-7-(4-methoxyphenyl)-N-[(thiophen-2-yl)methyl]-7H-pyrrolo[2,3-d]pyrimidin-4-amine;

6-[(2S)-2-aminopropyl]-2-chloro-5-fluoro-7-methyl-N-[(1,3-thiazol-5-yl)methyl]-7H-pyrrolo[2,3-d]pyrimidin-4-amine;

6-[(2S)-2-aminopropyl]-2-chloro-5-fluoro-7-methyl-N-[(thiophen-2-yl)methyl]-7H-pyrrolo[2,3-d]pyrimidin-4-amine;

6-[(2S)-2-aminopropyl]-N-benzyl-2-chloro-5-fluoro-7H-pyrrolo[2,3-d]pyrimidin-4-amine;

6-[(2S)-2-aminopropyl]-N-benzyl-2-chloro-5-fluoro-7-methyl-7H-pyrrolo[2,3-d]pyrimidin-4-amine;

6-[(2S)-2-aminopropyl]-2-chloro-5-fluoro-N-[(2-fluorophenyl)methyl]-7H-pyrrolo[2,3-d]pyrimidin-4-amine;

6-[(2S)-2-aminopropyl]-2-chloro-5-fluoro-N-[(2-fluorophenyl)methyl]-7-methyl-7H-pyrrolo[2,3-d]pyrimidin-4-amine;

6-[(2S)-2-aminopropyl]-2-chloro-5-fluoro-N-[(pyridin-2-yl)methyl]-7H-pyrrolo[2,3-d]pyrimidin-4-amine;

6-[(2S)-2-aminopropyl]-2-chloro-5-fluoro-7-methyl-N-[(pyridin-2-yl)methyl]-7H-pyrrolo[2,3-d]pyrimidin-4-amine;

6-[(2S)-2-aminopropyl]-2-chloro-5-fluoro-N-[(pyridin-3-yl)methyl]-7H-pyrrolo[2,3-d]pyrimidin-4-amine;

6-[(2S)-2-aminopropyl]-2-chloro-5-fluoro-7-methyl-N-[(pyridin-3-yl)methyl]-7H-pyrrolo[2,3-d]pyrimidin-4-amine;

6-[(2S)-2-aminobutyl]-2-chloro-5-fluoro-N-[(thiophen-2-yl)methyl]-7H-pyrrolo[2,3-d]pyrimidin-4-amine;

6-[(2S)-2-aminobutyl]-2-chloro-5-fluoro-N-[(1,3-thiazol-2-yl)methyl]-7H-pyrrolo[2,3-d]pyrimidin-4-amine;

6-[(2R)-2-aminopropyl]-2-chloro-5-fluoro-N-[(furan-2-yl)methyl]-7-methyl-7H-pyrrolo[2,3-d]pyrimidin-4-amine;

6-[(2S)-2-aminopropyl]-2-chloro-N-[(1,3-thiazol-4-yl) methyl]-7H-pyrrolo[2,3-d]pyrimidin-4-amine; and 6-[(2S)-2-aminopropyl]-2-bromo-5-fluoro-N-[(furan-2-yl)methyl]-7H-pyrrolo[2,3-d]pyrimidin-4-amine, or a pharmaceutically acceptable salt or tautomer thereof.

9. A pharmaceutical composition comprising a pharmaceutically acceptable excipient in admixture with a therapeutically effective amount of the compound of claim 8, or a pharmaceutically acceptable salt or tautomer thereof.

10. A method for treating familial dysautonomia in a subject, wherein the method comprises administering to the subject in need thereof a therapeutically effective amount of the compound of claim 8, or a pharmaceutically acceptable salt or tautomer thereof.

11. A compound selected from the group consisting of:

6-(3-aminopropyl)-2-chloro-N-[(furan-2-yl)methyl]-7H-pyrrolo[2,3-d]pyrimidin-4-amine hydrochloride;

6-(3-aminopropyl)-2-chloro-5-fluoro-N-[(furan-2-yl) methyl]-7H-pyrrolo[2,3-d]pyrimidin-4-amine hydrochloride;

2-chloro-N-[(furan-2-yl)methyl]-6-[2-(methylamino) ethyl]-7H-pyrrolo[2,3-d]pyrimidin-4-amine hydrochloride;

2-chloro-N-[(furan-2-yl)methyl]-6-[2-(methylamino)propyl]-7H-pyrrolo[2,3-d]pyrimidin-4-amine hydrochloride;

2-chloro-6-[2-(methylamino)ethyl]-N-[(1,3-thiazol-2-yl) methyl]-7H-pyrrolo[2,3-d]pyrimidin-4-amine hydrochloride;

2-chloro-5-fluoro-N-[(furan-2-yl)methyl]-6-[2-(methylamino)ethyl]-7H-pyrrolo[2,3-d]pyrimidin-4-amine hydrochloride;

6-(2-aminoethyl)-2-chloro-N-[(furan-2-yl)methyl]-7H-pyrrolo[2,3-d]pyrimidin-4-amine hydrochloride;

2-chloro-N-[(furan-2-yl)methyl]-6-{2-[($^{2}H_3$)methylamino]ethyl}-7H-pyrrolo[2,3-d]pyrimidin-4-amine hydrochloride;

6-[(2S)-2-aminopropyl]-2-chloro-5-fluoro-N-[(furan-2-yl)methyl]-7H-pyrrolo[2,3-d]pyrimidin-4-amine hydrochloride;

6-[(2R)-2-amino-3-methylbutyl]-2-chloro-N-[(furan-2-yl)methyl]-7H-pyrrolo[2,3-d]pyrimidin-4-amine hydrochloride;

6-[(2R)-2-amino-3-methylbutyl]-2-chloro-N-[(pyridin-4-yl)methyl]-7H-pyrrolo[2,3-d]pyrimidin-4-amine dihydrochloride;

6-[(2S)-2-aminopropyl]-2,5-dichloro-N-[(furan-2-yl)methyl]-7H-pyrrolo[2,3-d]pyrimidin-4-amine hydrochloride;

6-[(2R)-2-amino-3-methylbutyl]-2-chloro-5-fluoro-N-[(furan-2-yl)methyl]-7H-pyrrolo[2,3-d]pyrimidin-4-amine hydrochloride;

6-[(2R)-2-amino-3-methylbutyl]-2-chloro-5-fluoro-N-[(pyridin-4-yl)methyl]-7H-pyrrolo[2,3-d]pyrimidin-4-amine dihydrochloride;

2,5-dichloro-N-[(furan-2-yl)methyl]-6-[2-(methylamino)ethyl]-7H-pyrrolo[2,3-d]pyrimidin-4-amine hydrochloride;

5-bromo-2-chloro-N-[(furan-2-yl)methyl]-6-[2-(methylamino)ethyl]-7H-pyrrolo[2,3-d]pyrimidin-4-amine hydrochloride;

6-[(2S)-2-aminopropyl]-5-bromo-2-chloro-N-[(furan-2-yl)methyl]-7H-pyrrolo[2,3-d]pyrimidin-4-amine hydrochloride;

6-[(2S)-2-aminobutyl]-2,5-dichloro-N-[(furan-2-yl)methyl]-7H-pyrrolo[2,3-d]pyrimidin-4-amine hydrochloride;

6-[(2S)-2-aminopropyl]-2-chloro-N-[(1,3-thiazol-2-yl)methyl]-7H-pyrrolo[2,3-d]pyrimidin-4-amine hydrochloride;

6-[(2S)-2-aminopropyl]-2,5-dichloro-N-[(furan-2-yl)methyl]-7-methyl-7H-pyrrolo[2,3-d]pyrimidin-4-amine hydrochloride;

6-[(2S)-2-aminopropyl]-2-chloro-5-fluoro-N-[(furan-2-yl)methyl]-7-methyl-7H-pyrrolo[2,3-d]pyrimidin-4-amine hydrochloride;

6-[(2S)-2-aminopropyl]-2-chloro-N-[(thiophen-2-yl)methyl]-7H-pyrrolo[2,3-d]pyrimidin-4-amine hydrochloride;

6-[(2S)-2-aminopropyl]-2-chloro-N-[(1,3-oxazol-2-yl)methyl]-7H-pyrrolo[2,3-d]pyrimidin-4-amine hydrochloride;

6-[(2S)-2-aminopropyl]-5-butyl-2-chloro-N-[(furan-2-yl)methyl]-7H-pyrrolo[2,3-d]pyrimidin-4-amine hydrochloride;

6-[(2R)-2-amino-3,3-dimethylbutyl]-2-chloro-N-[(furan-2-yl)methyl]-7H-pyrrolo[2,3-d]pyrimidin-4-amine hydrochloride;

6-[(2S)-2-aminopropyl]-2-chloro-N-[(furan-3-yl)methyl]-7H-pyrrolo[2,3-d]pyrimidin-4-amine hydrochloride;

6-[(2S)-2-aminopropyl]-2-chloro-N-[(3-fluoropyridin-4-yl)methyl]-7H-pyrrolo[2,3-d]pyrimidin-4-amine dihydrochloride;

6-[(2R,3S)-2-amino-3-methylpentyl]-2-chloro-N-[(furan-2-yl)methyl]-7H-pyrrolo[2,3-d]pyrimidin-4-amine hydrochloride;

6-[(2S)-2-aminopropyl]-2-chloro-N-[(furan-2-yl)methyl]-5-methyl-7H-pyrrolo[2,3-d]pyrimidin-4-amine hydrochloride;

6-[(2S)-2-aminopropyl]-5-fluoro-N-[(furan-2-yl)methyl]-2-methyl-7H-pyrrolo[2,3-d]pyrimidin-4-amine hydrochloride;

6-[(2S)-2-aminopropyl]-2-chloro-N-[(furan-2-yl)methyl]-5,7-dimethyl-7H-pyrrolo[2,3-d]pyrimidin-4-amine hydrochloride;

6-[(2S)-2-aminopropyl]-2-chloro-5-fluoro-N-[(1,3-thiazol-2-yl)methyl]-7H-pyrrolo[2,3-d]pyrimidin-4-amine hydrochloride;

6-[(2R)-2-amino-3-methoxypropyl]-2-chloro-5-fluoro-N-[(furan-2-yl)methyl]-7-methyl-7H-pyrrolo[2,3-d]pyrimidin-4-amine hydrochloride;

6-[(2S)-2-aminopropyl]-2-chloro-5-fluoro-7-methyl-N-[(1,3-thiazol-2-yl)methyl]-7H-pyrrolo[2,3-d]pyrimidin-4-amine hydrochloride;

(2R)-2-amino-3-(2-chloro-5-fluoro-4-{[(furan-2-yl)methyl]amino}-7-methyl-7H-pyrrolo[2,3-d]pyrimidin-6-yl)propan-1-ol hydrochloride;

6-[(2S)-2-aminopropyl]-2-chloro-5-fluoro-N-[(thiophen-2-yl)methyl]-7H-pyrrolo[2,3-d]pyrimidin-4-amine hydrochloride;

6-[(2S)-2-aminopropyl]-2-chloro-5-fluoro-N-[(3-fluoropyridin-4-yl)methyl]-7-methyl-7H-pyrrolo[2,3-d]pyrimidin-4-amine dihydrochloride;

6-[(2S)-2-aminopropyl]-2-chloro-7-ethyl-5-fluoro-N-[(furan-2-yl)methyl]-7H-pyrrolo[2,3-d]pyrimidin-4-amine hydrochloride;

6-[(2S)-2-aminopropyl]-2-chloro-5-fluoro-7-methyl-N-[(pyridin-4-yl)methyl]-7H-pyrrolo[2,3-d]pyrimidin-4-amine dihydrochloride;

6-[(2S)-2-aminobutyl]-2-chloro-5-fluoro-N-[(furan-2-yl)methyl]-7H-pyrrolo[2,3-d]pyrimidin-4-amine hydrochloride;

6-[(2S)-2-aminobutyl]-2-chloro-5-fluoro-N-[(furan-2-yl)methyl]-7-methyl-7H-pyrrolo[2,3-d]pyrimidin-4-amine hydrochloride;

6-[(2S)-2-aminopropyl]-2-chloro-5-fluoro-N-[(furan-2-yl)methyl]-7-(4-methoxyphenyl)-7H-pyrrolo[2,3-d]pyrimidin-4-amine hydrochloride;

6-[(2S)-2-aminopropyl]-2-chloro-5-fluoro-7-(4-methoxyphenyl)-N-[(thiophen-2-yl)methyl]-7H-pyrrolo[2,3-d]pyrimidin-4-amine hydrochloride;

6-[(2S)-2-aminopropyl]-2-chloro-5-fluoro-7-methyl-N-[(1,3-thiazol-5-yl)methyl]-7H-pyrrolo[2,3-d]pyrimidin-4-amine dihydrochloride;

6-[(2S)-2-aminopropyl]-2-chloro-5-fluoro-7-methyl-N-[(thiophen-2-yl)methyl]-7H-pyrrolo[2,3-d]pyrimidin-4-amine hydrochloride;

6-[(2S)-2-aminopropyl]-N-benzyl-2-chlor-5-fluoro-7H-pyrrolo[2,3-d]pyrimidin-4-amine hydrochloride;

6-[(2S)-2-aminopropyl]-N-benzyl-2-chloro-5-fluoro-7-methyl-7H-pyrrolo[2,3-d]pyrimidin-4-amine hydrochloride;

6-[(2S)-2-aminopropyl]-2-chloro-5-fluoro-N-[(2-fluorophenyl)methyl]-7H-pyrrolo[2,3-d]pyrimidin-4-amine hydrochloride;

6-[(2S)-2-aminopropyl]-2-chloro-5-fluoro-N-[(2-fluorophenyl)methyl]-7-methyl-7H-pyrrolo[2,3-d]pyrimidin-4-amine hydrochloride;

6-[(2S)-2-aminopropyl]-2-chloro-5-fluoro-N-[(pyridin-2-yl)methyl]-7H-pyrrolo[2,3-d]pyrimidin-4-amine dihydrochloride;

6-[(2S)-2-aminopropyl]-2-chloro-5-fluoro-7-methyl-N-[(pyridin-2-yl)methyl]-7H-pyrrolo[2,3-d]pyrimidin-4-amine dihydrochloride;

6-[(2S)-2-aminopropyl]-2-chloro-5-fluoro-N-[(pyridin-3-yl)methyl]-7H-pyrrolo[2,3-d]pyrimidin-4-amine dihydrochloride;

6-[(2S)-2-aminopropyl]-2-chloro-5-fluoro-7-methyl-N-[(pyridin-3-yl)methyl]-7H-pyrrolo[2,3-d]pyrimidin-4-amine dihydrochloride;

6-[(2S)-2-aminobutyl]-2-chloro-5-fluoro-N-[(thiophen-2-yl)methyl]-7H-pyrrolo[2,3-d]pyrimidin-4-amine hydrochloride;

6-[(2S)-2-aminobutyl]-2-chloro-5-fluoro-N-[(1,3-thiazol-2-yl)methyl]-7H-pyrrolo[2,3-d]pyrimidin-4-amine hydrochloride; and 6-[(2R)-2-aminopropyl]-2-chloro-5-fluoro-N-[(furan-2-yl)methyl]-7-methyl-7H-pyrrolo[2,3-d]pyrimidin-4-amine hydrochloride, or a tautomer thereof.

12. A pharmaceutical composition comprising a pharmaceutically acceptable excipient in admixture with a therapeutically effective amount of the compound of claim 11, or a tautomer thereof.

13. A method for treating familial dysautonomia in a subject, wherein the method comprises administering to the subject in need thereof a therapeutically effective amount of the compound of claim 11, or a tautomer thereof.

\* \* \* \* \*